(12) United States Patent
Nash et al.

(10) Patent No.: US 7,786,115 B2
(45) Date of Patent: Aug. 31, 2010

(54) AMIDE DERIVATIVES

(75) Inventors: Ian Alun Nash, Cheshire (GB);
Kenneth Mark Page, Cheshire (GB);
Paul Allen Bethel, Cheshire (GB)

(73) Assignee: AstraZeneca AB (SE)

( * ) Notice: Subject to any disclaimer, the term of this patent is extended or adjusted under 35 U.S.C. 154(b) by 489 days.

(21) Appl. No.: 11/793,781

(22) PCT Filed: Dec. 22, 2005

(86) PCT No.: PCT/GB2005/004984

§ 371 (c)(1),
(2), (4) Date: Jun. 20, 2007

(87) PCT Pub. No.: WO2006/067444

PCT Pub. Date: Jun. 29, 2006

(65) Prior Publication Data

US 2008/0146566 A1  Jun. 19, 2008

(30) Foreign Application Priority Data

Dec. 24, 2004 (GB) ................. 0428326.3
Apr. 14, 2005 (GB) ................. 0507513.0

(51) Int. Cl.
*C07D 217/00* (2006.01)
*C07D 241/36* (2006.01)
*A61K 31/496* (2006.01)
*A61K 31/498* (2006.01)

(52) U.S. Cl. ............... 514/235.2; 514/249; 514/253.05; 514/309; 544/128; 544/349; 546/141

(58) Field of Classification Search ........................ None
See application file for complete search history.

(56) References Cited

U.S. PATENT DOCUMENTS

2009/0124604 A1   5/2009  Nash et al.

FOREIGN PATENT DOCUMENTS

| WO | WO 00/55153 | 9/2000 |
| WO | WO 2006/090143 | 8/2006 |
| WO | WO 2007/020411 | 2/2007 |

*Primary Examiner*—Zinna N Davis
(74) *Attorney, Agent, or Firm*—Connolly Bove Lodge & Hutz, LLP

(57) ABSTRACT

The invention concerns a compound of the Formula I

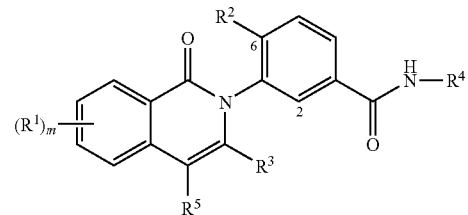

wherein m is 0-2 and each $R^1$ is a group such as hydroxy, halogeno, trifluoromethyl heterocyclyl and heterocyclyloxy; $R^2$ is halogeno, trifluoromethyl or (1-6C)alkyl; $R^3$ is hydrogen, halogeno or (1-6C)alkyl; and $R^4$ is (3-6C)cycloalkyl; or pharmaceutically-acceptable salts thereof; processes for their preparation, pharmaceutical compositions containing them and their use in the treatment of diseases or medical conditions mediated by cytokines.

11 Claims, No Drawings

AMIDE DERIVATIVES

This invention relates to amide derivatives, or pharmaceutically-acceptable salts thereof which are useful as inhibitors of cytokine mediated disease. The invention also relates to processes for the manufacture of said amide derivatives, to pharmaceutical compositions containing said amide derivatives and to their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the amide derivatives of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis, chronic obstructive pulmonary disease and adult respiratory distress syndrome), and in the production and development of various cardiovascular and cerebrovascular disorders such as congestive heart failure, acute heart failure, myocardial infarction, the formation of atherosclerotic plaques, hypertension, platelet aggregation, angina, stroke, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoperosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), chronic obstructive pulmonary disease, tumour invasiveness and tumour metastasis and multiple sclerosis. Excessive cytokine production has also been implicated in pain.

Evidence of the central role played by TNFα in the cell signalling cascade which gives rise to rheumatoid arthritis is provided by the efficacy in clinical studies of antibodies of TNFα (*The Lancet*, 1994, 344, 1125 and *British Journal of Rheumatology*, 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the amide derivatives disclosed in the present invention possesses pharmacological activity only by virtue of an effect on a single biological process, it is believed that the amide derivatives inhibit the effects of cytokines by virtue of inhibition of the enzyme p38 kinase. p38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G. J. Hanson in *Expert Opinions on Therapeutic Patents*, 1997, 7, 729-733. p38 kinase is known to exist in isoforms identified as p38α and p38β.

The compounds disclosed in the present invention are inhibitors of the production of cytokines such as TNF, in particular of TNFα, and various interleukins, in particular IL-1.

It is known from the International Patent Application WO 00/55153, that certain quinazolinone-benzamide derivatives are inhibitors of the production of cytokines such as TNF, and various interleukins.

There is a need to find further compounds that possess potent cytokine inhibitory activity and have desirable pharmacological activity profiles.

According to the present invention there is provided a compound of the Formula I

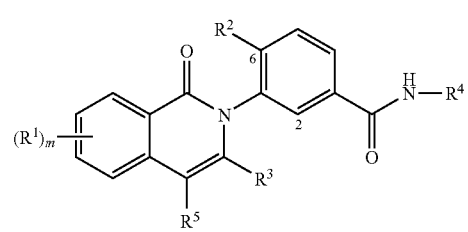

wherein m is 0, 1 or 2;

$R^1$ is halogeno, hydroxy, cyano, trifluoromethyl, trifluoromethoxy, (1-6C)alkyl, (1-6C)alkoxy, (2-6C)alkenyl, (2-6C)alkynyl, (2-6C)alkanoyl, (1-6C)alkylthio, (1-6C)alkylsulphinyl, (1-6C)alkylsulphonyl, hydroxy-(2-6C)alkoxy, amino-(2-6C)alkoxy, cyano-(2-6C)alkoxy, (1-6C)alkylamino-(2-6C)alkoxy, di-[(1-6C)alkyl]amino-(2-6C)alkoxy, (1-6C)alkoxy-(2-6C)alkoxy, carbamoyl-(1-6C)alkoxy, N-(1-6C)alkylcarbamoyl-(1-6C)alkoxy, amino-(1-6C)alkyl, (1-6C)alkylamino-(1-6C)alkyl, di[(1-6C)alkyl]amino-(1-6C)alkyl, carbamoyl-(1-6C)alkyl, N-(1-6C)alkylcarbamoyl-(1-6C)alkyl, hydroxy-(2-6C)alkylamino, cyano-(2-6C)alkylamino, halogeno-(2-6C)alkylamino, amino-(2-6C)alkylamino, (1-6C)alkoxy-(2-6C)alkylamino, (1-6C)alkylamino-(2-6C)alkylamino, di-[(1-6C)alkyl]amino-(2-6C)alkylamino, heteroaryl, heteroaryl-(1-6C)alkyl, heteroaryloxy, heteroaryl-(1-6C)alkoxy, heteroarylamino, heterocyclyl, heterocyclyl-(1-6C)alkyl, heterocyclyloxy, heterocyclyl-(1-6C)alkoxy and heterocyclylamino, and wherein any aryl, heteroaryl or heterocyclyl group in a $R^1$ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylsulphonyl, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the $R^1$ substituents defined hereinbefore which comprises a $CH_2$ group which is attached to 2 carbon atoms or a $CH_3$ group which is attached to a carbon or nitrogen atom may optionally bear on each said $CH_2$ or $CH_3$ group one or more substituents selected from halogeno, hydroxy, amino, trifluoromethyl, trifluoromethoxy, oxo, carboxy, carbamoyl, acetamido, (1-6C)alkyl, (2-6C)alkenyl, (2-6C)alkynyl, (3-6C)cycloalkyl, (3-6C)cycloalkoxy, (1-6C)alkoxy, (1-6C)alkylamino, di-[(1-6C)alkyl]amino, hydroxy-(1-6C)alkyl, (1-6C)alkoxy-(1-6C)alkyl, halogeno-(1-6C)alkyl, (1-6C)alkoxy-(2-6C)alkoxy, (1-6C)alkoxycarbonyl, carbamoyl, N-(1-6C)alkylcarbamoyl, N,N-di-[(1-6C)alkyl]carbamoyl, (1-6C)sulphonyl, (1-6C)sulphamoyl, heteroaryl, heteroaryl-(1-6C)alkyl, heterocyclyl and heterocyclyloxy, and wherein any heterocyclyl group in a $R^1$ substituent may optionally bear 1 or 2 oxo or thioxo substituents;

$R^2$ is halogeno, trifluoromethyl or (1-6C)alkyl;

$R^3$ is hydrogen, halogeno, trifluoromethyl, cyano or (1-6C)alkyl;

$R^4$ is (3-6C)cycloalkyl, (1-6C)alkyl, (1-6C)alkoxy or heteroaryl, and $R^4$ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino; and $R^5$ is hydrogen, halogeno, trifluoromethyl, cyano, (1-6C)alkyl, hydroxy-(1-6C)alkyl or (1-6C)alkoxy-(1-6C)alkyl;

or a pharmaceutically-acceptable salt thereof.

In this specification, the term (1-6C)alkyl includes straight-chain and branched-chain alkyl groups such as propyl, isopropyl and tert-butyl. References to individual alkyl groups such as "propyl" are specific for the straight-chain version only, references to individual branched-chain alkyl groups such as "isopropyl" are specific for the branched-chain version only. In this specification, the term (3-6C)cycloalkyl includes cyclopropyl, cyclobutyl, cyclopentyl, cyclopentenyl, and cyclohexyl. References to individual cycloalkyl groups such as "cyclopentyl" are specific for that 5-membered ring only.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

Suitable values for the generic radicals referred to above include those set out below.

A suitable value for $R^1$ when it is aryl is, for example, phenyl, indenyl, indanyl, naphthyl, tetrahydronaphthyl or fluorenyl, preferably phenyl.

A suitable value for $R^1$ when it is heteroaryl is, for example, an aromatic 5- or 6-membered monocyclic ring, a 9- or 10-membered bicyclic ring or a 13- or 14-membered tricyclic ring each with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl, naphthyridinyl, carbazolyl, dibenzofuranyl, dibenzothiophenyl, S,S-dioxodibenzothiophenyl, xanthenyl, dibenzo-1,4-dioxinyl, phenoxathiinyl, phenoxazinyl, dibenzothiinyl, phenothiazinyl, thianthrenyl, benzofuropyridyl, pyridoindolyl, acridinyl or phenanthridinyl, preferably furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl, more preferably furyl, thienyl, isoxazolyl, thiazolyl, pyridyl, benzothienyl, benzofurazanyl, quinolyl, carbazolyl, dibenzofuranyl or dibenzothiophenyl.

A suitable value for $R^4$ when it is heteroaryl is, for example, an aromatic 5- or 6-membered monocyclic ring with up to three ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl or pyrazinyl, 1,3,5-triazenyl, preferably furyl, thienyl, oxazolyl, isoxazolyl, imidazolyl, pyrazolyl, thiazolyl, isothiazolyl, pyridyl, pyridazinyl, pyrimidinyl or pyrazinyl, more preferably isoxazolyl or pyrazolyl.

A suitable value for $R^1$ when it is heterocyclyl is, for example, a non-aromatic saturated or partially saturated 3- to 10-membered monocyclic or bicyclic ring or a 5- to 7-membered monocyclic ring each with up to five heteroatoms selected from oxygen, nitrogen and sulphur, for example oxiranyl, oxetanyl, azetidinyl, tetrahydrofuranyl, tetrahydropyranyl, pyrrolinyl, pyrrolidinyl, imidazolinyl, imidazolidinyl, pyrazolinyl, pyrazolidinyl, 1,1-dioxidoisothiazolidinyl, morpholinyl, thiomorpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl or benzo derivatives thereof such as 2,3-dihydrobenzofuranyl, 2,3-dihydrobenzothienyl, indolinyl, isoindolinyl, chromanyl and isochromanyl, preferably 3-pyrrolin-1-yl, pyrrolidin-1-yl, pyrrolidin-2-yl, 1, morpholinylo, piperidin-3-yl, piperidin-4-yl, homopiperidin-1-yl, piperazin-1-yl or homopiperazin-1-yl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for $R^4$ or $R^1$ when it is (3-6C)cycloalkyl, or for a substituent within $R^1$ when it is (3-6C)cycloalkyl is, for example, a saturated monocyclic 3- to 6-membered carbon ring such as cyclopropyl, cyclobutyl, cyclopentyl or cyclohexyl, preferably cyclopropyl, cyclopentyl or cyclobutyl, more preferably cyclopropyl or cyclobutyl.

A suitable value for a substituent within $R^1$ when it is (3-6C)cycloalkyl-(1-6C)alkyl is, for example, cyclopropylmethyl, cyclobutylmethyl, cyclopentylmethyl, cyclohexylmethyl, cyclopropylethyl, preferably cyclopropylmethyl or cyclopropylethyl, more preferably cyclopropylmethyl.

Suitable values for various $R^1$, $R^2$, $R^3$, $R^4$ or $R^5$ groups, or for substituents on an $R^1$ or $R^4$ group, or for substituents on an aryl, heteroaryl or heterocyclyl group within $R^1$ group include:—

| | |
|---|---|
| for halogeno: | fluoro, chloro, bromo and iodo; |
| for (1-6C)alkyl: | methyl, ethyl, propyl, isopropyl and tert-butyl; |
| for (2-6C)alkenyl: | vinyl and allyl; |
| for (2-6C)alkynyl: | ethynyl and 2-propynyl; |
| for (1-6C)alkoxy: | methoxy, ethoxy, propoxy, isopropoxy and butoxy; |
| for (1-6C)alkylthio: | methylthio, ethylthio and propylthio; |
| for (1-6C)alkylsulphinyl: | methylsulphinyl, ethylsulphinyl and propylsulphinyl; |
| for (1-6C)alkylsulphonyl: | methylsulphonyl, ethylsulphonyl and propylsulphonyl; |
| for hydroxy-(2-6C)alkoxy: | 2-hydroxyethoxy, 3-hydroxypropoxy, 2-hydroxy-1-methylethoxy, 2-hydroxy-2-propoxy and 4-hydroxybutoxy; |
| for cyano-(1-6C)alkoxy: | cyanomethoxy, 2-cyanoethoxy and 3-cyanopropoxy; |
| for (1-6C)alkoxy-(2-6C)alkoxy: | 2-methoxyethoxy, 2-ethoxyethoxy, 3-methoxypropoxy, 2-methoxy-1-methylethoxy and 4-ethoxybutoxy; |
| for carbamoyl-(1-6C)alkoxy: | carbamoylmethoxy and 2-carbamoylethoxy; |
| for N-(1-6C)alkylcarbamoyl-(1-6C)alkoxy: | N-methylcarbamoylmethoxy, 2-(N-ethylcarbamoyl)ethoxy and 3-(N-methylcarbamoyl)propoxy; |
| for (3-6C)cycloalkyl-(1-6C)alkyl | (3-6C)cycloalkylmethyl and (3-6C)cycloalkylethyl; |
| for (1-6C)alkylamino: | methylamino, ethylamino and propylamino; |
| for di-[(1-6C)alkyl]amino: | dimethylamino, diethylamino and N-ethyl-N-methylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl and propionyl; |
| for halogeno-(1-6C)alkyl: | fluoromethyl, chloromethyl, bromomethyl, difluoromethyl, dichloromethyl, dibromomethyl, 2-fluoroethyl, 2-chloroethyl and 2-bromoethyl; |
| for hydroxy-(1-6C)alkyl: | hydroxymethyl, 2-hydroxyethyl, 1-hydroxyethyl and 3-hydroxypropyl; |
| for carbamoyl-(1-6C)alkyl: | carbamoylmethyl, 1-carbamoylethyl, 2-carbamoylethyl and 3-carbamoylpropyl; |
| for N-(1-6C)alkylcarbamoyl-(1-6C)alkyl: | N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for amino-(1-6C)alkyl: | aminomethyl, 2-aminoethyl, 1-aminoethyl and 3-aminopropyl; |
| for carboxy-(1-6C)alkyl: | carboxymethyl, 1-carboxyethyl, 2-carboxyethyl, 3-carboxypropyl and 4-carboxybutyl; |
| for cyano-(1-6C)alkyl: | cyanomethyl, 2-cyanoethyl, 1-cyanoethyl and 3-cyanopropyl; |
| for (1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |

-continued

| | |
|---|---|
| for di-[(1-6C)alkyl]amino-(1-6C)alkyl: | dimethylaminomethyl, diethylaminomethyl, 1-dimethylaminoethyl, 2-dimethylaminoethyl and 3-dimethylaminopropyl. |
| for amino-(2-6C)alkoxy: | 2-aminoethoxy, 2-amino-1-methylethoxy, 3-aminopropoxy, 2-amino-2-methylpropoxy and 4-aminobutoxy; |
| for (1-6C)alkylamino-(2-6C)alkoxy: | 2-methylaminoethoxy, 2-methylamino-1-methylethoxy, and 3-ethylaminopropoxy, |
| for di-[(1-6C)alkyl]amino-(2-6C)alkoxy: | 2-dimethylaminoethoxy, 2-diethylaminoethoxy, 2-dimethylaminopropoxy, 2-dimethylamino-2-methylethoxy, 3-dimethylaminopropoxy and 4-dimethylaminobutoxy, 2-(N-methyl-N-isopropylamino)ethoxy, and 2-(N-ethyl-N-isopropylamino)ethoxy; |
| for amino-(2-6C)alkylamino: | 2-aminoethylamino, 3-aminopropylamino, 2-amino-2-methylpropylamino and 4-aminobutylamino; |
| for halogeno-(2-6C)alkylamino: | 2-fluoroethylamino, 2-chloroethylamino, 2-bromoethylamino, 3-fluoropropylamino and 3-chloropropylamino; |
| for hydroxy-(2-6C)alkylamino: | 2-hydroxyethylamino, 3-hydroxypropylamino, 2-hydroxy-2-methylpropylamino and 4-hydroxybutylamino; |
| for cyano-(1-6C)alkylamino: | cyanomethylamino, 2-cyanoethylamino and 3-cyanopropylamino; |
| for (1-6C)alkoxy-(2-6C)alkylamino: | 2-methoxyethylamino, 2-ethoxyethylamino, 3-methoxypropylamino and 3-ethoxypropylamino; |
| for (1-6C)alkylamino-(2-6C)alkylamino: | 2-methylaminoethylamino, 2-ethylaminoethylamino, 2-propylaminoethylamino, 3-methylaminopropylamino, 3-ethylaminopropylamino, 2-methylamino-2-methylpropylamino and 4-methylaminobutylamino; |
| for di-[(1-6C)alkyl]amino-(2-6C)alkylamino: | 2-dimethylaminoethylamino, 2-(N-ethyl-N-methylamino)ethylamino, 2-diethylaminoethylamino, 2-dipropylaminoethylamino, 3-dimethylaminopropylamino, 3-diethylaminopropylamino, 2-dimethylamino-2-methylpropylamino and 4-dimethylaminobutylamino; |
| for aryl-(1-6C)alkyl: | benzyl, 2-phenylethyl, 2-phenylpropyl and 3-phenylpropyl; |
| for aryl-(1-6C)alkoxy: | benzyloxy and 2-phenylethoxy; |
| for aryloxy: | phenoxy and 2-naphthyloxy; |
| for arylamino: | anilino; |
| for heteroaryl-(1-6C)alkyl: | heteroarylmethyl, heteroarylethyl, 2-heteroarylethyl, 2-heteroarylpropyl and 3-heteroarylpropyl; |
| for heteroaryl-(1-6C)alkoxy: | heteroarylmethoxy and 2-heteroarylethoxy; |
| for heterocyclyl-(1-6C)alkyl: | heterocyclylmethyl, 2-heterocyclylethyl, 2-heterocyclylpropyl and 3-heterocyclylpropyl; |
| for heterocyclyl-(1-6C)alkoxy: | heterocyclylmethoxy and 2-heterocyclylethoxy; |
| for (2-6C)alkanoyloxy: | acetoxy and propionyloxy: |
| for (1-6C)alkanoylamino: | formamido, acetamido and propionamido; |
| for (1-6C)alkoxycarbonyl-(1-6C)alkyl: | methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; |

A suitable pharmaceutically-acceptable salt of a compound of the Formula I, for example, an acid-addition salt of a compound of the Formula I which is sufficiently basic, for example, an acid-addition salt with an inorganic or organic acid such as hydrochloric, hydrobromic, sulphuric, phosphoric, trifluoroacetic, citric, maleic, tartaric, fumaric, hemifumaric, succinic, hemisuccinic, mandelic, methanesulphonic, dimethanesulphonic, ethane-1,2-sulphonic, benzenesulphonic, salicylic or 4-toluenesulphonic acid.

Further values of m, $R^1$, $R^2$, $R^3$, $R^4$ and $R^5$ are as follows. Such values may be used where appropriate with any of the definitions, claims or embodiments defined hereinbefore or hereinafter.

m is 0, 1 or 2.

m is 0 or 1.

m is 1 or 2.

m is 0 m is 1.

m is 2.

$R^1$ is halogeno, hydroxy, cyano, trifluoromethyl, trifluoromethoxy, (1-6C)alkyl, (1-6C)alkoxy, (2-6C)alkenyl, (2-6C)alkynyl, (2-6C)alkanoyl, (1-6C)alkylthio, (1-6C)alkylsulphonyl, hydroxy-(2-6C)alkoxy, amino-(2-6C)alkoxy, cyano-(2-6C)alkoxy, (1-6C)alkylamino-(2-6C)alkoxy, di-[(1-6C)alkyl]amino-(2-6C)alkoxy, (1-6C)alkoxy-(2-6C)alkoxy, di[(1-6C)alkyl]amino-(1-6C)alkyl, carbamoyl-(1-6C)alkyl, heteroaryl-(1-6C)alkyl, heteroaryl-(1-6C)alkoxy, heterocyclyl, heterocyclyl-(1-6C)alkyl, heterocyclyloxy and heterocyclyl-(1-6C)alkoxy, and wherein any heteroaryl or heterocyclyl group in a $R^1$ substituent may optionally bear 1 or 2 substituents selected from hydroxy, halogeno, (1-6C)alkyl, (3-6C)cycloalkyl-(1-6C)alkyl, (3-6C)cycloalkyl-(1-6C)alkoxy, (1-6C)alkoxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylsulphonyl, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, and wherein any of the $R^1$ substituents defined hereinbefore which comprises a $CH_2$ group which is attached to 2 carbon atoms or a $CH_3$ group which is attached to a carbon or nitrogen atom may optionally bear on each said $CH_2$ or $CH_3$ group one or more substituents selected from halogeno, hydroxy, trifluoromethyl, oxo (1-6C)alkyl, (2-6C)alkenyl, (2-6C)alkynyl, (3-6C)cycloalkyl, (1-6C)alkoxy, (1-6C)alkylamino, di-[(1-6C)alkyl]amino, hydroxy-(1-6C)alkyl, (1-6C)alkoxy-(1-6C)alkyl, halogeno-(1-6C)alkyl, (1-6C)alkoxycarbonyl, heteroaryl, heteroaryl-(1-6C)alkyl, heterocyclyl and heterocyclyloxy, and wherein any heterocyclyl group in a $R^1$ substituent may optionally bear 1 or 2 oxo or thioxo substituents.

$R^1$ is halogeno, hydroxy, (1-6C)alkoxy, (2-6C)alkenyl, (2-6C)alkynyl, (2-6C)alkanoyl, (1-6C)alkylthio, (1-6C)alkylsulphonyl, amino-(2-6C)alkoxy, (1-6C)alkylamino-(2-6C)alkoxy, di-[(1-6C)alkyl]amino-(2-6C)alkoxy, di[(1-6C)alkyl]amino-(1-6C)alkyl, carbamoyl-(1-6C)alkyl, heteroaryl-(1-6C)alkyl, heterocyclyl, heterocyclyloxy and heterocyclyl-(1-6C)alkoxy, and wherein any heteroaryl or heterocyclyl group in a $R^1$ substituent may optionally bear 1 or 2 substituents selected from hydroxy, halogeno, (1-6C)alkyl, (3-6C)cycloalkyl-(1-6C)alkyl, (3-6C)cycloalkyl-(1-6C)alkoxy, (1-6C)alkoxy, (1-6C)alkoxycarbonyl-(1-6C)alkyl, N-(1-6C)alkylcarbamoyl, N,N-di-[(1-6C)alkyl]carbamoyl, halogeno-(1-6C)alkyl, hydroxy-(1-6C)alkyl, (1-6C)alkoxy-(1-6C)alkyl, cyano-(1-6C)alkyl, and wherein any of the $R^1$ substituents defined hereinbefore which comprises a $CH_2$ group which is attached to 2 carbon atoms or a $CH_3$ group which is attached to a carbon or nitrogen atom may optionally bear on each said $CH_2$ or $CH_3$ group one or more substituents selected from halogeno, hydroxy, trifluoromethyl, (1-6C)alkyl, (3-6C)cycloalkyl, (1-6C)alkoxy, di-[(1-6C)alkyl]amino, (1-6C)alkoxy-(1-6C)alkyl, (1-6C)alkoxycarbonyl, heteroaryl-(1-6C)alkyl, heterocyclyl and heterocyclyloxy.

$R^1$ is halogeno, hydroxy, (1-6C)alkoxy, (2-6C)alkenyl, (2-6C)alkynyl, (2-6C)alkanoyl, (1-6C)alkylthio, (1-6C)alkylsulphonyl, amino-(2-6C)alkoxy, (1-6C)alkylamino-(2-6C)alkoxy, di-[(1-6C)alkyl]amino-(2-6C)alkoxy, di[(1-6C)alkyl]amino-(1-6C)alkyl, carbamoyl-(1-6C)alkyl, heteroaryl-(1-6C)alkyl, heterocyclyl, heterocyclyloxy and heterocyclyl-(1-6C)alkoxy, and wherein any heteroaryl or heterocyclyl group in a $R^1$ substituent may optionally bear 1 or 2 substituents selected from hydroxy, halogeno, (1-6C)alkyl, (3-6C)cycloalkyl-(1-6C)alkyl, (3-6C)cycloalkyl-(1-6C)alkoxy, (1-6C)alkoxy, (1-6C)alkoxycarbonyl-(1-6C)alkyl, N-(1-6C)alkylcarbamoyl, N,N-di-[(1-6C)alkyl]carbamoyl, halogeno-(1-6C)alkyl, hydroxy-(1-6C)alkyl, (1-6C)alkoxy-(1-6C)alkyl, cyano-(1-6C)alkyl, and wherein any of the $R^1$ substituents defined hereinbefore which comprises a $CH_2$ group which is attached to 2 carbon atoms or a $CH_3$ group which is attached to a carbon or nitrogen atom may optionally bear on each said $CH_2$ or $CH_3$ group one or more substituents selected from halogeno, hydroxy, trifluoromethyl, (1-6C)alkyl, (3-6C)cycloalkyl, (1-6C)alkoxy, di-[(1-6C)alkyl]amino, (1-6C)alkoxy-(1-6C)alkyl, (1-6C)alkoxycarbonyl, heteroaryl-(1-6C)alkyl, heterocyclyl and heterocyclyloxy.

$R^1$ is fluoro, chloro, bromo, iodo, hydroxy, methoxy, ethoxy, propoxy, acetyl, methylthio, ethylthio, methylsulphonyl, ethylsulphonyl, 2-aminoethoxy, 2-amino-1-methylethoxy, 3-aminopropoxy, 2-amino-2-methylpropoxy, 2-methylaminoethoxy, 2-methylamino-1-methylethoxy, 3-ethylaminopropoxy, 2-dimethylaminoethoxy, 2-diethylaminoethoxy, 2-dimethylaminopropoxy, 2-dimethylamino-2-methylethoxy, 3-dimethylaminopropoxy, dimethylaminomethyl, diethylaminomethyl, 1-dimethylaminoethyl, 2-dimethylaminoethyl, 3-dimethylaminopropyl, carbamoylmethyl, 1-carbamoylethyl, 2-carbamoylethyl, 3-carbamoylpropyl, heteroarylmethyl, heteroarylethyl, heterocyclyl, heterocyclyloxy, heterocyclylmethoxy and 2-heterocyclylethoxy, and wherein any heteroaryl or heterocyclyl group in a $R^1$ substituent may optionally bear 1 or 2 substituents selected from hydroxy, is fluoro, chloro, bromo, iodo, methyl, ethyl, propyl, isopropyl, cyclobutylmethyl, cyclopropylmethyl, cyclobutylmethoxy, cyclopropylmethoxy, acetyl, methoxy, ethoxy, propoxy, methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl, 3-ethoxycarbonylpropyl, N-methylcarbamoyl, N-ethylcarbamoyl, N-propylcarbamoyl, N,N-dimethylcarbamoyl, N-ethyl-N-methylcarbamoyl, N,N-diethylcarbamoyl, fluoromethyl, chloromethyl, bromomethyl, difluoromethyl, dichloromethyl, dibromomethyl, 2-fluoroethyl, 2-chloroethyl, 2-bromoethyl, hydroxymethyl, 2-hydroxyethyl, 1-hydroxyethyl, 3-hydroxypropyl, methoxymethyl, ethoxymethyl, 1-methoxyethyl, 2-methoxyethyl, 2-ethoxyethyl and 3-methoxypropyl, cyanomethyl, 2-cyanoethyl, 1-cyanoethyl, 3-cyanopropyl, and wherein any of the $R^1$ substituents defined hereinbefore which comprises a $CH_2$ group which is attached to 2 carbon atoms or a $CH_3$ group which is attached to a carbon or nitrogen atom may optionally bear on each said $CH_2$ or $CH_3$ group one or more substituents selected from fluoro, chloro, bromo, iodo, hydroxy, trifluoromethyl, methyl, ethyl, propyl, isopropyl, tert-butyl, cyclopropyl, cyclobutyl, cyclopentyl, methoxy, ethoxy, propoxy, isopropoxy, tert-butoxy, dimethylamino, diethylamino, N-ethyl-N-methylamino, methoxymethyl, ethoxymethyl, 1-methoxyethyl, 2-methoxyethyl, 2-ethoxyethyl, 3-methoxypropyl, methoxycarbonyl, ethoxycarbonyl, propoxycarbonyl, tert-butoxycarbonyl, heteroarylmethyl, heteroarylethyl, heterocyclyl and heterocyclyloxy.

$R^1$ is fluoro, chloro, bromo, iodo, hydroxy, methoxy, ethoxy, propoxy, acetyl, methylthio, ethylthio, methylsulphonyl, ethylsulphonyl, 2-aminoethoxy, 2-amino-1-methylethoxy, 3-aminopropoxy, 2-amino-2-methylpropoxy, 2-methylaminoethoxy, 2-methylamino-1-methylethoxy, 3-ethylaminopropoxy, 2-dimethylaminoethoxy, 2-diethylaminoethoxy, 2-dimethylaminopropoxy, 2-dimethylamino-2-methylethoxy, 3-dimethylaminopropoxy, dimethylaminomethyl, diethylaminomethyl, 1-dimethylaminoethyl, 2-dimethylaminoethyl, 3-dimethylaminopropyl, carbamoylmethyl, 1-carbamoylethyl, 2-carbamoylethyl, 3-carbamoylpropyl, piperidinylmethyl, piperidinylethyl, homopiperidinyl, piperazinyl, homopiperazinyl, morpholinyl, dihydropyridinyl, tetrahydropyridinyl, dihydropyrimidinyl or tetrahydropyrimidinyl, piperidinyloxy, pyrrolodinyloxy, morpholinylethoxy, pyrrolidinylethoxy, piperidinylethoxy, azetidinylethoxy, and wherein any heteroaryl or heterocyclyl group in a $R^1$ substituent may optionally bear 1 or 2 substituents selected from hydroxy, is fluoro, chloro, bromo, iodo, methyl, ethyl, propyl, isopropyl, cyclobutylmethyl, cyclopropylmethyl, cyclobutylmethoxy, cyclopropylmethoxy, acetyl, methoxy, ethoxy, propoxy, methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl, 3-ethoxycarbonylpropyl, N-methylcarbamoyl, N-ethylcarbamoyl, N-propylcarbamoyl, N,N-dimethylcarbamoyl, N-ethyl-N-methylcarbamoyl, N,N-diethylcarbamoyl, fluoromethyl, chloromethyl, bromomethyl, difluoromethyl, dichloromethyl, dibromomethyl, 2-fluoroethyl, 2-chloroethyl, 2-bromoethyl, hydroxymethyl, 2-hydroxyethyl, 1-hydroxyethyl, 3-hydroxypropyl, methoxymethyl, ethoxymethyl, 1-methoxyethyl, 2-methoxyethyl, 2-ethoxyethyl and 3-methoxypropyl, cyanomethyl, 2-cyanoethyl, 1-cyanoethyl, 3-cyanopropyl, and wherein any of the $R^1$ substituents defined hereinbefore which comprises a $CH_2$ group which is attached to 2 carbon atoms or a $CH_3$ group which is attached to a carbon or nitrogen atom may optionally bear on each said $CH_2$ or $CH_3$ group one or more substituents selected from fluoro, chloro, bromo, iodo, hydroxy, trifluoromethyl, methyl, ethyl, propyl, isopropyl, tert-butyl, cyclopropyl, cyclobutyl, cyclopentyl, methoxy, ethoxy, propoxy, isopropoxy, tert-butoxy, dimethylamino, diethylamino, N-ethyl-N-methylamino, methoxymethyl, ethoxymethyl, 1-methoxyethyl, 2-methoxyethyl, 2-ethoxyethyl, 3-methoxypropyl, methoxycarbonyl, ethoxycarbonyl, propoxycarbonyl, tert-butoxycarbonyl, piperidinylmethyl, piperidinylethyl, homopiperidinyl, piperazinyl, homopiperazinyl, morpholinyl, dihydropyridinyl, tetrahydropyridinyl, dihydropyrimidinyl, tetrahydropyrimidinyl, piperidinyloxy and pyrrolodinyloxy.

$R^1$ is amino-(2-6C)alkoxy, (1-6C)alkylamino-(2-6C)alkoxy, di-[(1-6C)alkyl]amino-(2-6C)alkoxy, amino-(2-6C)alkylamino, (1-6C)alkylamino-(2-6C)alkylamino, di-[(1-6C)alkyl]amino-(2-6C)alkylamino, aryl, aryl-(1-6C)alkyl, aryl-(1-6C)alkoxy, aryloxy, arylamino, heteroaryl, heteroaryl-(1-6C)alkyl, heteroaryloxy, heteroaryl-(1-6C)alkoxy, heteroarylamino, heterocyclyl, heterocyclyl-(1-6C)alkyl, heterocyclyloxy, heterocyclyl-(1-6C)alkoxy or heterocyclylamino, and wherein any aryl, heteroaryl or heterocyclyl group in a $R^1$ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the $R^1$ substituents defined hereinbefore which comprises a $CH_2$ group which is attached to 2 carbon atoms or a $CH_3$ group which is attached to a carbon atom may optionally bear on each said $CH_2$ or $CH_3$ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino, and wherein any heterocyclyl group in a $R^1$ substituent may optionally bear 1 or 2 oxo or thioxo substituents.

$R^1$ is aryl, aryl-(1-6C)alkyl, aryl-(1-6C)alkoxy, aryloxy, arylamino, heteroaryl, heteroaryl-(1-6C)alkyl, heteroaryloxy, heteroaryl-(1-6C)alkoxy, heteroarylamino, heterocyclyl, heterocyclyl-(1-6C)alkyl, heterocyclyloxy, heterocyclyl-(1-6C)alkoxy or heterocyclylamino, and wherein any aryl, heteroaryl or heterocyclyl group in a $R^1$ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the $R^1$ substituents defined hereinbefore which comprises a $CH_2$ group which is attached to 2 carbon atoms or a $CH_3$ group which is attached to a carbon atom may optionally bear on each said $CH_2$ or $CH_3$ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino, and wherein any heterocyclyl group in a $R^1$ substituent may optionally bear 1 or 2 oxo or thioxo substituents.

$R^1$ is amino-(2-6C)alkoxy, (1-6C)alkylamino-(2-6C)alkoxy, di-[(1-6C)alkyl]amino-(2-6C)alkoxy, amino-(2-6C)alkylamino, (1-6C)alkylamino-(2-6C)alkylamino or di-[(1-6C)alkyl]amino-(2-6C)alkylamino, and wherein any of the $R^1$ substituents defined hereinbefore which comprises a $CH_2$ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

R¹ is heterocyclyl, heterocyclyl-(1-6C)alkyl, heterocyclyloxy, heterocyclyl-(1-6C)alkoxy or heterocyclylamino, and wherein any heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

R¹ is heterocyclyl, heterocyclyloxy or heterocyclyl-(1-6C)alkoxy, and wherein any heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

R¹ is heterocyclyl or heterocyclyloxy, and wherein any heterocyclyl group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

R¹ is a non-aromatic saturated or partially saturated 3- to 10-membered monocyclic or bicyclic ring or a 5- to 7-membered monocyclic ring each with up to five heteroatoms selected from oxygen, nitrogen and sulphur, and wherein any group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

R¹ is heterocyclyl or heterocyclyloxy, and wherein any heterocyclyl group in a R¹ substituent may optionally bear 1 or 2 substituents selected from (1-6C)alkyl, (3-6C)cycloalkyl-(1-6C)alkyl, (1-6C)alkoxycarbonyl, (1-6C)alkoxycarbonyl-(1-6C)alkyl and hydroxy-(1-6C)alkyl.

R¹ is morpholinyl, thiomorpholinyl, piperidinyl, piperidinyloxy, homopiperidinyl, piperazinyl or homopiperazinyl, and wherein any group in a R¹ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the R¹ substituents defined hereinbefore which comprises a CH₂ group which is attached to 2 carbon atoms or a CH₃ group which is attached to a carbon atom may optionally bear on each said CH₂ or CH₃ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino.

R¹ is morpholinyl, thiomorpholinyl, piperidinyl, piperidinyloxy, homopiperidinyl, piperazinyl or homopiperazinyl, and wherein any heterocyclyl group in a R¹ substituent may optionally bear 1 or 2 substituents selected from (1-6C)alkyl, (3-6C)cycloalkyl-(1-6C)alkyl, (1-6C)alkoxycarbonyl, (1-6C)alkoxycarbonyl-(1-6C)alkyl and hydroxy-(1-6C)alkyl.

R¹ is piperidinyl, piperidinyloxy, homopiperidinyl, piperazinyl or homopiperazinyl, and wherein any group in a R¹ substituent may optionally bear 1 or 2 substituents selected from methyl, ethyl, propyl, isopropyl, cyclopropylmethyl, tert-butoxycarbonyl, tert-butoxycarbonylmethyl and 2-hydroxyethyl.

R¹ is 4-methylpiperazin-1yl.
R² is halogeno, trifluoromethyl or (1-6C)alkyl.
R² is trifluoromethyl or (1-6C)alkyl.
R² is trifluoromethyl or methyl.

$R^2$ is methyl.

$R^3$ is hydrogen, halogeno, trifluoromethyl, cyano or (1-6C)alkyl.

$R^3$ is hydrogen, halogeno or (1-6C)alkyl.

$R^3$ is hydrogen or halogeno.

$R^3$ is hydrogen or chloro.

$R^3$ is chloro.

$R^3$ is hydrogen.

$R^4$ is (3-6C)cycloalkyl, (1-6C)alkoxy, (1-6C)alkyl or heteroaryl, and $R^4$ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino.

$R^4$ is cyclopropyl, cyclobutyl, cyclopentyl, methoxy, ethoxy, methyl, ethyl, propyl, isoxazolyl, oxazolyl, furanyl, thiazolyl, pyrazolyl or pyridyl, and $R^4$ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino.

$R^4$ is (3-6C)cycloalkyl, (1-6C)alkoxy, (1-6C)alkyl or heteroaryl, and $R^4$ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino.

$R^4$ is cyclopropyl, cyclobutyl, cyclopentyl, methoxy, ethoxy, methyl, ethyl, propyl, isoxazolyl, oxazolyl, furanyl, thiazolyl, pyrazolyl or pyridyl, and $R^4$ may be optionally substituted by one or more substituents selected from halogeno, hydroxy, amino and (1-6C)alkyl.

$R^4$ is cyclopropyl, cyclobutyl, cyclopentyl, methoxy, ethoxy, methyl, ethyl, propyl, isoxazolyl, oxazolyl, furanyl, thiazolyl, pyrazolyl or pyridyl.

$R^4$ is cyclopropyl, cyclobutyl, methoxy, ethyl or isoxazolyl.

$R^4$ is cyclopropyl, cyclobutyl, methoxy, ethyl, pyrazolyl or isoxazolyl.

$R^4$ is (3-6C)cycloalkyl, and $R^4$ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino.

$R^4$ is (3-5C)cycloalkyl, and $R^4$ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino.

$R^4$ is cyclopropyl, cyclobutyl, or cyclopentyl, and $R^4$ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino.

$R^4$ is cyclopropyl or cyclobutyl, and R may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino.

$R^4$ is cyclopropyl and may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino.

$R^4$ is cyclopropyl and may be optionally substituted by one or more substituents selected from halogeno, hydroxy, (1-6C)alkyl, (2-6C)alkenyl, (2-6C)alkynyl and (1-6C)alkoxy.

$R^4$ is cyclopropyl and may be optionally substituted by one or more substituents selected from fluoro, chloro, hydroxy, methyl, ethyl, and methoxy.

$R^4$ is cyclopropyl and may be optionally substituted by methyl and methoxy.

$R^4$ is cyclopropyl and may be optionally substituted by methyl.

$R^4$ is cyclopropyl, cyclobutyl or cyclopentyl.

$R^4$ is cyclopropyl or cyclobutyl.

$R^4$ is cyclopropyl.

$R^5$ is hydrogen, halogeno, trifluoromethyl, cyano or (1-6C)alkyl.

$R^5$ is hydrogen, halogeno or (1-6C)alkyl.

$R^5$ is hydrogen or halogeno.

$R^5$ is hydrogen or chloro.

$R^5$ is chloro.

$R^5$ is hydrogen.

$R^5$ is hydrogen, halogeno, trifluoromethyl, cyano, (1-6C)alkyl, hydroxy-(1-6C)alkyl or (1-6C)alkoxy-(1-6C)alkyl.

$R^5$ is hydrogen, halogeno, trifluoromethyl, cyano, hydroxymethyl, methyl or ethyl.

Particular novel compounds of the invention include, for example, amide derivatives of the Formula I, or pharmaceutically-acceptable salts thereof, wherein:—

(a) m is 0 or 1;

$R^1$ is heterocyclyl, heterocyclyl-(1-6C)alkyl, heterocyclyloxy, heterocyclyl-(1-6C)alkoxy or heterocyclylamino, and wherein any heterocyclyl group in a $R^1$ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the $R^1$ substituents defined hereinbefore which comprises a $CH_2$ group which is attached to 2 carbon atoms or a $CH_3$ group which is attached to a carbon atom may optionally bear on each said $CH_2$ or $CH_3$ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino;

$R^2$ is trifluoromethyl or methyl;

$R^3$ is hydrogen or chloro;

$R^4$ is cyclopropyl, cyclobutyl, cyclopentyl, methyl, ethyl, propyl, isoxazolyl, oxazolyl, furanyl, thiazolyl, pyrazolyl or pyridyl, and $R^4$ may be optionally substituted by one or more substituents selected from halogeno, hydroxy, amino and (1-6C)alkyl; and $R^5$ is hydrogen or chloro.

(b) m is 0 or 1;

$R^1$ is heterocyclyl or heterocyclyloxy, and wherein any heterocyclyl group in a $R^1$ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the $R^1$ substituents defined hereinbefore which comprises a $CH_2$ group which is attached to 2 carbon atoms or a $CH_3$ group which is attached to a carbon atom may optionally bear on each said $CH_2$ or $CH_3$ group one or more substituents selected from hydroxy, amino, (1-6C) alkyl, (2-6C)alkenyl, (2-6C)alkynyl, (1-6C)alkoxy, (1-6C) alkylamino and di-[(1-6C)alkyl]amino;

$R^2$ is methyl;

$R^3$ is hydrogen;

$R^4$ is cyclopropyl, cyclobutyl, cyclopentyl, methyl, ethyl, propyl, isoxazolyl, oxazolyl, furanyl, thiazolyl, pyrazolyl or pyridyl, and $R^4$ may be optionally substituted by one or more substituents selected from halogeno, hydroxy, amino and (1-6C)alkyl; and $R^5$ is hydrogen.

(c) m is 1;

$R^1$ is heterocyclyl or heterocyclyloxy, and wherein any heterocyclyl group in a $R^1$ substituent may optionally bear 1 or 2 substituents selected from (1-6C) alkyl, (3-6C)cycloalkyl-(1-6C)alkyl, (1-6C)alkoxycarbonyl, (1-6C)alkoxycarbonyl-(1-6C)alkyl and hydroxy-(1-6C)alkyl;

$R^2$ is methyl;

$R^3$ is hydrogen; and $R^4$ is cyclopropyl, cyclobutyl ethyl, pyrazolyl or isoxazolyl; and $R^5$ is hydrogen.

A particular preferred compound of the invention is, for example:—

N-cyclopropyl-4-methyl-3-(1-oxoisoquinolin-2(1H)-yl) benzamide;

N-cyclopropyl-3-(7-methoxy-1-oxoisoquinolin-2(1H)-yl)-4-methylbenzamide;

N-cyclopropyl-3-[7-[2-(dimethylamino)ethoxy]-1-oxoisoquinolin-2(1H)-yl]-4-methylbenzamide;

3-(7-bromo-1-oxoisoquinolin-2(1H)-yl)-N-cyclopropyl-4-methylbenzamide;

N-cyclopropyl-4-methyl-3-[1-oxo-7-(2-piperidin-1-ylethoxy)isoquinolin-2(1H)-yl]benzamide;

N-cyclopropyl-3-(7-hydroxy-1-oxoisoquinolin-2(1H)-yl)-4-methylbenzamide;

N-cyclopropyl-3-[7-{2-[(3R)-3-fluoropyrrolidin-1-yl]ethoxy}-1-oxoisoquinolin-2(1H)-yl]-4-methylbenzamide;

N-cyclopropyl-4-methyl-3-[7-[2-(1,4-oxazepan-4-yl)ethoxy]-1-oxoisoquinolin-2(1H)-yl]benzamide;

N-cyclopropyl-3-[7-{2-[(2-methoxyethyl)(methyl)amino]ethoxy}-1-oxoisoquinolin-2(1H)-yl]-4-methylbenzamide;

3-[7-{2-[(cyclobutylmethyl)(methyl)amino]ethoxy}-1-oxoisoquinolin-2(1H)-yl]-N-cyclopropyl-4-methylbenzamide;

N-cyclopropyl-4-methyl-3-[7-(2-morpholin-4-ylethoxy)-1-oxoisoquinolin-2(1H)-yl]benzamide;

N-cyclopropyl-4-methyl-3-[1-oxo-7-(2-pyrrolidin-1-ylethoxy)isoquinolin-2(1H)-yl]benzamide;

N-cyclopropyl-3-[7-{2-[(3R)-3-hydroxypyrrolidin-1-yl]ethoxy}-1-oxoisoquinolin-2(1H)-yl]-4-methylbenzamide;

N-cyclopropyl-3-[7-{2-[(2S)-2-(methoxymethyl)pyrrolidin-1-yl]ethoxy}-1-oxoisoquinolin-2(1H)-yl]-4-methylbenzamide;

N-cyclopropyl-3-[7-{2-[isopropyl(2-methoxyethyl)amino]ethoxy}-1-oxoisoquinolin-2(1H)-yl]-4-methylbenzamide;

N-cyclopropyl-3-[7-{2-[isopropyl(methyl)amino]ethoxy}-1-oxoisoquinolin-2(1H)-yl]-4-methylbenzamide;

N-cyclopropyl-3-[7-[3-(dimethylamino)propoxy]-1-oxoisoquinolin-2(1H)-yl]-4-methylbenzamide;

3-[7-[2-(dimethylamino)ethoxy]-1-oxoisoquinolin-2(1H)-yl]-N-isoxazol-3-yl-4-methylbenzamide;

3-[7-[2-(dimethylamino)ethoxy]-1-oxoisoquinolin-2(1H)-yl]-N-ethyl-4-methylbenzamide;

N-cyclopropyl-3-[7-[(1-ethylpiperidin-4-yl)oxy]-1-oxoisoquinolin-2(1H)-yl]-4-methylbenzamide;

N-isoxazol-3-yl-4-methyl-3-[7-(4-methylpiperazin-1-yl)-1-oxoisoquinolin-2(1H)-yl]benzamide;

N-cyclopropyl-4-methyl-3-[7-(4-methylpiperazin-1-yl)-1-oxoisoquinolin-2(1H)-yl]benzamide;

N-cyclopropyl-4-methyl-3-[7-{2-[methyl(tetrahydro-2H-pyran-4-yl)amino]ethoxy}-1-oxoisoquinolin-2(1H)-yl] benzamide;

N-cyclopropyl-4-methyl-3-[7-{2-[methyl(tetrahydrofuran-2-ylmethyl)amino]ethoxy}-1-oxoisoquinolin-2(1H)-yl]benzamide;

N-cyclopropyl-4-methyl-3-[7-{2-[methyl(prop-2-yn-1-yl)amino]ethoxy}-1-oxoisoquinolin-2(1H)-yl]benzamide;

N-cyclopropyl-3-[7-{2-[(3S)-3-fluoropyrrolidin-1-yl]ethoxy}-1-oxoisoquinolin-2(1H)-yl]-4-methylbenzamide;

N-cyclopropyl-3-[7-[2-(4,4-difluoropiperidin-1-yl)ethoxy]-1-oxoisoquinolin-2(1H)-yl]-4-methylbenzamide;

N-cyclopropyl-3-[7-[2-(3,3-difluoropyrrolidin-1-yl)ethoxy]-1-oxoisoquinolin-2(1H)-yl]-4-methylbenzamide;

N-cyclopropyl-3-[7-[2-(4-fluoropiperidin-1-yl)ethoxy]-1-oxoisoquinolin-2(1H)-yl]-4-methylbenzamide;

N-cyclopropyl-3-[7-[2-(3-fluoropiperidin-1-yl)ethoxy]-1-oxoisoquinolin-2(1H)-yl]-4-methylbenzamide;

N-cyclopropyl-3-[7-{2-[(2S,6S)-2,6-dimethylmorpholin-4-yl]ethoxy}-1-oxoisoquinolin-2(1H)-yl]-4-methylbenzamide;

N-cyclopropyl-3-[7-{2-[(2R,6S)-2,6-dimethylmorpholin-4-yl]ethoxy}-1-oxoisoquinolin-2(1H)-yl]-4-methylbenzamide;

N-cyclopropyl-4-methyl-3-[1-oxo-7-[3-(4-propionylpiperazin-1-yl)propoxy]isoquinolin-2(1H)-yl]benzamide;

N-ethyl-4-methyl-3-[7-(2-morpholin-4-ylethoxy)-1-oxoisoquinolin-2(1H)-yl]benzamide;

N-cyclopropyl-3-[7-[3-(4,4-difluoropiperidin-1-yl)propoxy]-1-oxoisoquinolin-2(1H)-yl]-4-methylbenzamide;

N-cyclopropyl-3-[7-{3-[isopropyl(methyl)amino]propoxy}-1-oxoisoquinolin-2(1H)-yl]-4-methylbenzamide;

N-cyclopropyl-4-methyl-3-[1-oxo-7-(3-piperidin-1-ylpropoxy)isoquinolin-2(1H)-yl]benzamide;

N-cyclopropyl-4-methyl-3-[7-{3-[methyl(tetrahydrofuran-2-ylmethyl)amino]propoxy}-1-oxoisoquinolin-2(1H)-yl] benzamide;

N-cyclopropyl-3-[7-{3-[(2R,6S)-2,6-dimethylmorpholin-4-yl]propoxy}-1-oxoisoquinolin-2(1H)-yl]-4-methylbenzamide;

N-cyclopropyl-4-methyl-3-[1-oxo-7-(3-pyrrolidin-1-ylpropoxy)isoquinolin-2(1H)-yl]benzamide;

N-cyclopropyl-4-methyl-3-[7-(3-morpholin-4-ylpropoxy)-1-oxoisoquinolin-2(1H)-yl]benzamide;

N-cyclopropyl-4-methyl-3-[7-{3-[methyl(prop-2-yn-1-yl)amino]propoxy}-1-oxoisoquinolin-2(1H)-yl]benzamide;

N-cyclopropyl-3-[7-[3-(3,3-difluoropyrrolidin-1-yl)propoxy]-1-oxoisoquinolin-2(1H)-yl]-4-methylbenzamide;

N-cyclopropyl-3-[7-[3-(3-fluoropiperidin-1-yl)propoxy]-1-oxoisoquinolin-2(1H)-yl]-4-methylbenzamide;

N-cyclopropyl-4-methyl-3-[7-{2-[4-(methylsulfonyl)piperazin-1-yl]ethoxy}-1-oxoisoquinolin-2(1H)-yl]benzamide;

N-ethyl-3-[7-{2-[isopropyl(methyl)amino]ethoxy}-1-oxoisoquinolin-2(1H)-yl]-4-methylbenzamide;

N-ethyl-3-[7-{2-[(3R)-3-fluoropyrrolidin-1-yl]ethoxy}-1-oxoisoquinolin-2(1H)-yl]-4-methylbenzamide;

N-cyclopropyl-4-methyl-3-[7-{3-[methyl(tetrahydro-2H-pyran-4-yl)amino]propoxy}-1-oxoisoquinolin-2(1H)-yl]benzamide;
3-[7-[3-(dimethylamino)propyl]-1-oxoisoquinolin-2(1H)-yl]-N-isoxazol-3-yl-4-methylbenzamide;
N-cyclopropyl-3-[7-[3-(4-fluoropiperidin-1-yl)propoxy]-1-oxoisoquinolin-2(1H)-yl]-4-methylbenzamide;
N-cyclopropyl-3-[7-{3-[(3R)-3-fluoropyrrolidin-1-yl]propoxy}-1-oxoisoquinolin-2(1H)-yl]-4-methylbenzamide;
N-cyclopropyl-3-[7-{3-[(3S)-3-fluoropyrrolidin-1-yl]propoxy}-1-oxoisoquinolin-2(1H)-yl]-4-methylbenzamide;
N-ethyl-4-methyl-3-[1-oxo-7-(2-piperidin-1-ylethoxy)isoquinolin-2(1H)-yl]benzamide;
N-ethyl-3-(7-hydroxy-1-oxoisoquinolin-2(1H)-yl)-4-methylbenzamide
N-cyclopropyl-3-[7-{2-[isobutyl(methyl)amino]ethoxy}-1-oxoisoquinolin-2(1H)-yl]-4-methylbenzamide;
N-cyclopropyl-3-[7-{2-[ethyl(methyl)amino]ethoxy}-1-oxoisoquinolin-2(1H)-yl]-4-methylbenzamide;
N-cyclopropyl-3-[7-[2-(diisopropylamino)ethoxy]-1-oxoisoquinolin-2(1H)-yl]-4-methylbenzamide;
N-cyclopropyl-4-methyl-3-[7-{2-[(2S)-2-methylpiperidin-1-yl]ethoxy}-1-oxoisoquinolin-2(1H)-yl]benzamide;
N-cyclopropyl-3-[7-{2-[ethyl(isopropyl)amino]ethoxy}-1-oxoisoquinolin-2(1H)-yl]-4-methylbenzamide;
N-cyclopropyl-3-[7-[2-(diethylamino)ethoxy]-1-oxoisoquinolin-2(1H)-yl]-4-methylbenzamide;
3-[7-{2-[tert-butyl(methyl)amino]ethoxy}-1-oxoisoquinolin-2(1H)-yl]-N-cyclopropyl-4-methylbenzamide;
3-[7-{2-[cyclohexyl(isopropyl)amino]ethoxy}-1-oxoisoquinolin-2(1H)-yl]-N-cyclopropyl-4-methylbenzamide;
3-[7-{2-[cyclohexyl(ethyl)amino]ethoxy}-1-oxoisoquinolin-2(1H)-yl]-N-cyclopropyl-4-methylbenzamide;
3-[7-{2-[cyclohexyl(methyl)amino]ethoxy}-1-oxoisoquinolin-2(1H)-yl]-N-cyclopropyl-4-methylbenzamide;
N-cyclopropyl-3-[7-{2-[2-(hydroxymethyl)morpholin-4-yl]ethoxy}-1-oxoisoquinolin-2(1H)-yl]-4-methylbenzamide;
N-cyclopropyl-3-[7-{2-[(2S)-2-(hydroxymethyl)piperidin-1-yl]ethoxy}-1-oxoisoquinolin-2(1H)-yl]-4-methylbenzamide;
3-[7-(2-azetidin-1-ylethoxy)-1-oxoisoquinolin-2(1H)-yl]-N-ethyl-4-methylbenzamide;
N-cyclopropyl-3-[7-[2-(isopropylamino)ethoxy]-1-oxoisoquinolin-2(1H)-yl]-4-methylbenzamide;
3-[7-{2-[allyl(methyl)amino]ethoxy}-1-oxoisoquinolin-2(1H)-yl]-N-ethyl-4-methylbenzamide;
N-ethyl-3-[7-{2-[ethyl(methyl)amino]ethoxy}-1-oxoisoquinolin-2(1H)-yl]-4-methylbenzamide;
3-[7-[2-(diethylamino)ethoxy]-1-oxoisoquinolin-2(1H)-yl]-N-ethyl-4-methylbenzamide;
N-ethyl-3-[7-{2-[ethyl(isopropyl)amino]ethoxy}-1-oxoisoquinolin-2(1H)-yl]-4-methylbenzamide;
N-cyclobutyl-3-(7-hydroxy-1 oxoisoquinolin-2(1H)-yl)-4-methylbenzamide;
N-cyclopropyl-4-methyl-3-[7-[2-(methylamino)ethoxy]-1-oxoisoquinolin-2(1H)-yl]benzamide;
N-ethyl-3-[7-{2-[(3R)-3-hydroxypyrrolidin-1-yl]ethoxy}-1-oxoisoquinolin-2(1H)-yl]-4-methylbenzamide;
N-ethyl-4-methyl-3-[1-oxo-7-(2-pyrrolidin-1-ylethoxy)isoquinolin-2(1H)-yl]benzamide;
N-ethyl-3-[7-[2-(4-hydroxypiperidin-1-yl)ethoxy]-1-oxoisoquinolin-2(1H)-yl]-4-methylbenzamide;
N-ethyl-4-methyl-3-[7-(2-{methyl[(2-methyl-1,3-thiazol-4-yl)methyl]amino}ethoxy)-1-oxoisoquinolin-2(1H)-yl]benzamide;
N-ethyl-3-[7-[2-(4-fluoropiperidin-1-yl)ethoxy]-1-oxoisoquinolin-2(1H)-yl]-4-methylbenzamide;
N-ethyl-4-methyl-3-[1-oxo-7-{2-[(3aR,6aS)-tetrahydro-5H-[1,3]dioxolo[4,5-c]pyrrol-5-yl]ethoxy} isoquinolin-2(1H)-yl]benzamide;
3-(7-hydroxy-1-oxoisoquinolin-2(1H)-yl)-4-methyl-N-(1-methylcyclopropyl)benzamide;
N-isoxazol-3-yl-4-methyl-3-[7-(3-morpholin-4-ylpropyl)-1-oxoisoquinolin-2(1H)-yl]benzamide;
N-isoxazol-3-yl-4-methyl-3-[7-(2-morpholin-4-ylethoxy)-1-oxoisoquinolin-2(1H)-yl]benzamide;
3-[7-(2-aminoethoxy)-1-oxoisoquinolin-2(1H)-yl]-N-cyclopropyl-4-methylbenzamide;
N-isoxazol-3-yl-4-methyl-3-[1-oxo-7-(2-piperidin-1-ylethoxy)isoquinolin-2(1H)-yl]benzamide;
3-[7-{2-[tert-butyl(methyl)amino]ethoxy}-1-oxoisoquinolin-2(1H)-yl]-N-ethyl-4-methylbenzamide;
3-[7-{2-[isopropyl(methyl)amino]ethoxy}-1-oxoisoquinolin-2(1H)-yl]-4-methyl-N-(1-methyl-1H-pyrazol-3-yl)benzamide;
3-[7-{2-[isopropyl(methyl)amino]ethoxy}-1-oxoisoquinolin-2(1H)-yl]-4-methyl-N-(1-methyl-1H-pyrazol-5-yl)benzamide;
3-[7-{2-[isopropyl(methyl)amino]ethoxy}-1-oxoisoquinolin-2(1H)-yl]-N-methoxy-4-methylbenzamide;
N-cyclobutyl-3-[7-{2-[isopropyl(methyl)amino]ethoxy}-1-oxoisoquinolin-2(1H)-yl]-4-methylbenzamide;
N-cyclopropyl-3-(7-methoxy-4-methyl-1-oxoisoquinolin-2(1H)-yl)-4-methylbenzamide;
N-cyclopropyl-3-[7-{2-[isopropyl(methyl)amino]ethoxy}-4-methyl-1-oxoisoquinolin-2(1H)-yl]-4-methylbenzamide;
N-ethyl-3-[7-{2-[isopropyl(methyl)amino]ethoxy}-4-methyl-1-oxoisoquinolin-2(1H)-yl]-4-methylbenzamide;
N-cyclopropyl-3-[4-(hydroxymethyl)-7-methoxy-1-oxoisoquinolin-2(1H)-yl]-4-methylbenzamide;
N-ethyl-3-[7-{2-[ethyl(methyl)amino]ethoxy}-4-methyl-1-oxoisoquinolin-2(1H)-yl]-4-methylbenzamide;
3-[7-[2-(dimethylamino)ethoxy]-4-methyl-1-oxoisoquinolin-2(1H)-yl]-N-ethyl-4-methylbenzamide;
N-cyclobutyl-3-[7-{2-[isopropyl(methyl)amino]ethoxy}-4-methyl-1-oxoisoquinolin-2(1H)-yl]-4-methylbenzamide;
N-cyclobutyl-3-[7-{2-[ethyl(methyl)amino]ethoxy}-4-methyl-1-oxoisoquinolin-2(1H)-yl]-4-methylbenzamide; and
N-cyclobutyl-3-[7-[2-(dimethylamino)ethoxy]-4-methyl-1-oxoisoquinolin-2(1H)-yl]-4-methylbenzamide;

or a pharmaceutically-acceptable salt thereof.

Compounds of the Formula I, or a pharmaceutically-acceptable salts thereof, may be prepared by any process known to be applicable to the preparation of chemically-related compounds. Suitable processes are illustrated by, for example, those in WO 00/55153. Such processes, when used to prepare a novel compound of the Formula I are provided as a further feature of the invention and are illustrated by the following representative process variants in which, unless otherwise stated, $R^1$, $R^2$, $R^3$, $R^4$ and $R^5$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) A compound of the Formula I, or a pharmaceutically-acceptable salt thereof, may be prepared by dehydration of a compound of the Formula II

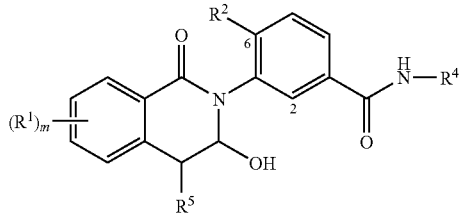

II with a suitable acid, for example, an inorganic or organic acid such as hydrochloric, hydrobromic, sulphuric, acetic, trifluoroacetic, citric or maleic acid.

The reaction is also preferably carried out in a suitable inert solvent or diluent, for example water, methanol, ethanol, tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, 0 to 150° C., conveniently at or near 25° C.

The compound of the Formula II may be prepared by reduction of the corresponding compound of the Formula III

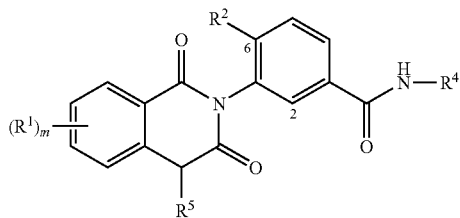

III with a suitable reducing agent, for example, a metal hydride reducing agent, for example sodium borohydride. Alternative reducing agents can be found in Advanced Organic Chemistry, 4th Edition, by Jerry March, published by John Wiley & Sons 1992.

The reaction is also preferably carried out in a suitable inert solvent or diluent, for example methanol, ethanol, tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, 0 to 150° C., conveniently at or near 25° C.

The compound of the Formula III may be prepared by reaction of the corresponding compound of the Formula IV

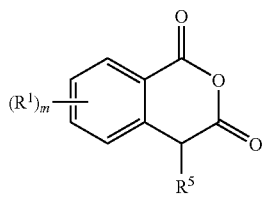

IV with an aniline of Formula V

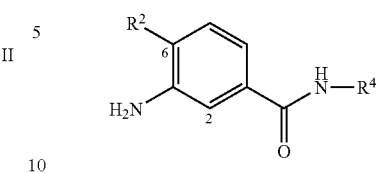

V wherein $R^1$, $R^2$, $R^4$ and $R^5$ are as defined hereinbefore and wherein any functional group is protected if necessary.

The reaction is also preferably carried out in a suitable inert solvent or diluent, for example toluene, N,N-dimethylformamide, N,N-dimethylacetamide, N-methylpyrrolidin-2-one, dimethylsulphoxide or acetone, and at a temperature in the range, for example, 0 to 200° C., conveniently at or near 150° C.

The compound of the Formula IV may be prepared by cyclisation of a reactive derivative of a compound VI

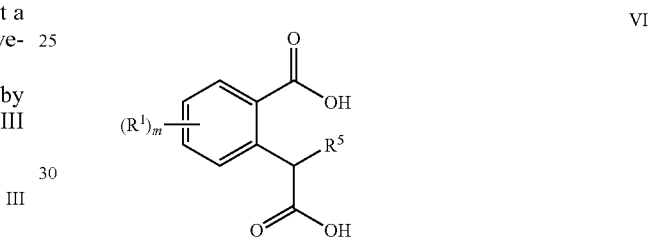

VI wherein $R^1$ and $R^5$ are as defined hereinbefore and wherein any functional group is protected if necessary, and:
(i) removing any protecting groups; and
(ii) optionally forming a pharmaceutically-acceptable salt.

Suitable reactive derivatives of a compound of the Formula VI are, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an anhydride formed by the reaction of the acid and acyl halide such as acetyl chloride; an active ester, for example an ester formed by the reaction of the acid with a phenol such as pentafluorophenol, with an ester such as pentafluorophenyl trifluoroacetate or with an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide. The reaction may conveniently be carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene.

The reaction may also conveniently be carried out in the presence of a suitable acid such as, for example, an inorganic or organic acid such as hydrochloric, hydrobromic, sulphuric, acetic, trifluoroacetic, citric or maleic acid.

The reaction is also preferably carried out in a suitable inert solvent or diluent, for example toluene, N,N-dimethylformamide, N N-dimethylacetamide, N-methylpyrrolidin-2-one, dimethylsulphoxide or acetone, and at a temperature in the range, for example, 0 to 200° C., conveniently at or near 25° C.

The compound of the Formula VI may be prepared by reaction of a 2-Bromobenzoic acid of the Formula VII

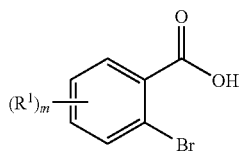

VII with a compound of the Formula VIII

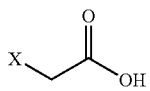

VIII wherein $R^5$ is as defined hereinbefore, and wherein X is a suitable activated acetic acid equivalent, and wherein the carboxy group is protected if necessary, and:
(i) removing any protecting groups; and
(ii) optionally forming a pharmaceutically-acceptable salt.

A suitable activated acetic acid equivalent of a compound of the formula VIII is, for example, a protected malonic ester, for example dimethyl malonate; a β-keto ester, for example ethyl acetoacetate.

The reaction may conveniently be carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene.

The reaction is also preferably carried out in a suitable inert solvent or diluent, for example toluene, N N-dimethylformamide, N,N-dimethylacetamide, N-methylpyrrolidin-2-one, dimethylsulphoxide or the suitable activated acetic acid equivalent, and at a temperature in the range, for example, 0 to 200° C., conveniently at or near 80° C.

Typical conditions include the use of a suitable transition metal catalyst precursor, for example copper (I) bromide. The transformation may also be effected using the aryl iodides or aryl triflate versions of a compound of the formula VIII.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or aryl aliphatic alcohol or of an ester-forming silanol (the said alcohol or silanol preferably containing 1-20 carbon atoms). Examples of carboxy protecting groups include straight or branched chain (1-12C)alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl)silyl groups (for example trimethylsilyl and tert-butyldimethylsilyl); tri(lower alkyl)silyl lower alkyl groups (for example trimethylsilylethyl); and (2-6C)alkenyl groups (for example allyl and vinylethyl). Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; trialkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

(b) A compound of the Formula I or a pharmaceutically-acceptable salt thereof, may be prepared by reacting a carboxylic acid of the Formula X or a reactive derivative thereof as defined hereinbefore,

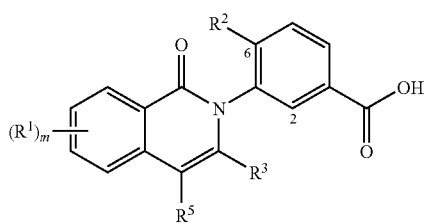

with a amine of the Formula XI,

under standard amide bond forming conditions as defined hereinbefore, wherein variable groups are as defined hereinbefore and wherein any functional group is protected if necessary, and:

(i) removing any protecting groups; and
(ii) optionally forming a pharmaceutically-acceptable salt.

The reaction is preferably carried out in the presence of a suitable base as defined hereinbefore The reaction is preferably carried out in a suitable inert solvent or diluent, for example tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, −78 to 150° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C. Other typical conditions include activating the carboxy group of the compound of Formula X, for example by treatment with a halo reagent (for example oxalyl or thionyl chloride) to form an acyl halide in an organic solvent at ambient temperature and then reacting the activated compound with the amine of Formula VI.

A carboxylic acid of the Formula X may be prepared by deprotection under standard conditions as defined hereinbefore of the corresponding protected carboxy compound of the Formula XII, wherein P is a carboxy protecting group, as defined hereinbefore. Typically this transformation is achieved using an aqueous solution of sodium hydroxide or anhydrous sodium methoxide in an alcoholic medium, such as methanol in the region of 40-65° C. to give the carboxylate salt. The desired carboxylic acid X is recovered by addition of an aqueous acid, typically dilute hydrochloric acid.

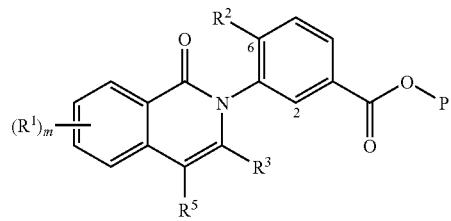

(c) A compound of the Formula I wherein a substituent on $R^1$ or $R^4$ is (1-6C)alkoxy or substituted (1-6C)alkoxy, (1-6C)alkylamino or di-[(1-6C)alkyl]amino may be prepared by the alkylation, conveniently in the presence of a suitable base as defined hereinbefore, of a compound of the Formula I wherein a substituent on $R^1$ or $R^4$ is hydroxy or amino as appropriate.

The reaction is preferably carried out in the presence of a suitable inert solvent or diluent, for example a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 150° C., preferably in the range 20 to 80° C.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1-6C)alkyl chloride, bromide or iodide or a substituted (1-6C)alkyl chloride, bromide or iodide, in the presence of a suitable base as defined hereinbefore, in a suitable inert solvent or diluent as defined hereinbefore and at a temperature in the range, for example, 10 to 140° C., conveniently at or near ambient temperature.

(d) A compound of the Formula I wherein a substituent a substituent on $R^1$ or $R^4$ is amino, (1-6C)alkylamino or di-[(1-6C)alkyl]amino may be prepared by the reaction, conveniently in the presence of a suitable base as defined hereinbefore, of a compound of the Formula I wherein a substituent on $R^1$ or $R^4$ is a suitable leaving group with an appropriate amine.

A suitable leaving group is, for example, a halogeno group such as fluoro, chloro or bromo, a (1-6C)alkanesulphonyloxy group such as methanesulphonyloxy or an arylsulphonyloxy group such as 4-toluenesulphonyloxy.

The reaction is conveniently carried out in the presence of a suitable inert diluent or carrier as defined hereinbefore and at a temperature in the range, for example, 20 to 200° C., conveniently in the range 75 to 150° C.

The following biological assays and Examples serve to illustrate the present invention.

Biological Assays

The following assays can be used to measure the p38 kinase-inhibitory, the TNF-inhibitory and anti-arthritic effects of compounds of the Formula I:

In Vitro Enzyme Assay

The ability test compounds to inhibit the enzyme p38 kinase was assessed. Activity of the test compound against each of the p38α and p38β isoforms of the enzyme was determined.

Human recombinant MKK6 (GenBank Accession Number G1209672) was isolated from Image clone 45578 (*Genomics*, 1996, 33, 151) and utilised to produce protein in the form of a GST fusion protein in a pGEX vector using analogous procedures to those disclosed by J. Han et al., *Journal of Biological Chemistry*, 1996, 271, 2886-2891. p38% (GenBank Accession Number G529039) was isolated by PCR amplification of human lymphoblastoid cDNA (GenBank Accession Number GM1416)] using oligonucleotides designed for the 5' and 3' ends of the human p38α gene using analogous procedures to those described by J. Han et al., *Biochimica et Biophysica Acta*, 1995, 1265, 224-227 and Y. Jiang et al., *Journal of Biological Chemistry*, 1996, 271, 17920-17926. P38α protein was expressed in *E. coli* in a PET vector. Human recombinant p38% was produced as a 5' c-myc, 6His tagged protein. Both MKK6 and the p38α protein were purified using standard protocols: the GST MKK6 was purified using a glutathione sepharose column and the p38a protein was purified using nickel chelate columns. Human recombinant p38β (SAPK2b/p38β2) protein was obtained from Professor Philip Cohen, MRC Protein Phosphorylation Unit, University of Dundee, Scotland.

The p38 enzymes were activated prior to use by incubation with MKK6. The unactivated *E. coli-expressed* MKK6 retained sufficient activity to fully activate both isoforms of p38. In brief, MKK6 (5 ul of 12 mg/ml) was incubated with p38α (50 ul of 10 mg/ml) for 3 hours at 30° C. in "Kinase buffer" [550 ul; pH 7.4 buffer comprising Tris HCl (50 mM), EGTA (0.1 mM), sodium orthovanadate (0.1 mM) and β-mercaptoethanol (0.1%)], Mg [75 μl of 100 mM Mg(OCOCH$_3$)$_2$] and ATP (75 μl of 1 mM). The activation incubate for p38β was similar to the above except containing p38β enzyme (82 ul at 3.05 mg/ml) and 518 ul "Kinase buffer" p38α and p38β activation incubates were either used fresh or aliquoted and stored at –80° C.

The test compound was solubilised in DMSO (10 mM) and 1:3 serial dilutions in DMSO carried out in polypropylene plates (Costar 3365). Compound dilutions were then diluted 1:10 in "Kinase buffer" and 10 μl transferred to a microtiter assay plate (Costar 3596). Control wells contained 10 μl (1:10 dilution in kinase buffer) DMSO. 'Kinase Assay Mix' [30 μl; comprising Myelin Basic Protein (Sigma M-1891; 0.5 ml of a 6.66 mg/ml solution in "Kinase buffer"), activated p38α enzyme (3.8 μl) and 'Kinase Buffer' (2.55 ml)] was then added. Control wells on each plate either contained the above "Kinase Assay Mix" (n=6 replicates) or contained "Kinase Assay Mix" in which the activated p38 enzyme was replaced by Kinase buffer (n=6 replicates). 'Labelled ATP' was then added to all wells [10 μl; comprising 50 μM ATP, 5 μCi $^{33}$P ATP (Amersham International cat. no. AH9968) and 50 mM Mg(OCOCH$_3$)$_2$]. For p38β, 7.6 μl activated p38β enzyme was included in the "Kinase Assay Mix". The final concentration of test compound was 2.4 μM-0.001 μM (n=2 replicates). Microtiter plates were incubated at ambient temperature (with gentle agitation) for 60 minutes and the reaction stopped by addition of 20% trichloroacetic acid (TCA) (50 μl). The precipitate protein was captured onto filter plates (PerkinElmer 6005174) using a Packard Filtermate harvester (2% TCA wash) which was then dried overnight and 25 μl MICROSCINT O (Packard O6013611) added to each well. Plates were counted on a Top Count scintillation counter. Dose response curves were generated using an in house automated data analysis package and an Origin curve fitting package.

In Vitro Cell-based Assays (i) PBMC

The ability of a test compound to inhibit TNFα production was assessed by using human peripheral blood mononuclear cells which synthesise and secrete TNFα when stimulated with lipopolysaccharide (LPS).

Peripheral blood mononuclear cells (PBMC) were isolated from heparinised (10 units/ml heparin) human blood by density centrifugation (Lymphoprep™; Axis Shield 1114545). Mononuclear cells were resuspended in "Culture Medium" [RPMI 1640 medium (Sigma R0883) containing 50 units/ml penicillin, 50 μg/ml streptomycin (Sigma P4458) and 2 mM glutamine (Sigma G7513)] supplemented with 1% heat-inactivated human AB serum (Sigma H-1513)]. Compounds were solubilised in DMSO (Sigma D2650) at a concentration of 20 mM, diluted 1:100 in "culture medium" and serial dilutions carried out in "Culture Medium" containing 1% DMSO. PBMCs (2.2×10$^5$ cells in 160 μl culture medium) were incubated with 20 μl of varying concentrations of test compound (duplicate cultures) or 2011 culture medium containing 1% DMSO (control wells) for 30 minutes at 37° C. in a humidified (5% CO$_2$/95% air) incubator (Corning 3595; 96 well flat-bottom tissue culture plates). 20 μl lipopolysaccharide [LPS *E. Coli* 0111:B4 (Sigma L-2630), final concentration 0.1 μg/ml] solubilised in "Culture Medium" was added to appropriate wells. 20 μl Culture Medium was added to "medium alone" control wells. Six "LPS alone" and six "medium alone" controls were included on each 96 well plate.

The test compound was tested for TNFα inhibitory activity over a final concentration dose range of 201M-0.0001 μM. Each test included a known TNFα inhibitor i.e. the p38 MAPK inhibitor, SB203580 (Lee, J. C., et al (1994) Nature 372 p739-746). Plates were incubated for 24 hours at 37° C. (humidified incubator) after which 100 μl of the supernatant was removed from each well and stored at –80° C. (96 well round-bottom plates; Corning 3799). TNFα levels were determined in each sample using a human TNFα ELISA (using R&D Systems paired antibodies, MAB610 and BAF210.

$$\% \text{ inhibition} = \frac{(LPS \text{ alone} - \text{medium alone}) - (\text{test concentration} - \text{medium alone})}{(LPS \text{ alone} - \text{medium alone})} \times 100$$

(ii) Human Whole Blood

The ability of a test compound to inhibit TNFα production was also assessed in a human whole blood assay. Human whole blood secretes TNFα when stimulated with LPS.

Heparinised (10 units/ml) human blood was obtained from volunteers. 160 μl whole blood was added to 96 well round-bottom plates (Corning 3799). Compounds were solubilised in DMSO at a concentration of 10 mM, diluted 1:100 in "culture medium" [RPMI 1640 medium (Sigma) containing 50 units/ml penicillin, 50 μg/ml streptomycin and 2 mM glutamine] and subsequently serial dilutions were made in culture medium containing 1% DMSO. 20 μl of each test concentration was added to appropriate wells (triplicate cultures)(final concentration dose range of 10 μM-0.000 μM). 20 μl of RPMI culture medium containing 1% DMSO was added to control wells.

Plates were incubated for 30 minutes at 37° C. (humidified incubator), prior to addition of 20 μl LPS (final concentration 10 μg/ml). Culture medium was added to control wells. Six "LPS alone" and six "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 80 μl plasma removed and stored at −80° C. (Corning 3799 plates). TNFα levels were measured by ELISA using paired antibodies from R&D Systems (catalogue nos. MAB610 and BAF210).

In Vivo Assessment

The ability of a test compound to inhibit TNFα synthesis in vivo was assessed in a rat lipopolysaccharide (LPS)-challenge model. Briefly, compound was dosed orally (30-0.1 mg/kg in 20% DMSO (Sigma D-2650)/60% PEG 400 (Fisher Scientific P/3676/08)/20% sterile de-ionised water; 5 animals per group) to female Wistar Alderley Park (AP) rats (100-150 g) at appropriate timepoints prior to challenge with LPS. Control animals (10 per group) were dosed vehicle alone. LPS (LPS *E. Coli* 0111:B4; Sigma L-2630) was administered intravenously (30 μg in 0.2 ml sterile physiological saline (Phoenix Pharma Ltd). Blood was obtained 60 minutes later from anaesthetised animals and serum isolated after 2 hours incubation at ambient temperature (Sarstedt serum separator 1 ml microtubes, ref 41.1500.005) and centrifugation. Serum samples were stored at −20° C. prior to determination of TNFα content by ELISA (R&D Systems; MAB510, anti-rat TNFα primary antibody, and BAF510, biotinylated anti-rat TNFα secondary antibody.). % inhibition TNFα calculated as 100−[compound treated/LPS control×100]

Test as Anti-arthritic Agent

Compound was tested for activity in a rat streptococcal cell-wall-induced arthritis model (SCW) [for further information see Carlson, R. P. and Jacobsen, P. B. (1999) Comparison of adjuvant and streptococcal cell-wall-induced arthritis in the rat. In In Vivo Models of Inflammation, eds Morgan, D. W. and Marshall, L. A., Birkhauser Verlag, Basel, Switzerland].

Briefly, female Lewis rats (160-180 g) were sensitised by intra-articular injection of 5 μg streptococcal cell wall (Lee Labs, PG-PS 100P) in 20 μl sterile physiological saline into the left ankle. Responsiveness was assessed 3 days later and animals randomised. Arthritis was induced 21 days after sensitisation (designated day 0) by intravenous injection of 100 μg scw (in 500 μl sterile physiological saline). Compound was dosed orally (50-1 mg/kg once daily) (4 ml/kg) either before (day-1) or after disease onset (day+1) (10 animals per test group; vehicle 0.5% (w/v) HPMC and 0.1% (w/v) polysorbate 80). Control animals (n=10) received vehicle alone. "Non-induced" control animals which were dosed with vehicle were also included (5 animals per group). Animals were weighed on a daily basis from day-1 and ankle diameters measured with Vernier callipers on a daily basis from day-1. At termination on day 6, left hind limbs were removed and fixed in 10% formalin for histological assessment.

Although the pharmacological properties of the compounds of the Formula I vary with structural change as expected, in general a compound of the Formula a gives over 50% inhibition of p38α and/or p38β at concentrations less than 1 μM. No physiologically unacceptable toxicity was observed at the effective dose for compounds tested of the present invention.

According to a further aspect of the invention there is provided a pharmaceutical composition which comprises compound of the Formula I, or a pharmaceutically-acceptable salt thereof, in association with a pharmaceutically-acceptable diluent or carrier.

According to a further aspect of the invention there is provided a pharmaceutical composition for use in the treatment of diseases mediated by cytokines which comprises compound of the Formula I, or a pharmaceutically-acceptable salt thereof, in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent compounded with an appropriate and convenient amount of excipients which may vary from about 5 to about 98 percent by weight of the total composition.

The size of the dose for therapeutic or prophylactic purposes of a compound of the Formula I of the invention will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

According to a further aspect of the invention there is provided a compound of the Formula I, or a pharmaceutically-acceptable salt thereof, for use in a method of treatment of the human or animal body by therapy.

According to a further aspect of the invention there is provided the use of a compound of the Formula I, or a pharmaceutically-acceptable salt thereof, in the manufacture of a medicament.

According to a further aspect of the invention there is provided the use of a compound of the Formula I, or a pharmaceutically-acceptable salt thereof, in the manufacture of a medicament for use in the treatment of medical conditions mediated by cytokines.

In a further aspect the present invention provides a method of treating diseases or medical conditions mediated by cytokines which comprises administering to a warm-blooded animal an effective amount of a compound of the Formula I, or a pharmaceutically-acceptable salt thereof.

In a further aspect the present invention provides a method of treating a disease or medical condition mediated by cytokines which comprises administering to a warm-blooded animal in need thereof a cytokine inhibiting amount of a compound of the Formula I, or a pharmaceutically-acceptable salt thereof.

In a further aspect the present invention provides a method of treating a disease or medical condition mediated by the production or effect of cytokines which comprises administering to a warm-blooded animal in need thereof a cytokine inhibiting amount of a compound of the Formula I, or a pharmaceutically-acceptable salt thereof.

In a further aspect on the invention there is provided a method for inhibiting the production or effect of a cytokine in a warm-blooded animal in need thereof a p38 kinase inhibiting amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in inhibiting TNF.

In a further aspect the present invention provides a method of inhibiting TNF which comprises administering to a warm-blooded animal an effective amount of a compound of the Formula I, or a pharmaceutically-acceptable salt thereof.

In a further aspect the present invention provides a compound of the Formula I, or a pharmaceutically-acceptable salt thereof, in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable thereof, in the manufacture of a medicament for use in the treatment of rheumatoid arthritis, asthma, chronic obstructive pulmonary disease, inflammatory bowel disease, multiple sclerosis, AIDS, septic shock, congestive heart failure, ischaemic heart disease or psoriasis.

In a further aspect the present invention provides a method of treating rheumatoid arthritis, asthma, chronic obstructive pulmonary disease, inflammatory bowel disease, multiple sclerosis, AIDS, septic shock, congestive heart failure, ischaemic heart disease or psoriasis which comprises administering to a warm-blooded animal an effective amount of a compound of the Formula I, or a pharmaceutically-acceptable salt thereof.

A compound of the Formula I may be used in combination with other drugs and therapies used in the treatment of disease states which would benefit from the inhibition of cytokines, in particular TNF and IL-1. For example, a compound of the Formula I could be used in combination with drugs and therapies used in the treatment of rheumatoid arthritis, asthma, chronic obstructive pulmonary disease, inflammatory bowel disease, multiple sclerosis, AIDS, septic shock, congestive heart failure, ischaemic heart disease, psoriasis and the other disease states mentioned earlier in this specification.

For example, by virtue of its ability to inhibit cytokines, a compound of the Formula I is of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I of the present invention with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt thereof, in conjunction or admixture with a cyclooxygenase inhibitory non-steroidal anti-inflammatory agent, and a pharmaceutically-acceptable diluent or carrier.

A compound of the Formula I may also be used with anti-inflammatory agents such as an inhibitor of the enzyme 5-lipoxygenase.

A compound of the Formula I may also be used in the treatment of conditions such as rheumatoid arthritis in combination with antiarthritic agents such as gold, methotrexate, steroids and pencillinamine, and in conditions such as osteoarthritis in combination with steroids.

A compound of the Formula I may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

A compound of the Formula I may be used in the treatment of asthma in combination with antiasthmatic agents such as steroids, bronchodilators and leukotriene antagonists.

In particular, for the treatment of the inflammatory diseases rheumatoid arthritis, psoriasis, inflammatory bowel disease, chronic obstructive pulmonary disease, asthma and allergic rhinitis a compound of the present invention may be combined with agents such as TNF-α inhibitors such as anti-TNF monoclonal antibodies (such as Remicade, CDP-870 and $D_2E_7$.) and TNF receptor immunoglobulin molecules (such as Enbrel.reg.), non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold.

The present invention still further relates to the combination of a compound of the Formula I together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY×1005.

The present invention still further relates to the combination of a compound of the Formula I together with a receptor antagonist for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the Formula I together with a PDE4 inhibitor including inhibitors of the isoform PDE4D.

The present invention still further relates to the combination of a compound of the Formula I together with a antihistaminic $H_1$ receptor antagonists such as cetirizine, loratadine, desloratadine, fexofenadine, astemizole, azelastine, and chlorpheniramine.

The present invention still further relates to the combination of a compound of the Formula I together with a gastroprotective $H_2$ receptor antagonist.

The present invention still further relates to the combination of a compound of the Formula I together with an $α_1$- and $α_2$-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the Formula I together with anticholinergic agents such as ipratropium bromide; tiotropium bromide; oxitropium bromide; pirenzepine; and telenzepine.

The present invention still further relates to the combination of a compound of the Formula I together with a $β_1$- to $β_4$-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the Formula I together with an insulin-like growth factor type I (IGF-1) mimetic.

The present invention still further relates to the combination of a compound of the Formula I together with an inhaled glucocorticoid with reduced systemic side effects, such as prednisone, prednisolone, flunisolide, triamcinolone acetonide, beclomethasone dipropionate, budesonide, fluticasone propionate, and mometasone furoate.

The present invention still further relates to the combination of a compound of the Formula I together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-12.

The present invention still further relates to the combination of a compound of the Formula I together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR3, CXCR4 and CXCR5 (for the C—X—C family) and $CX_3CR1$ for the C—$X_3$—C family.

The present invention still further relates to the combination of a compound of the Formula I together with antiviral agents such as Viracept, AZT, aciclovir and famciclovir, and antisepsis compounds such as Valant.

The present invention still further relates to the combination of a compound of the Formula I together with cardiovascular agents such as calcium channel blockers, lipid lowering agents such as statins, fibrates, beta-blockers, Ace inhibitors, Angiotensin-2 receptor antagonists and platelet aggregation inhibitors.

The present invention still further relates to the combination of a compound of the Formula I together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

The present invention still further relates to the combination of a compound of the Formula I together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-$B_1$- and $B_2$-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin $NK_1$ and $NK_3$ receptor antagonists selected from the group consisting of NKP-608C; SB-233412 (talnetant); and D-4418; (xx) elastase inhibitors selected from the group consisting of UT-77 and ZD-0892; (xxi) TNF? converting enzyme inhibitors (TACE); (xxii) induced nitric oxide synthase inhibitors (iNOS) or (xxiii) chemoattractant receptor-homologous molecule expressed on TH2 cells, (CRTH2 antagonists).

A compound of the Formula I may also be used in combination with osteoporosis agents such as roloxifene, droloxifene, lasofoxifene or fosomax and immunosuppressant agents such as FK-506, rapamycin, cyclosporine, azathioprine, and methotrexate.

A compound of the Formula I may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc and P2X7 receptor antagonists.

A compound of the Formula I can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

If formulated as a fixed dose such combination products employ a compound of the Formula I within the dosage range described herein and the other pharmaceutically-active agent within its approved dosage range. Sequential use is contemplated when a combination formulation is inappropriate.

Although a compound of the Formula I is primarily of value as a therapeutic agent for use in warm-blooded animals (including man), it is also useful whenever it is required to inhibit the effects of cytokines. Thus, it is useful as pharmacological standard for use in the development of new biological tests and in the search for new pharmacological agents.

The invention will now be illustrated in the following non-limiting Examples in which, unless otherwise stated:—

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields are given for illustration only and are not necessarily the maximum attainable;

(v) the structure of a compound of the Formula I of the invention was confirmed by nuclear magnetic resonance (NMR) and mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; q, quartet; m, multiplet; br, broad;

(vi) melting points are uncorrected and were determined using a Mettler SP62 automatic melting point apparatus or an oil-bath apparatus; and (vii) the following abbreviations have been used:—

BINAP (±)-2,2'-Bis(diphenylphosphino)-1,1'-binaphthalene
DMA N,N-dimethylacetamide
DMF N,N-dimethylformamide
DMSO dimethylsulphoxide
EDAC 1-(3-dimethylaminopropyl)-3-ethylcarbodiimide
HATU O-(7-Azabenzotriazol-1-yl)-N,N,N',N'-tetramethyluronium hexafluorophosphate
HOBT 1-hydroxybenzotriazole hydrate
THF tetrahydrofuran

EXAMPLE 1

N-Cyclopropyl-3-[7-[2-(dimethylamino)ethoxy]-1-oxoisoquinolin-2(1H)-yl]-4-methylbenzamide N-Cyclopropyl-3-(7-hydroxy-1-oxoisoquinolin-2(1H)-yl)-4-methylbenzamide (0.16 g), 2-dimethylaminoethyl chloride hydrochloride (87 mg), potassium carbonate (0.65 g), and sodium iodide (7 mg) were stirred in acetone (8 ml) at 60° C. for 16 hours. The reaction mixture was filtered, the solids washed with acetone, and the filtrate was concentrated. The residue was dissolved in ethyl acetate and washed with 2N NaOH solution, brine, dried (magnesium sulfate) and concentrated. Purification by column chromatography on a silica column eluting with 10% methanol/ethyl acetate+1% aqueous ammonia solution gave N-cyclopropyl-3-[7-[2-(dimethylamino)ethoxy]-1-oxoisoquinolin-2(1H)-yl]-4-methylbenzamide (0.137 g) as a white solid; NMR Spectrum: (DMSOd$_6$) 0.57 (m, 2H), 0.69 (m, 2H), 2.10 (s, 3H), 2.23 (s, 6H), 2.68 (t, 2H), 2.85 (m, 1H), 4.19 (m, 2H), 6.72 (d, 1H), 7.21 (d, 1H), 7.41 (d, 1H), 7.49 (d, 1H), 7.68 (s, 1H), 7.71 (d, 1H), 7.75 (s, 1H), 7.88 (d, 1H), 8.43 (d, 1H): Mass Spectrum: M+H$^+$ 406.

N-Cyclopropyl-3-(7-hydroxy-1-oxoisoquinolin-2(1H)-yl)-4-methylbenzamide used as starting material was prepared as follows:—

To a stirred solution of 4-methyl-3 nitrobenzoyl chloride (20 g) in methylene chloride (200 ml) at 0° C. was added a mixture of cyclopropylamine (7.62 ml) and triethylamine (28 ml). The mixture was allowed to warm to room temperature and stirred for a further 16 hours. The reaction mixture was evaporated in vacuo and a saturated NaHCO$_3$ solution was added. The precipitated solid was collected by filtration and washed with iso-hexane and dried (magnesium sulfate) to give N-cyclopropyl-4-methyl-3-nitrobenzamide as a colourless solid (22.9 g); NMR Spectrum: (DMSOd$_6$) 0.60 (m, 2H), 0.72 (m, 2H), 2.56 (s, 3H), 2.87 (m, 1H), 7.60 (d, 1H), 8.06 (m, 1H), 8.41 (d, 1H), 8.67 (d, 1H); Mass Spectrum: M+H$^+$ 221.

A suspension of N-cyclopropyl-4-methyl-3-nitrobenzamide (22.9 g) and 10% palladium on carbon (2 g) in ethanol (500 ml) was agitated under a hydrogen atmosphere for 16 hours. The reaction mixture was filtered through diatomaceous earth (Celite®) and the filtrate evaporated to dryness to give 3-amino-N-cyclopropyl-4-methylbenzamide as a colourless solid (17.1 g); NMR Spectrum: (DMSOd$_6$) 0.53 (m, 2H), 0.65 (m, 2H), 2.07 (s, 3H), 2.80 (m, 1H), 6.92 (m, 2H), 7.06 (d, 1H), 8.09 (d, 1H); Mass Spectrum: M+H$^+$ 191.

To a suspension of 2-(carboxymethyl)-5-methoxybenzoic acid (5.22 g) (synthesised using the procedure in Tetrahedron 1975, 31, 2607-19) in acetone (50 ml) was added acetyl chloride (7.06 ml) and the reaction mixture was stirred at room temperature for 18 hours. The solvent was evaporated and azeotroped with toluene (×3). The resultant solid was triturated with diethyl ether to yield 7-methoxy-1H-isochromene-1,3(4H)-dione as a brown solid (4.36 g); NMR Spectrum: (DMSOd$_6$) 3.84 (s, 3H), 4.20 (s, 2H), 7.36 (m, 2H), 7.50 (s, 1H).

A suspension of 7-methoxy-1H-isochromene-1,3(4H)-dione (1.09 g) and 3-amino-N-cyclopropyl-4-methylbenzamide (1.19 g) in a mixture of toluene (9 ml) and acetic acid (3 ml) was heated under microwave irradiation conditions (Personal Chemistry Emrys Optimizer with 300 W magnetron) at 150° C. for 90 minutes. This was repeated on three further batches and the separate batches combined, diluted with ethyl acetate and extracted with 2N HCl, water, brine, dried (magnesium sulfate) and left to crystallise for 18 hours. The solid was collected by filtration, washed with diethyl ether and air dried to yield :N-cyclopropyl-3-(7-methoxy-1,3-dioxo-3,4-dihydroisoquinolin-2(1H)-yl)-4-methylbenzamide as a yellow solid (6.27 g); NMR Spectrum: (DMSOd$_6$) 0.57 (m, 2H), 0.69 (m, 2H), 2.09 (s, 3H), 2.85 (m, 1H), 3.84 (s, 3H), 4.23 (d, 1H), 4.32 (d, 1H), 7.33 (d, 1H), 7.43 (m, 2H), 7.53 (s, 1H), 7.65 (s, 1H), 7.81 (d, 1H), 8.40 (d, 1H); Mass Spectrum: M+Na$^+$ 387.

To a solution of N-cyclopropyl-3-(7-methoxy-1,3-dioxo-3,4-dihydroisoquinolin-2(1H)-yl)-4-methylbenzamide (1 g) in Methanol (20 ml) and methylene chloride (45 ml) under an atmosphere of argon was added NaBH$_4$ (114 mg) portionwise and the reaction stirred at room temperature for 17 hours. Concentrated hydrochloric acid (0.2 ml) was added and the reaction stirred for a further 4 hours. The reaction mixture was concentrated and the resultant solid triturated with ethyl acetate and air dried to yield N-cyclopropyl-3-(7-methoxy-1-oxoisoquinolin-2(1H)-yl)-4-methylbenzamide as a white solid (849 mg); NMR Spectrum: (DMSOd$_6$) 0.56 (m, 2H), 0.69 (m, 2H), 2.10 (s, 3H), 2.86 (m, 1H), 3.39 (s, 3H), 6.72 (d, 1H), 7.21 (d, 1H), 7.41 (d, 1H), 7.50 (d, 1H), 7.67 (s, 1H), 7.71 (d, 1H), 7.89 (d, 1H), 8.44 (d, 1H); Mass Spectrum: M+H$^+$ 349.

A stirred suspension of N-cyclopropyl-3-(7-methoxy-1-oxoisoquinolin-2(1H)-yl)-4-methylbenzamide (845 mg) and lithium iodide (585 mg) in 2,4,6 collidine (10 ml) was heated under microwave irradiation conditions (Personal Chemistry Emrys Optimizer with 300 W magnetron) at 200° C. for 90 minutes. The mixture was dissolved using 2N NaOH and re-acidified using 2N HCl. The aqueous phase was extracted with ethyl acetate (×4) and the combined organic layers concentrated. The residue was triturated with 2N HCl and the solid collected by filtration, washed with diethyl ether and air dried to yield N-cyclopropyl-3-(7-hydroxy-1-oxoisoquinolin-2(1H)-yl)-4-methylbenzamide as a brown solid (562 mg); NMR Spectrum: (DMSOd$_6$) 0.55 (m, 2H), 0.69 (m, 2H), 2.10

(s, 3H), 2.85 (m, 1H), 6.66 (d, 1H), 7.11 (d, 1H), 7.24 (d, 1H), 7.49 (d, 1H), 7.60 (s, 1H), 7.61 (d, 1H), 7.73 (s, 1H), 7.88 (d, 1H), 8.43 (d, 1H), 10.00 (s, 1H); Mass Spectrum: M+Na⁺ 357.

EXAMPLE 2

Using an analogous procedure to that described in Example 1, N-cyclopropyl-3-(7-hydroxy-1-oxoisoquinolin-2(1H)-yl)-4-methylbenzamide was alkylated with the appropriate alkylating reagent to give the compounds described in Table 1.

TABLE 1

| R | Method | Note |
|---|---|---|
| 2-Piperidin-1-ylethoxy | Ex 1 | a |
| 2-Morpholin-4-ylethoxy | Ex 1 | b |
| 2-Pyrrolidin-1-ylethoxy | Ex 1 | c |
| 3-Dimethylaminopropoxy | Ex 1 | d |
| 2-(tert-Butylcarbamate)ethoxy | Ex 1 | e |

Notes
a The product gave the following data; NMR Spectrum: (DMSOd₆) 0.56 (m, 2 H), 0.69 (m, 2 H), 1.39 (m, 2 H), 1.50 (m, 4 H), 2.10 (s, 3 H), 2.45 (m, 4 H), 2.70 (t, 2 H), 2.86 (m, 1 H), 4.19 (m, 2 H), 6.72 (d, 1 H), 7.21 (d, 1 H), 7.41 (d, 1 H), 7.49 (d, 1 H), 7.69 (s, 1 H), 7.71 (d, 1 H), 7.77 (s, 1 H), 7.89 (d, 1 H), 8.43 (d, 1 H); Mass Spectrum: M + H⁺ 446.
b The product gave the following data; NMR Spectrum: (DMSOd₆) 0.56 (m, 2 H), 0.69 (m, 2 H), 2.10 (s, 3 H), 2.50 (m, 4 H), 2.74 (t, 2 H), 2.86 (m, 1 H), 3.59 (m, 4 H), 4.21 (m, 2 H), 6.71 (d, 1 H), 7.20 (d, 1 H), 7.41 (d, 1 H), 7.49 (d, 1 H), 7.69 (s, 1 H), 7.71 (d, 1 H), 7.74 (s, 1 H), 7.88 (d, 1 H), 8.43 (d, 1 H); Mass Spectrum: M + H⁺ 448.
c The product gave the following data; NMR Spectrum: (DMSOd₆) 0.56 (m, 2 H), 0.69 (m, 2 H), 1.69 (m, 4 H), 2.10 (s, 3 H), 2.55 (m, 4 H), 2.82-2.89 (m, 3 H), 4.19 (m, 2 H), 6.71 (d, 1 H), 7.21 (d, 1 H), 7.41 (d, 1 H), 7.49 (d, 1 H), 7.67 (s, 1 H), 7.71 (d, 1 H), 7.73 (s, 1 H), 7.88 (d, 1 H), 8.42 (d, 1 H); Mass Spectrum: M + H⁺ 432.
d The product gave the following data; NMR Spectrum: (DMSOd₆) 0.56 (m, 2 H), 0.69 (m, 2 H), 1.89 (m, 2 H), 2.10 (s, 3 H), 2.14 (s, 6 H), 2.38 (t, 2 H), 2.85 (m, 1 H), 4.11 (t, 2 H), 6.71 (d, 1 H), 7.21 (d, 1 H), 7.40 (d, 1 H), 7.49 (d, 1 H), 7.65 (s, 1 H), 7.70 (d, 1 H), 7.74 (s, 1 H), 7.88 (d, 1 H), 8.44 (d, 1 H); Mass Spectrum: M + Na⁺ 420.
e The product gave the following data; NMR Spectrum: (DMSOd₆) 0.56 (m, 2 H), 0.69 (m, 2 H), 1.38 (s, 9 H), 2.10 (s, 3 H), 2.86 (m, 1 H), 3.34 (m, 2 H), 4.10 (m, 2 H), 6.73 (d, 1 H), 7.05 (t, 1 H), 7.23 (d, 1 H), 7.41 (m, 1 H), 7.50 (d, 1 H), 7.65 (d, 1 H), 7.74 (m, 2 H), 7.87 (m, 1 H), 8.46 (d, 1 H); Mass Spectrum: M − Boc⁺ 378.

EXAMPLE 3

N-Cyclopropyl-4-methyl-3-[7-[2-(1,4-oxazepan-4-yl)ethoxy]-1-oxoisoquinolin-2(1H)-yl]benzamide 3-[7-(2-Chloroethoxy)-1-oxoisoquinolin-2(1H)-yl]-N-cyclopropyl-4-methylbenzamide (0.15 g), potassium iodide (0.13 g), 1,4-oxazepane hydrochloride (0.34 g), and N,N'-diisopropylethylamine (0.8 ml) were stirred in DMA (3 ml) and heated under microwave irradiation conditions (Personal Chemistry Emrys Optimizer with 300 W magnetron) at 150° C. for 1 hour. The reaction mixture was diluted with ethyl acetate and washed with water (×5), brine (×2), dried (magnesium sulfate) and concentrated. Purification by column chromatography on a silica column eluting using a gradient of ethyl acetate to 15% methanol/ethyl acetate gave N-cyclopropyl-4-methyl-3-[7-[2-(1,4-oxazepan-4-yl)ethoxy]-1-oxoisoquinolin-2(1H)-yl]benzamide (0.114 g) as a white solid; NMR Spectrum: (DMSOd₆) 0.56 (m, 2H), 0.69 (m, 2H), 1.80 (m, 2H), 2.10 (s, 3H), 2.76 (m, 4H), 2.85 (m, 1H), 2.92 (t, 2H), 3.61 (m, 2H), 3.66 (t, 2H), 4.19 (m, 2H), 6.72 (d, 1H), 7.21 (d, 1H), 7.41 (d, 1H), 7.49 (d, 1H), 7.69 (s, 1H), 7.71 (d, 1H), 7.74 (s, 1H), 7.88 (d, 1H), 8.43 (d, 1H); Mass Spectrum: M+H⁺ 462.

The 3-[7-(2-chloroethoxy)-1-oxoisoquinolin-2(1H)-yl]-N-cyclopropyl-4-methylbenzamide used as starting material was prepared as follows:—

N-Cyclopropyl-3-(7-hydroxy-1-oxoisoquinolin-2(1H)-yl)-4-methylbenzamide (0.56 g), 1-bromo-2-chloroethane (0.7 ml) and potassium carbonate (2.32 g) were stirred in DMF (20 ml) at 50° C. for 18 hours. The reaction mixture was diluted with ethyl acetate and washed with water (×5), brine (×2), dried (magnesium sulfate) and concentrated to give 3-[7-(2-chloroethoxy)-1-oxoisoquinolin-2(1H)-yl]-N-cyclopropyl-4-methylbenzamide as a cream coloured solid (0.57 g); NMR Spectrum: (DMSOd₆) 0.56 (m, 2H), 0.69 (m, 2H), 2.10 (s, 3H), 2.86 (m, 1H), 4.00 (t, 2H), 4.40 (m, 2H), 6.73 (d, 1H), 7.23 (d, 1H), 7.47 (d, 1H), 7.49 (d, 1H), 7.68 (s, 1H), 7.73 (m, 2H), 7.88 (d, 1H), 8.44 (d, 1H); Mass Spectrum: M+Na⁺ 419.

EXAMPLE 4

Using an analogous procedure to that described in Example 3, 3-[7-(2-chloroethoxy)-1-oxoisoquinolin-2(1H)-yl]-N-cyclopropyl-4-methylbenzamide was reacted with the appropriate amine to give the compounds described in Table 2.

TABLE 2

| R | Method | Note |
|---|---|---|
| (3R)-3-Fluoropyrrolidin-1-yl | Ex 3 | a |
| (2-Methoxyethyl)(methyl)amino | Ex 3 | b |
| Cyclobutylmethyl(methyl)amino | Ex 3 | c |
| (2S)-2-(Methoxymethyl)pyrrolidin-1-yl | Ex 3 | d |
| Isopropyl(methyl)amino | Ex 3 | e |
| Isopropyl(2-methoxyethyl)amino | Ex 3 | f |
| (3R)-3-Hydroxypyrrolidin-1-yl | Ex 3 | g |
| Methyl(tetrahydro-2H-pyran-4-yl)amino | Ex 3 | h |
| Methyl(tetrahydrofuran-2-ylmethyl)amino | Ex 3 | i |
| Methyl(prop-2-yn-1-yl)amino | Ex 3 | j |
| 4,4-Difluoropiperidin-1-yl | Ex 3 | k |
| 3,3-Difluoropyrrolidin-1-yl | Ex 3 | l |
| 4-Fluoropiperidin-1-yl | Ex 3 | m |
| 3-Fluoropiperidin-1-yl | Ex 3 | n |
| 2,6-Dimethylmorpholin-4-yl] (mixture of trans isomers) | Ex 3 | o |
| (2R,6S)-2,6-Dimethylmorpholin-4-yl | Ex 3 | p |
| (3S)-3-Fluoropyrrolidin-1-yl | Ex 3 | q |
| 4-(Methylsulfonyl)piperazin-1-yl | Ex 3 | r |
| Cyclohexyl(isopropyl)amino | Ex 3 | s |
| Cyclohexyl(ethyl)amino | Ex 3 | t |
| Isobutyl(methyl)amino | Ex 3 | u |
| Ethyl(methyl) amino | Ex 3 | v |
| Diethylamino | Ex 3 | w |
| tert-Butyl(methyl)amino | Ex 3 | x |
| Cyclohexyl(methyl)amino | Ex 3 | y |
| Diisopropylamino | Ex 3 | z |
| Isopropyl(ethyl)amino | Ex 3 | aa |
| (2S)-2-Methylpiperidin-1-yl | Ex 3 | bb |
| 2-(Hydroxymethyl)morpholin-4-yl | Ex 3 | cc |
| (2S)-2-(Hydroxymethyl)piperidin-1-yl | Ex 3 | dd |

TABLE 2-continued

| R | Method | Note |
|---|---|---|
| Isopropylamino | Ex 3 | ee |
| Methylamino | Ex 3 | ff |

Notes a The product gave the following data; NMR Spectrum: (DMSOd₆) 0.56 (m, 2 H), 0.69 (m, 2 H), 1.79-1.95 (m, 1 H), 2.10 (s, 3 H), 2.10-2.20 (m, 1 H), 2.40-2.47 (m, 1 H), 2.64-2.78 (m, 1 H), 2.83-2.98 (m, 5 H), 4.20 (m, 2 H), 5.11-5.29 (m, 1 H), 6.72 (d, 1 H), 7.20 (d, 1 H), 7.40 (d, 1 H), 7.49 (d, 1 H), 7.65 (s, 1 H), 7.71 (d, 1 H), 7.75 (d, 1 H), 7.88 (d, 1 H), 8.42 (d, 1 H); Mass Spectrum: M + H⁺ 450.

b The product gave the following data; NMR Spectrum: (DMSOd₆) 0.56 (m, 2 H), 0.69 (m, 2 H), 2.10 (s, 3 H), 2.30 (s, 3 H), 2.60 (t, 2 H), 2.80 (t, 2 H), 2.85 (m, 1 H), 3.21 (s, 3 H), 3.41 (t, 2 H), 4.17 (t, 2 H), 6.71 (d, 1 H), 7.40 (d, 1 H), 7.49 (d, 1 H), 7.67 (s, 1 H), 7.71 (d, 1 H), 7.74 (d, 1 H), 7.88 (d, 1 H), 8.42 (d, 1 H); Mass Spectrum: M + H⁺ 450.

c The product gave the following data; NMR Spectrum: (DMSOd₆) 0.55 (m, 2 H), 0.69 (m, 2 H), 1.62 (m, 2 H), 1.73-1.89 (m, 2 H), 1.98 (m, 2 H), 2.10 (s, 3 H), 2.21 (s, 3 H), 2.44 (m, 3 H), 2.72 (t, 2 H), 2.86 (m, 1 H), 4.15 (m, 2 H), 6.71 (d, 1 H), 7.20 (d, 1 H), 7.40 (d, 1 H), 7.49 (d, 1 H), 7.68 (s, 1 H), 7.70 (d, 1 H), 7.73 (s, 1 H), 7.88 (d, 1 H), 8.42 (d, 1 H); Mass Spectrum: M + H⁺ 460.

d The product gave the following data; NMR Spectrum: (DMSOd₆) 0.55 (m, 2 H), 0.69 (m, 2 H), 1.46 (m, 1 H), 1.81 (m, 1 H), 2.10 (s, 3 H), 2.33 (m, 1 H), 2.66-2.78 (m, 2 H), 2.85 (m, 1 H), 3.11 (m, 1 H), 3.17-3.37 (m, 4 H), 3.22 (s, 3 H), 4.15 (m, 2 H), 6.72 (d, 1 H), 7.20 (d, 1 H), 7.40 (d, 1 H), 7.59 (d, 1 H), 7.68 (s, 1 H), 7.70 (d, 1 H), 7.73 (s, 1 H), 7.88 (d, 1 H), 8.42 (d, 1 H); Mass Spectrum: M + H⁺ 476.

e The product gave the following data; NMR Spectrum: (DMSOd₆) 0.55 (m, 2 H), 0.69 (m, 2 H), 0.98 (d, 6 H), 2.10 (s, 3 H), 2.23 (m, 1 H), 2.76 (t, 1 H), 2.85 (m, 1 H), 4.12 (m, 2 H), 6.71 (d, 1 H), 7.20 (d, 1 H), 7.39 (d, 1 H), 7.49 (d, 1 H), 7.65 (s, 1 H), 7.70 (d, 1 H), 7.74 (s, 1 H), 7.88 (d, 1 H), 8.43 (d, 1 H); Mass Spectrum: M + H⁺ 434.

f The product gave the following data; NMR Spectrum: (DMSOd₆) 0.55 (m, 2 H), 0.68 (m, 2 H), 0.97 (d, 6 H), 2.10 (s, 3 H), 2.63 (t, 2 H), 2.83 (s, 3 H), 2.95 (m, 1 H), 3.22 (s, 3 H), 3.35 (t, 2 H), 4.07 (t, 2 H), 6.71 (d, 1 H), 7.20 (d, 1 H), 7.39 (d, 1 H), 7.49 (d, 1 H), 7.66 (s, 1 H), 7.70 (d, 1 H), 7.74 (s, 1 H), 7.88 (d, 1 H), 8.42 (d, 1 H); Mass Spectrum: M + H⁺ 478.

g The product gave the following data; NMR Spectrum: (DMSOd₆) 0.56 (m, 2 H), 0.69 (m, 2 H), 1.53 (m, 1 H), 1.98 (m, 1 H), 2.10 (s, 3 H), 2.42 (m, 1 H), 2.52 (m, 1 H), 2.67 (m, 1 H), 2.77-2.89 (m, 4 H), 4.18 (m, 3 H), 4.65 (d, 1 H), 6.71 (d, 1 H), 7.20 (d, 1 H), 7.40 (d, 1 H), 7.49 (d, 1 H), 7.67 (s, 1 H), 7.70 (d, 1 H), 7.74 (s, 1 H), 7.88 (d, 1 H), 8.43 (d, 1 H); Mass Spectrum: M + H⁺ 448.

h The product gave the following data; NMR Spectrum: (CDCl₃) 0.58 (m, 2 H), 0.82 (m, 2 H), 1.63 (m, 2 H), 1.76 (m, 2 H), 2.20 (s, 3 H), 2.41 (s, 3 H), 2.67 (m, 1 H), 2.85 (m, 1 H), 2.96 (t, 2 H), 3.39 (m, 2 H), 4.03 (m, 2 H), 4.19 (t, 2 H), 6.44 (m, 1 H), 6.50 (m, 1 H), 6.85 (m 1 H), 7.30 (m, 1 H), 7.39 (m, 1 H), 7.48 (m, 1 H), 7.61 (m, 1 H), 7.75 (m, 1 H), 7.81 (m, 1 H); Mass Spectrum: M + H⁺ 476.

i The product gave the following data; NMR Spectrum: (CDCl₃) 0.58 (m, 2 H), 0.81 (m, 2 H), 1.53 (m, 1 H), 1.85 (m, 2 H), 1.99 (m, 1 H), 2.32 (s, 3 H), 2.45 (s, 3 H), 2.60 (cm, 2 H), 2.85 (m, 1 H), 2.97 (m, 2 H), 3.72 (m, 1 H), 3.87 (m, 1 H), 4.08 (m, 1 H), 4.2 (m, 2 H), 6.49 (m, 2 H), 6.85 (m, 1 H), 7.31 (m, 1 H), 7.385 (m, 1 H), 7.44 (m, 1 H), 7.6 (m, 1 H), 7.78 (m, 2 H); Mass Spectrum: M + H⁺ 476.

j The product gave the following data; NMR Spectrum: (CDCl₃) 0.57 (m, 2 H), 0.80 (m, 2 H), 2.18 (s, 3 H), 2.26 (s, 1 H), 2.43 (s, 3 H), 2.82 (m, 1 H), 2.94 (m, 2 H), 3.48 (s, 2 H), 4.19 (m, 2 H), 6.49 (m, 2 H), 6.85 (m, 1 H), 7.33 (m, 1 H), 7.38 (m, 1 H), 7.46 (m, 1 H), 7.78 (m, 1 H); Mass Spectrum: M + H⁺ 430.

k The product gave the following data; NMR Spectrum: (CDCl₃) 0.55 (m, 2 H), 0.82 (m, 2 H), 2.02 (m, 4 H), 2.19 (s, 3 H), 2.72 (m, 4 H), 2.84 (m, 1 H), 2.90 (m, 1 H), 4.23 (m, 2 H), 6.42 (m, 1 H), 6.50 (m, 1 H), 6.87 (m, 1 H), 7.30 (m, 1 H), 7.38 (m, 1 H), 7.48 (m, 1 H), 7.62 (m, 1 H), 7.74 (m, 1 H), 7.81 (m, 1 H); Mass Spectrum: M + H⁺ 482.

l The product gave the following data; NMR Spectrum: (CDCl₃) 0.57 (m, 2 H), 0.81 (m, 2 H), 2.19 (s, 3 H), 2.30 (m, 2 H), 2.83 (cm, 3 H), 2.95 (m, 3 H), 3.07 (m, 2 H), 4.20 (m, 2 H), 6.49 (m, 2 H), 6.86 (m, 1 H), 7.3 (m, 1 H), 7.38 (m, 1 H), 7.46 (m, 1 H), 7.60 (m, 1 H), 7.75 (m, 2 H); Mass Spectrum: M + H⁺ 468.

m The product gave the following data; NMR Spectrum: (CDCl₃) 0.56 (m, 2 H), 0.80 (m, 2 H), 1.90 (cm, 4 H), 2.19 (s, 3 H), 2.52 (m, 2 H), 2.71 (m, 2 H), 2.85 (m, 3 H), 4.22 (m, 2 H), 4.69 (m, 1 H), 6.45 (m, 2 H), 6.85 (m, 1 H), 7.3 (m, 1 H), 7.38 (m, 1 H), 7.46 (m, 1 H), 7.60 (m, 1 H), 7.75 (m, 1 H), 7.80 (m, 1 H); Mass Spectrum: M + H⁺ 464.

n The product gave the following data; NMR Spectrum: (CDCl₃) 0.57 (m, 2 H), 0.80 (m, 2 H), 1.60 (m, 2 H), 1.85 (m, 2 H), 2.19 (s, 3 H), 2.43 (m, 2 H), 2.61 (m, 2 H), 2.83 (m, 1 H), 2.90 (cm, 4 H), 4.23 (m, 2 H), 4.63 (m, 1 H), 6.47 (m, 1 H), 6.84 (m, 1 H), 7.30 (m, 1 H), 7.38 (m, 1 H), 7.45 (m, 1 H), 7.60 (m, 1 H), 7.75 (m, 1 H); Mass Spectrum: M + H⁺ 464.

o The product gave the following data; NMR Spectrum: (CDCl₃) 0.56 (m, 2 H), 0.81 (m, 2 H), 1.21 (m, 7 H), 2.18 (s, 3 H), 2.25 (m, 2 H), 2.58 (m, 2 H), 2.78 (m, 3 H), 3.99 (m, 2 H), 4.19 (m, 2 H), 6.31 (m, 1 H), 6.51 (m, 1 H), 6.86 (m, 1 H), 7.3 (m, 1 H), 7.38 (m, 1 H), 7.48 (m, 1 H), 7.58 (m, 1 H), 7.72 (m, 1 H), 7.80 (m, 1 H); Mass Spectrum: M + H⁺ 476.

p The product gave the following data; NMR Spectrum: (CDCl₃) 0.55 (m, 2 H), 0.80 (m, 2 H), 1.14 (m, 6 H), 1.88 (m, 2 H), 2.17 (s, 3 H), 2.82 (m, 5 H), 3.70 (m, 2 H), 4.20 (m, 2 H), 6.40 (m, 1 H), 6.48 (m, 1 H), 6.84 (m, 1 H), 7.30 (m, 1 H), 7.366 (m, 1 H), 7.46 (m, 1 H), 7.59 (m, 1 H), 7.73 (m, 1 H), 7.80 (m, 1 H); Mass Spectrum: M + H⁺ 476.

q The product gave the following data; NMR Spectrum: (DMSOd₆) 0.56 (m, 2 H), 0.69 (m, 2 H), 1.79-1.95 (m, 1 H), 2.10 (s, 3 H), 2.10-2.20 (m, 1 H), 2.40-2.47 (m, 1 H), 2.64-2.78 (m, 1 H), 2.83-2.98 (m, 5 H), 4.20 (m, 2 H), 5.11-5.29 (m, 1 H), 6.72 (d, 1 H), 7.20 (d, 1 H), 7.40 (d, 1 H), 7.49 (d, 1 H), 7.65 (s, 1 H), 7.71 (d, 1 H), 7.75 (d, 1 H), 7.88 (d, 1 H), 8.42 (d, 1 H); Mass Spectrum: M + H⁺ 450.

r The product gave the following data; NMR Spectrum: (CDCl₃) 0.51 (m, 2 H), 0.76 (m, 2 H), 2.12 (s, 3 H), 2.65 (t, 4 H), 2.70 (s, 2 H), 2.79 (m, 1 H), 2.84 (m, 1 H), 3.20 (t, 4 H), 4.16 (t, 2 H), 6.30 (s, 1 H), 6.45 (m, 1 H), 6.81 (m, 1 H), 7.24 (m, 1 H), 7.32 (d, 1 H), 7.42 (d, 1 H), 7.54 (d, 1 H), 7.67 (d, 1 H), 7.76 (d, 1 H); Mass Spectrum: M + H⁺ 525.

s The product gave the following data; NMR Spectrum: (CDCl₃) d 0.51 (m, 2 H), 0.76 (m, 2 H), 1.10 (m, 10 H), 1.53 (m, 2 H), 1.71 (m, 3 H), 2.12 (s, 3 H), 2.49 (m, 1 H), 2.83 (m, 3 H), 3.05 (m, 1 H), 3.95 (m, 2 H), 6.41 (m, 2 H), 6.79 (m, 1 H), 7.20 (m, 2 H), 7.33 (m, 1 H), 7.40 (m, 1 H), 7.54 (m, 1 H), 7.72 (m, 2 H); Mass Spectrum: M + H⁺ 502.

t The product gave the following data; NMR Spectrum: (CDCl₃) 0.53 (m, 2 H), 0.75 (m, 2 H), 1.11 (m, 8 H), 1.66 (m, 5 H), 2.14 (s, 3 H), 2.49 (m, 1 H), 2.62 (m, 2 H), 2.83 (m, 3 H), 4.04 (t, 2 H), 6.43 (m, 2 H), 6.79 (m, 1 H), 7.23 (m, 1 H), 7.33 (m, 1 H), 7.40 (m, 1 H), 7.56 (m, 1 H), 7.73 (m, 2 H); Mass Spectrum: M + H⁺ 488.

u The product gave the following data; NMR Spectrum: (CDCl₃) 0.49 (m, 2 H), 0.73 (m, 2 H), 0.84 (d, 6 H), 1.71 (m, 1 H), 2.13 (m, 5 H), 2.27 (s, 3 H), 2.76 (m, 3 H), 4.11 (t, 2 H), 6.40 (m, 1 H), 6.46 (s, 1 H), 6.76 (m, 1 H), 7.22 (m, 1 H), 7.30 (d, 1 H), 7.37 (d, 1 H), 7.54 (m, 1 H), 7.70 (m, 2 H); Mass Spectrum: M + H⁺ 448.

v The product gave the following data; NMR Spectrum: (CDCl₃) 0.49 (m, 2 H), 0.73 (m, 2 H), 1.04 (t, 3 H), 2.11 (s, 3 H), 2.30 (s, 3 H), 2.50 (q, 2 H), 2.77 (m, 3 H), 4.13 (t, 2 H), 6.41 (m, 2 H), 6.77 (m, 1 H), 7.25 (m, 1 H), 7.31 (d, 1 H), 7.38 (d, 1 H), 7.53 (d, 1 H), 7.70 (m, 2 H); Mass Spectrum: M + H⁺ 420.

w The product gave the following data; NMR Spectrum: (CDCl₃) 0.49 (m, 2 H), 0.73 (m, 2 H), 1.02 (t, 6 H), 2.11 (s, 3 H), 2.59 (q, 4 H), 2.76 (m, 1 H), 2.87 (t, 2 H), 4.10 (t, 2 H), 6.39 (m, 1 H), 6.47 (s, 1 H), 6.77 (m, 1 H), 7.23 (m, 1 H), 7.30 (d, 1 H), 7.37 (d, 1 H), 7.53 (d, 1 H), 7.70 (m, 2 H); Mass Spectrum: M + H⁺ 434.

x The product gave the following data; NMR Spectrum: (CDCl₃) 0.47 (m, 2 H), 0.70 (m, 2 H), 1.04 (s, 9 H), 2.29 (s, 3 H), 2.29 (s, 3 H), 2.75 (m, 3 H), 4.07 (t, 2 H), 6.38 (m, 1 H), 6.51 (s, 1 H), 6.75 (m, 1 H), 7.20 (q, 1 H), 7.30 (m, 1 H), 7.35 (m, 1 H), 7.53 (d, 1 H), 7.71 (m, 2 H); Mass Spectrum: M + H⁺ 448.

y The product gave the following data; NMR Spectrum: (CDCl₃) 0.48 (m, 2 H), 0.70 (m, 2 H), 1.11 (m, 5 H), 1.56 (m, 1 H), 1.76 (m, 4 H), 2.10 (s, 3 H), 2.35 (m, 4 H), 2.74 (m, 1 H), 2.85 (t, 2 H), 4.08 (t, 2 H), 6.37 (m, 1 H), 6.53 (m, 1 H), 6.75 (m, 1 H), 7.21 (m, 1 H), 7.32 (m, 2 H), 7.53 (m, 1 H), 7.70 (m, 2 H); Mass Spectrum: M + H⁺ 474.

z The product gave the following data; NMR Spectrum: (CDCl₃) 0.49 (m, 2 H), 0.73 (m, 2 H), 0.98 (d, 12 H), 2.11 (s, 3 H), 2.77 (m, 3 H), 2.99 (m, 2 H), 3.95 (t, 2 H), 6.41 (m, 2 H), 6.76 (m, 1 H), 7.19 (m, 1 H), 7.31 (d, 1 H), 7.36 (d, 1 H), 7.53 (m, 1 H), 7.70 (m, 2 H); Mass Spectrum: M + H⁺ 462.

aa The product gave the following data; NMR Spectrum: (CDCl₃) 0.49 (m, 2 H), 0.72 (m, 2 H), 1.00 (m, 9 H), 2.11 (s, 3 H), 2.54 (q, 2 H), 2.79 (m, 3 H), 2.97 (m, 1 H), 4.04 (t, 2 H), 6.39 (m, 1 H), 6.46 (s, 1 H), 6.76 (m, 1 H), 7.21 (m, 1 H), 7.3 (d, 1 H), 7.36 (d, 1 H), 7.52 (d, 1 H), 7.69 (m, 2 H); Mass Spectrum: M + H⁺ 448.

bb The product gave the following data; NMR Spectrum: (CDCl₃) 0.49 (m, 2 H), 0.73 (m, 2 H), 1.08 (d, 3 H), 1.25 (m, 2 H), 1.61 (m, 4 H), 2.15 (s, 3 H), 2.37 (m, 2 H), 2.83 (m, 3 H), 3.09 (m, 1 H), 4.14 (t, 2 H), 6.43 (m, 2 H), 6.77 (m, 1 H), 7.21 (m, 1 H), 7.30 (d, 1 H), 7.37 (d, 1 H), 7.54 (d, 1 H), 7.70 (m, 2 H); Mass Spectrum: M + H⁺ 460.

cc The product gave the following data; NMR Spectrum: (CDCl₃) 0.49 (m, 2 H), 0.72 (m, 2 H), 1.74 (q, 1 H), 2.09 (q, 4 H), 2.26 (q, 1 H), 2.78 (m, 5 H), 3.58 (m, 4 H), 3.84 (m, 1 H), 4.16 (t, 2 H), 6.41 (m, 1 H), 6.57 (s, 1 H), 6.77 (m, 1 H), 7.23 (m, 1 H), 7.30 (d, 1 H), 7.38 (d, 1 H), 7.54 (d, 1 H), 7.70 (m, 2 H); Mass Spectrum: M + H⁺ 478.

dd The product gave the following data; NMR Spectrum: (DMSOd₆) 0.48 (m, 2 H), 0.72 (m, 2 H), 1.35 (m, 10 H), 2.10 (s, 3 H), 2.40 (m, 1 H), 2.73 (m, 1 H), 2.88 (m, 1 H), 3.10 (m, 2 H), 4.16 (m, 2 H), 6.38 (m, 1 H), 6.61 (m, 1 H), 6.76 (m, 1 H), 7.20 (m, 1 H), 7.29 (d, 1 H), 7.35 (d, 1 H), 7.53 (d, 1 H), 7.71 (m, 2 H); Mass Spectrum: M + H⁺ 488.

ee The product gave the following data; NMR Spectrum: (DMSOd₆) 0.56 (m, 2 H), 0.69 (m, 2 H), 1.01 (d, 6 H), 2.11 (s, 3 H), 2.79 (m, 1 H), 2.86 (m, 1 H), 2.92 (m, 2 H), 4.12 (m, 2 H), 6.73 (d, 1 H), 7.21 (d, 1 H), 7.43 (m, 1 H), 7.50 (d, 1 H), 7.67 (d, 1 H), 7.71 (s, 1 H), 7.73 (s, 1 H), 7.76 (d, 1 H), 7.87 (d, 1 H), 8.43 (d, 1 H); Mass Spectrum: M + H⁺ 420.

ff The product gave the following data; NMR Spectrum: (DMSOd₆) 0.56 (m, 2 H), 0.69 (m, 2 H), 2.10 (s, 3 H), 2.35 (s, 3 H), 2.82-2.89 (m, 3 H), 4.13 (m, 2 H), 6.73 (d, 1 H), 7.22 (d, 1 H), 7.42 (m, 1 H), 7.50 (d, 1 H), 7.66 (s, 1 H), 7.72 (d, 1 H), 7.76 (s, 1 H), 7.87 (d, 1 H), 8.46 (d, 1 H); Mass Spectrum: M + H⁺ 392.

EXAMPLE 5

3-(7-Bromo-1-oxoisoquinolin-2(1H)-yl)-N-cyclopropyl-4-methylbenzamide

To a solution of 3-(7-bromo-1,3-dioxo-3,4-dihydroisoquinolin-2(1H)-yl)-N-cyclopropyl-4-methylbenzamide (1.13 g) in methanol (19 ml) and methylene chloride (45 ml) under an atmosphere of argon was added NaBH₄ (114 mg) portionwise and the reaction stirred at room temperature for 17 hours. Concentrated hydrochloric acid (0.2 ml) was added and the reaction stirred for a further 1 hour. The reaction mixture was concentrated and the residue resuspended in methylene chloride, washed 2N HCl, dried (magnesium sulfate) and concentrated to give 3-(7-bromo-1-oxoisoquinolin-2(1H)-yl)-N-cyclopropyl-4-methylbenzamide as a brown solid (157 mg); NMR Spectrum: (DMSOd₆) 0.55 (m, 2H), 0.70 (m, 2H), 2.10 (s, 3H), 2.85 (m, 1H), 6.80 (d, 1H), 7.42 (d, 1H), 7.51 (d, 1H), 7.78 (d, 1H), 7.79 (s, 1H), 7.89 (d, 1H), 7.97 (d, 1H), 8.35 (s, 1H), 8.44 (d, 1H); Mass Spectrum: M+H⁺ 421.

3-(7-Bromo-1,3-dioxo-3,4-dihydroisoquinolin-2(1H)-yl)-N-cyclopropyl-4-methylbenzamide used as starting material was prepared as follows:—

Sodium hydride (1.2 g) was added portionwise to a stirred suspension of 2-bromo-5-methoxybenzoic acid (3.50 g) and copper (I) bromide (100 mg) in ethylacetoacetate (15 ml). After the addition was complete the reaction was stirred under an argon atmosphere at 80° C. for 30 minutes. The reaction mixture was cooled to room temperature and poured into water (100 ml) and extracted with diethyl ether (×2). To the aqueous layer was added NaOH (10 g) and the solution stirred at room temperature for 18 hours. The solution was washed with methylene chloride and the pH adjusted to pH 1 with concentrated hydrochloric acid and extracted with methylene chloride. The combined organic layers were dried (magnesium sulfate) and concentrated to a brown solid. The solid was triturated with ethyl acetate to yield 2-(carboxymethyl)-5-bromobenzoic acid as a brown solid (2.38 g); NMR Spectrum: (DMSOd$_6$) 3.98 (s, 2H), 7.37 (d, 1H), 7.76 (d, 1H), 8.04 (s, 1H); Mass Spectrum: M+Na$^+$ 281.

To a suspension of 2-(carboxymethyl)-5-bromobenzoic acid (2.37 g) in acetone (20 ml) was added acetyl chloride (2.60 ml) and the reaction mixture was stirred at room temperature for 18 hours. The solvent was evaporated and azeotroped with toluene (×3). The resultant solid was triturated with diethyl ether to yield 7-bromo-1H-isochromene-1,3(4H)-dione as a brown solid (2.20 g); NMR Spectrum: (DMSOd$_6$) 4.24 (s, 2H), 7.42 (d, 1H), 7.94 (d, 1H), 8.13 (s, 1H).

A suspension of 7-bromo-1H-isochromene-1,3(4H)-dione (1.09 g) and 3-amino-N-cyclopropyl-4-methylbenzamide (0.91 g) in a mixture of toluene (8 ml) and acetic acid (2.5 ml) was heated under microwave irradiation conditions (Personal Chemistry Emrys Optimizer with 300 W magnetron) at 150° C. for 60 minutes. This was process was repeated and the batches combined, diluted with ethyl acetate and washed with 1N HCl, saturated NaHCO$_3$ solution, water, brine, dried (magnesium sulfate) to yield 3-(7-bromo-1,3-dioxo-3,4-dihydroisoquinolin-2(1H)-yl)-N-cyclopropyl-4-methylbenzamide as a brown solid (1.13 g); NMR Spectrum: (DMSOd$_6$) 0.60 (m, 2H), 0.71 (m, 2H), 2.12 (s, 3H), 2.89 (m, 1H), 4.34 (d, 1H), 4.42 (d, 1H), 7.48 (d, 1H), 7.53 (d, 1H), 7.70 (s, 1H), 7.85 (d, 1H), 7.99 (d, 1H), 8.20 (s, 1H), 8.45 (d, 1H); Mass Spectrum: M+Na$^+$ 435.

EXAMPLE 6

3-(1-Oxoisoquinolin-2(1H)-yl)-N-cyclopropyl-4-methylbenzamide

To a solution of 3-(1,3-dioxo-3,4-dihydroisoquinolin-2(1H)-yl)-N-cyclopropyl-4-methylbenzamide (385 mg) in methanol (8 ml) and methylene chloride (19 ml) under an atmosphere of argon was added NaBH$_4$ (48 mg) portionwise and the reaction stirred at room temperature for 17 hours. Concentrated hydrochloric acid (0.1 ml) was added and the reaction stirred for a further 30 minutes. The reaction mixture was concentrated and the residue resuspended in ethyl acetate, washed 1N NaOH, water, brine, dried (magnesium sulfate) and concentrated to give a white solid which was purified by column chromatography with a gradient of iso-hexane to 80% ethylacetate/iso-hexane to give 3-(1-Oxoisoquinolin-2(1H)-yl)-N-cyclopropyl-4-methylbenzamide as a white solid (190 mg); NMR Spectrum: (DMSOd$_6$) 0.56 (m, 2H), 0.69 (m, 2H), 2.10 (s, 3H), 2.85 (m, 1H), 6.75 (d, 1H), 7.34 (d, 1H), 7.49 (d, 1H), 7.58 (m, 1H), 7.75-7.82 (m, 3H), 7.88 (d, 1H), 8.26 (d, 1H), 8.43 (d, 1H); Mass Spectrum: M+H$^+$ 319.

3-(1,3-Dioxo-3,4-dihydroisoquinolin-2(1H)-yl)-N-cyclopropyl-4-methylbenzamide used as starting material was prepared as follows:—

A suspension of 1H-isochromene-1,3(4H)-dione (400 mg) and 3-amino-N-cyclopropyl-4-methylbenzamide (514 mg) in toluene (3 ml) was heated under microwave irradiation conditions (Personal Chemistry Emrys Optimizer with 300 W magnetron) at 150° C. for 60 minutes. The reaction mixture was diluted with ethyl acetate and washed with 2N HCl, water, brine, dried (magnesium sulfate) and concentrated to a foam which was purified by column chromatography with a gradient of iso-hexane to 70% ethyl acetate/iso-hexane to yield 3-(1,3-dioxo-3,4-dihydroisoquinolin-2(1H)-yl)-N-cyclopropyl-4-methylbenzamide as a solid (464 mg); NMR Spectrum: (DMSOd$_6$) 0.56 (m, 2H), 0.69 (m, 2H), 2.09 (s, 3H), 2.85 (m, 1H), 4.33 (d, 1H), 4.41 (d, 1H), 7.42 (d, 1H), 7.49-7.55 (m, 2H), 7.65 (s, 1H), 7.74 (t, 1H), 7.80 (d, 1H), 8.09 (d, 1H), 8.39 (d, 1H); Mass Spectrum: M+H$^+$ 335.

EXAMPLE 7

3-[7-[2-(Dimethylamino)ethoxy]-1-oxoisoquinolin-2(1H)-yl]-N-isoxazol-3-yl-4-methylbenzamide To a stirred solution of 3-[7-[2-(dimethylamino)ethoxy]-1-oxoisoquinolin-2(1H)-yl]-4-methylbenzoic acid (232 mg) in methylene chloride (5 ml) was added thionyl chloride (231 µl) and the solution heated to 40° C. for 40 minutes. The reaction mixture was concentrated and azeotroped with toluene (×2). The residue was dissolved in methylene chloride (2 ml) and 3-aminoisoxazole (94 µl) added and the reaction mixture stirred for 18 hours. The reaction was diluted with ethyl acetate, washed 1N NaOH, water, brine, dried (magnesium sulfate) and concentrated to a brown oil which was purified by column chromatography with a gradient of 10% methanol in methylene chloride to 10% methanol/methylene chloride+1% aqueous ammonia solution to yield an orange oil which was recrystallised from ethyl acetate to give 3-[7-[2-(dimethylamino)ethoxy]-1-oxoisoquinolin-2(1H)-yl]-N-isoxazol-3-yl-4-methylbenzamide as a solid (63 mg); NMR Spectrum: (DMSOd$_6$) 2.15 (s, 3H), 2.23 (s, 6H), 2.69 (t, 2H), 4.17 (m, 2H), 6.73 (d, 1H), 7.03 (s, 1H), 7.24 (d, 1H), 7.41 (d, 1H), 7.59 (d, 1H), 7.69 (s, 1H), 7.71 (d, 1H), 8.01 (s, 1H), 8.06 (d, 1H), 8.84 (s, 1H), 11.46 (s, 1H); Mass Spectrum: M+H$^+$ 433.

3-[7-[2-(Dimethylamino)ethoxy]-1-oxoisoquinolin-2(1H)-yl]-4-methylbenzoic acid used as starting material was prepared as follows:—

3-(7-Hydroxy-1-oxoisoquinolin-2(1H)-yl)-4-methylbenzoic acid (0.47 g), 2-dimethylaminoethyl chloride hydrochloride (0.69 g), potassium carbonate (2.21 g), and sodium iodide (24 mg) were stirred in acetone (25 ml) at 60° C. for 17 hours. 2N NaOH (5 ml) was added, the reaction stirred for 20 minutes and the acetone removed by evaporation. The residue was acidified with concentrated hydrochloric acid and the solution was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give 3-[7-[2-(dimethylamino)ethoxy]-1-oxoisoquinolin-2(1H)-yl]-4-methylbenzoic acid as an oil (232 mg); Mass Spectrum: M+H$^+$ 367.

3-(7-Hydroxy-1-oxoisoquinolin-2(1H)-yl)-4-methylbenzoic acid used as starting material was prepared as follows:—

N-Cyclopropyl-3-(7-hydroxy-1-oxoisoquinolin-2(1H)-yl)-4-methylbenzamide (0.5 g) was stirred in 48% hydrobromic acid (7 mL) and heated under microwave irradiation conditions (Personal Chemistry Emrys Optimizer with 300 W magnetron) at 150° C. for 1 hour. The reaction mixture was diluted with ethyl acetate, washed water (×3), brine, dried (magnesium sulfate) and concentrated to a brown solid. The solid was triturated with diethyl ether to yield 3-(7-hydroxy-1-oxoisoquinolin-2(1H)-yl)-4-methylbenzoic acid as a brown solid (0.32 g); NMR Spectrum: (DMSOd$_6$) 2.11 (s, 3H), 6.65 (d, 1H), 7.12 (d, 1H), 7.27 (d, 1H), 7.54 (d, 1H), 7.60 (s, 1H), 7.61 (d, 1H), 7.78 (s, 1H), 7.95 (d, 1H), 10.09 (s, 1H), 13.05 (s, 1H); Mass Spectrum: M+H$^+$ 296.

EXAMPLE 8

3-[7-[2-(Dimethylamino)ethoxy]-1-oxoisoquinolin-2(1H)-yl]-N-ethyl-4-methylbenzamide N-Ethyl-3-(7-hydroxy-1-oxoisoquinolin-2(1H)-yl)-4-methylbenzamide (88 mg), 2-dimethylaminoethyl chloride hydrochloride (51 mg), potassium carbonate (0.38 g), and sodium iodide (3 mg) were stirred in acetone (4 ml) at 60° C. for 17 hours. The reaction mixture was filtered, the solids washed with acetone, and the filtrate was concentrated. The residue was dissolved in ethyl acetate and washed with 2N NaOH solution, brine, dried (magnesium sulfate) and concentrated. Purification by column chromatography on a silica-column eluting with 10% methanol/ethyl acetate+1% aqueous ammonia solution gave 3-[7-[2-(dimethylamino)ethoxy]-1-oxoisoquinolin-2(1H)-yl]-N-ethyl-4-methylbenzamide as a white solid; NMR Spectrum: (DMSOd$_6$) 1.11 (t, 3H), 2.10 (s, 3H), 2.24 (s, 6H), 2.68 (t, 2H), 3.28 (m, 2H), 4.18 (m, 2H), 6.72 (d, 1H), 7.21 (d, 1H), 7.41 (d, 1H), 7.50 (d, 1H), 7.69 (s, 1H), 7.71 (d, 1H), 7.78 (s, 1H), 7.89 (d, 1H), 8.48 (s, 1H); Mass Spectrum: M+H$^+$ 394.

N-Ethyl-3-(7-hydroxy-1-oxoisoquinolin-2(1H)-yl)-4-methylbenzamide used as starting material was prepared as follows:—

To a stirred solution of 3-(7-hydroxy-1-oxoisoquinolin-2(1H)-yl)-4-methylbenzoic acid (140 mg) in methylene chloride (3 ml) was added thionyl chloride (40 µl) and DMF (40 µl) and the solution heated to 40° C. for 35 minutes. The reaction mixture was cooled to room temperature and 2M ethylamine in THF (2.1 mL) was added and the reaction stirred at room temperature for 2 hours. The reaction was dissolved in 1N NaOH and washed with ethyl acetate. The aqueous layer was acidified to pH 3 and extracted with ethyl acetate (×3). The organic layers were dried (magnesium sulfate) and concentrated to yield N-ethyl-3-(7-hydroxy-1-oxoisoquinolin-2(1H)-yl)-4-methylbenzamide as a solid (88 mg); NMR Spectrum: (DMSOd$_6$) 1.11 (t, 3H), 2.09 (s, 3H), 3.30 (m, 2H), 6.66 (d, 1H), 7.11 (d, 1H), 7.25 (d, 1H), 7.49 (d, 1H), 7.60 (s, 1H), 7.61 (d, 1H), 7.77 (s, 1H), 7.89 (d, 1H), 8.47 (s, 1H); Mass Spectrum: M+H$^+$ 323.

EXAMPLE 9

Using an analogous procedure to that described in Example 8, N-Ethyl-3-(7-hydroxy-1-oxoisoquinolin-2(1H)-yl)-4-methylbenzamide was alkylated with the appropriate alkylating reagent to give the compounds described in Table 3.

TABLE 3

| R | Method | Note |
|---|---|---|
| Morpholin-4-yl | Ex 8 | a |

Notes
a The product gave the following data; NMR Spectrum: (DMSOd$_6$) 1.11 (t, 3 H), 2.10 (s, 3 H), 2.52 (m, 4 H), 2.75 (t, 2 H), 3.27 (m, 2 H), 3.58 (m, 4 H), 4.22 (m, 2 H), 6.73 (d, 1 H), 7.25 (d, 1 H), 7.42 (m, 1 H), 7.51 (d, 1 H), 7.69 (s, 1 H), 7.72 (d, 1 H), 7.78 (s, 1 H), 7.90 (d, 1 H), 8.50 (s, 1 H); Mass Spectrum: M + H$^+$ 436.

EXAMPLE 10

N-Cyclopropyl-4-methyl-3-[1-oxo-7-[3-(4-propionylpiperazin-1-yl)propoxy]isoquinolin-2(1H)-yl]benzamide A mixture of 3-[7-(3-chloropropyl)-1-oxoisoquinolin-2(1H)-yl]-N-cyclopropyl-4-methylbenzamide and 3-[7-(3-bromopropyl)-1-oxoisoquinolin-2(1H)-yl]-N-cyclopropyl-4-methylbenzamide (3:1, 0.18 g), potassium iodide (0.14 g), 1-propionylpiperazine (0.38 g) were stirred in DMA (4.5 ml) and heated under microwave irradiation conditions (Personal Chemistry Emrys Optimizer with 300 W magnetron) at 150° C. for 90 minutes. The reaction mixture was diluted with ethyl acetate and washed with water (×5), brine (×2), dried (magnesium sulfate) and concentrated. Purification by column chromatography on a silica column eluting using a gradient of methylene chloride to 6% methano/methylene chloride gave N-cyclopropyl-4-methyl-3-[1-oxo-7-[3-(4-propionylpiperazin-1-yl)propoxy]isoquinolin-2(1H)-yl]benzamide (0.174 g) as a white foam; NMR Spectrum: (CDCl$_3$) 0.57 (m, 2H), 0.82 (m, 2H), 1.14 (t, 3H), 2.02 (m, 2H), 2.19 (s, 3H), 2.33 (q, 2H), 2.44 (m, 4H), 2.56 (t, 2H), 2.85 (m, 1H), 3.47 (m, 2H), 3.63 (m, 2H), 4.16 (t, 2H), 6.46 (s, 1H), 6.51 (d, 1H), 6.86 (d, 1H), 7.29 (m, 1H), 7.39 (d, 1H), 7.47 (d, 1H), 7.61 (d, 1H), 7.75 (d, 1H), 7.81 (d, 1H); Mass Spectrum: M+H$^+$ 517.

The mixture of 3-[7-(3-chloropropyl)-1-oxoisoquinolin-2(1H)-yl]-N-cyclopropyl-4-methylbenzamide and 3-[7-(3-bromopropyl)-1-oxoisoquinolin-2(1H)-yl]-N-cyclopropyl-4-methylbenzamide (3:1 mixture) used as starting material was prepared as follows:—

1-Bromo-3-chloropropane (12.35 ml) was added to a solution of N-cyclopropyl-3-(7-hydroxy-1-oxoisoquinolin-2(1H)-yl)-4-methylbenzamide (4.17 g) and potassium carbonate (17.25 g) in DMF (145 ml) at room temperature. This solution was allowed to stir at 50° C. for 18 hours. The reaction mixture evaporated and redissolved in dissolved in ethyl acetate and washed with water. The organic layer was washed with 2N HCl, water, brine, dried (magnesium sulfate) and concentrated to give a cream solid. This solid was stirred in diethyl ether for 90 minutes, collected by filtration and air-dried to yield a mixture of 3-[7-(3-chloropropoxy)-1-oxoisoquinolin-2(1H)-yl]-N-cyclopropyl-4-methylbenzamide; NMR Spectrum: (DMSOd$_6$) 0.55 (m, 2H), 0.89 (m, 2H), 2.19 (s, 3H), 2.30 (m, 2H), 2.80 (m, 1H), 3.80 (m, 2H), 4.23 (m, 2H), 6.48 (m, 1H), 6.56 (m, 1H), 6.84 (m, 1H), 7.28 (m, 1H), 7.38 (m, 1H), 7.43 (m, 2H), 7.52 (m, 1H), 7.78 (m, 2H); Mass Spectrum: M+H$^+$ 397 and 3-[7-(3-bromopropoxy)-1-oxoisoquinolin-2(1H)-yl]-N-cyclopropyl-4-methylbenzamide;

NMR Spectrum: (DMSOd₆) 0.55 (m, 2H), 0.89 (m, 2H), 2.19 (s, 3H), 2.38 (m, 2H), 2.80 (m, 1H), 3.64 (m, 2H), 4.23 (m, 2H), 6.48 (m, 1H), 6.56 (m, 1H), 6.84 (m, 1H), 7.28 (m, 1H), 7.38 (m, 1H), 7.43 (m, 2H), 7.52 (m, 1H), 7.78 (m, 2H); Mass Spectrum: M+H⁺ 455 in a 3:1 ratio (3.99 g).

EXAMPLE 11

Using an analogous procedure to that described in Example 10, a mixture of 3-[7-(3-chloropropyl)-1-oxoisoquinolin-2(1H)-yl]-N-cyclopropyl-4-methylbenzamide and 3-[7-(3-bromopropyl)-1-oxoisoquinolin-2(1H)-yl]-N-cyclopropyl-4-methylbenzamide (3:1 mixture) was reacted with the appropriate amine to give the compounds described in Table 4.

TABLE 4

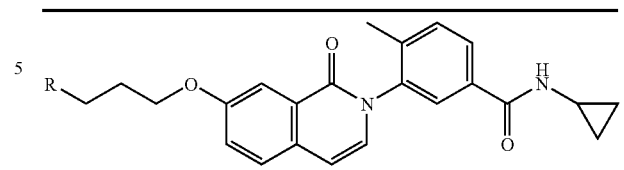

| R | Method | Note |
|---|---|---|
| Isopropyl(methyl)amino | Ex 10 | a |
| 4,4-Difluoropiperidin-1-yl | Ex 10 | b |
| Piperidin-1-yl | Ex 10 | c |
| Methyl(tetrahydrofuran-2-ylmethyl)amino | Ex 10 | d |
| (2R,6S)-2,6-dimethylmorpholin-4-yl | Ex 10 | e |
| Pyrrolidin-1-yl | Ex 10 | f |
| Morpholin-4-yl | Ex 10 | g |
| Methyl(prop-2-yn-1-yl)amino | Ex 10 | h |
| 3,3-Difluoropyrrolidin-1-yl | Ex 10 | i |
| 3-Fluoropiperidin-1-yl)propoxy | Ex 10 | j |
| Methyl(tetrahydro-2H-pyran-4-yl) | Ex 10 | k |
| 4-Fluoropiperidin-1-yl | Ex 10 | l |
| (3S)-3-Fluoropyrrolidin-1-yl | Ex 10 | m |
| (3R)-3-Fluoropyrrolidin-1-yl | Ex 10 | n |

Notes
a) The product gave the following data; NMR Spectrum: (CDCl₃) d 0.56 (m, 2H), 0.80 (m, 2H), 1.01 (d, 6H), 1.99 (m, 2H), 2.19 (s, 3H), 2.24 (s, 3H), 2.59 (t, 2H), 2.84 (m, 2H), 4.14 (t, 2H), 6.46 (m, 1H), 6.54 (s, 1H), 6.83 (m, 1H), 7.27 (m, 1H), 7.37 (m, 1H), 7.43 (m, 1H), 7.61 (d, 1H), 7.77 (m, 2H); Mass Spectrum: M + H⁺ 449.
b) The product gave the following data; NMR Spectrum: (CDCl₃) 0.57 (m, 2H), 0.81 (m, 2H), 2.00 (m, 6H), 2.18 (s, 3H), 2.59 (m, 6H), 2.84 (m, 1H), 4.15 (m, 2H), 6.50 (m, 1H), 6.86 (m, 1H), 7.28 (m, 1H), 7.38 (d, 1H), 7.47 (m, 1H), 7.61 (d, 1H), 7.75 (m, 1H), 7.80 (d, 1H); Mass Spectrum: M + H⁺ 497.
c) The product gave the following data; NMR Spectrum: (CDCl₃) 0.56 (m, 2H), 0.80 (m, 2H), 1.46 (m, 2H), 1.63 (m, 4H), 2.06 (m, 2H), 2.18 (s, 3H), 2.47 (m, 4H), 2.55 (m, 2H), 2.83 (m, 1H), 4.13 (t, 2H), 6.49 (m, 2H), 6.85 (m, 1H), 7.27 (m, 1H), 7.38 (d, 1H), 7.45 (d, 1H), 7.61 (d, 1H), 7.77 (m, 2H); Mass Spectrum: M + H⁺ 460.
d) The product gave the following data; NMR Spectrum: (CDCl₃) 0.56 (m, 2H), 0.80 (m, 2H), 1.50 (m, 1H), 1.82 (m, 2H), 1.99 (m, 3H), 2.34 (s, 3H), 2.34 (s, 3H), 2.45 (m, 1H), 2.53 (m, 1H), 2.64 (m, 2H), 2.83 (m, 1H), 3.71 (m, 1H), 3.85 (m, 1H), 4.00 (m, 1H), 4.14 (t, 2H), 6.48 (m, 2H), 6.52 (s, 1H), 6.84 (m, 1H), 7.28 (m, 1H), 7.38 (d, 1H), 7.44 (d, 1H), 7.61 (d, 1H), 7.77 (m, 2H); Mass Spectrum: M + H⁺ 490.
e) The product gave the following data; NMR Spectrum: (CDCl₃) 0.57 (m, 2H), 0.81 (m, 2H), 1.16 (d, 6H), 1.74 (t, 2H), 2.02 (m, 2H), 2.19 (s, 3H), 2.52 (t, 2H), 2.76 (m, 2H), 2.84 (m, 1H), 3.68 (m, 2H), 4.15 (t, 2H), 6.46 (s, 1H), 6.50 (m, 1H), 6.86 (m, 1H), 7.28 (m, 1H), 7.39 (d, 1H), 7.46 (d, 1H), 7.61 (d, 1H), 7.75 (m, 1H), 7.80 (d, 1H); Mass Spectrum: M + H⁺ 490.
f) The product gave the following data; NMR Spectrum: (CDCl₃) 0.56 (m, 2H), 0.79 (m, 2H), 1.81 (m, 4H), 2.08 (m, 2H), 2.18 (s, 3H), 2.59 (m, 4H), 2.69 (t, 2H), 2.82 (m, 1H), 4.15 (t, 2H), 6.50 (m, 2H), 6.84 (m, 1H), 7.28 (m, 1H), 7.38 (d, 1H), 7.44 (d, 1H), 7.61 (d, 1H), 7.77 (m, 2H); Mass Spectrum: M + H⁺ 446.
g) The product gave the following data; NMR Spectrum: (CDCl₃) 0.56 (m, 2H), 0.81 (m, 2H), 2.02 (m, 2H), 2.19 (s, 3H), 2.47 (t, 4H), 2.55 (t, 2H), 2.84 (m, 1H), 3.72 (t, 4H), 4.16 (t, 2H), 6.49 (m, 2H), 6.85 (m, 1H), 7.28 (m, 1H), 7.38 (d, 1H), 7.46 (d, 1H), 7.61 (d, 1H), 7.75 (m, 1H), 7.80 (d, 1H); Mass Spectrum: M + H⁺ 462.
h) The product gave the following data; NMR Spectrum: (CDCl₃) 0.56 (m, 2H), 0.80 (m, 2H), 2.00 (m, 2H), 2.18 (s, 3H), 2.22 (t, 1H), 2.34 (s, 3H), 2.64 (t, 2H), 2.83 (m, 1H), 3.38 (d, 2H), 4.14 (t, 2H), 6.48 (m, 2H), 6.84 (m, 1H), 7.28 (m, 1H), 7.38 (d, 1H), 7.45 (d, 1H), 7.61 (d, 1H), 7.77 (m, 2H); Mass Spectrum: M + H⁺ 444.
i) The product gave the following data; NMR Spectrum: (CDCl₃) 0.56 (m, 2H), 0.81 (m, 2H), 2.01 (m, 2H), 2.19 (s, 3H), 2.27 (m, 2H), 2.67 (m, 2H), 2.76 (m, 2H), 2.84 (m, 1H), 2.93 (t, 2H), 4.16 (t, 2H), 6.44 (s, 1H), 6.50 (m, 1H), 6.86 (m, 1H), 7.28 (m, 1H), 7.39 (d, 1H), 7.46 (d, 1H), 7.61 (d, 1H), 7.76 (m, 1H), 7.79 (d, 1H); Mass Spectrum: M + H⁺ 482.
j) The product gave the following data; NMR Spectrum: (CDCl₃) 0.57 (m, 2H), 0.82 (m, 2H), 1.58 (m, 2H), 1.86 (m, 2H), 2.01 (m, 2H), 2.19 (s, 3H), 2.29 (m, 1H), 2.42 (m, 1H), 2.55 (m, 3H), 2.82 (m, 2H), 4.14 (t, 2H), 4.63 (m, 1H), 6.42 (s, 1H), 6.51 (m, 1H), 6.86 (m, 1H), 7.28 (m, 1H), 7.39 (d, 1H), 7.46 (d, 1H), 7.60 (d, 1H), 7.76 (q, 1H), 7.79 (d, 1H); Mass Spectrum: M + H⁺ 478.
k) The product gave the following data; NMR Spectrum: (CDCl₃) 0.49 (m, 2H), 0.74 (m, 2H), 1.55 (m, 4H), 1.92 (m, 2H), 2.12 (s, 3H), 2.23 (s, 3H), 2.51 (m, 1H), 2.60 (t, 2H), 2.77 (m, 1H), 3.28 (m, 2H), 3.93 (m, 2H), 4.08 (t, 2H), 6.41 (m, 2H), 6.78 (m, 1H), 7.21 (m, 1H), 7.31 (d, 1H), 7.39 (d, 1H), 7.54 (d, 1H), 7.69 (m, 1H), 7.73 (d, 1H); Mass Spectrum: M + H⁺ 490.
l) The product gave the following data; NMR Spectrum: (CDCl₃) 0.49 (m, 2H), 0.73 (m, 2H), 1.88 (m, 6H), 2.11 (s, 3H), 2.35 (m, 2H), 2.53 (m, 4H), 2.76 (m, 1H), 4.07 (m, 2H), 4.60 (m, 1H), 6.42 (m, 2H), 6.78 (m, 1H), 7.20 (m, 1H), 7.31 (d, 1H), 7.38 (d, 1H), 7.54 (d, 1H), 7.70 (m, 2H); Mass Spectrum: M + H⁺ 478.
m) The product gave the following data; NMR Spectrum: (CDCl₃) 0.48 (m, 2H), 0.73 (m, 2H), 2.03 (m, 7H), 2.40 (m, 1H), 2.72 (m, 6H), 4.09 (t, 2H), 5.10 (m, 1H), 6.42 (m, 2H), 6.77 (m, 1H), 7.20 (m, 1H), 7.31 (d, 1H), 7.37 (d, 1H), 7.54 (d, 1H), 7.70 (m, 2H); Mass Spectrum: M + H⁺ 464.
n) The product gave the following data; NMR Spectrum: (CDCl₃) 0.49 (m, 2H), 0.73 (m, 2H), 2.03 (m, 7H), 2.40 (m, 1H), 2.72 (m, 6H), 4.09 (t, 2H), 5.10 (m, 1H), 6.41 (m, 2H), 6.77 (m, 1H), 7.20 (m, 1H), 7.31 (d, 1H), 7.37 (d, 1H), 7.54 (d, 1H), 7.70 (m, 2H); Mass Spectrum: M + H⁺ 464.

N-Methyl-N-(tetrahydropyran-4-yl)amine hydrochloride used as starting material was prepared as follows:—

A mixture of methylamine hydrochloride (5.4 g), terahydro-4H-pyran-4-one (8 g), triethylamine (2.4 g), 5% palladium on carbon (400 mg) and methanol (56 ml) were stirred at 60° C. for 3 hours under a hydrogen atmosphere. The palladium on carbon was removed by filtration through diatomaceous earth (Celite®) and the resultant filtrate evaporated in vacuo to a cream solid. To this solid were added propan-2-ol (39 ml), methanol (10 ml) and diethyl ether (20 ml), the resultant suspension then allowed to stir at room temperature for 1 hour, the solid was collected by filtration, washed with diethyl ether (10 ml) and dried in vacuo at room temperature to give N-methyl-N-(tetrahydropyran-4-yl)amine hydrochloride (9.83 g) as a white solid; NMR Spectrum: (DMSOd₆) 1.62 (m, 2H); 1.94 (m, 2H); 2.53 (m, 3H); 3.14 (m, 1H); 3.3 (m, 2H); 3.91 (m, 2H); 9.24 (s, 2H).

EXAMPLE 12

N-Cyclopropyl-4-methyl-3-[7-(4-methylpiperazin-1-yl)-1-oxoisoquinolin-2(1H)-yl]benzamide 2-{5-[(Cyclopropylamino)carbonyl]-2-methylphenyl}-1-oxo-1,2-dihydroisoquinolin-7-yl trifluoromethanesulfonate (58 mg), palladium acetate (3 mg), BINAP (16 mg) and cesium carbonate (101 mg) were placed in a reaction tube under an atmosphere of argon. Toluene (0.5 ml) was added followed by N-methylpiperazine (0.041 ml) and the reaction mixture was stirred in a sealed tube at 95° C. for 16 hours. The reaction mixture was diluted with ethyl acetate and washed with water (2×), brine, dried (magnesium sulfate) and concentrated. Purification by RP-HPLC (5-95% MeCN: 1% NH₄OH in H₂O, 21 ml/min using a Waters Xterra Prep RP18 5 micron, 19×100 mm column) gave N-cyclopropyl-4-methyl-3-[7-(4-methylpiperazin-1-yl)-1-oxoisoquinolin-2 (1H)-yl]benzamide (17 mg) as a pale yellow solid; NMR Spectrum: (DMSOd₆) 0.55 (m, 2H), 0.69 (m, 2H), 2.09 (s, 3H), 2.29 (s, 3H), 2.56 (m, 4H), 2.85 (m, 1H), 3.29 (m, 4H), 6.65 (d, 1H), 7.11 (d, 1H), 7.48 (d, 1H), 7.52 (d, 1H), 7.61 (m, 2H), 7.74 (s, 1H), 7.87 (d, 1H), 8.43 (d, 1H); Mass Spectrum: M+H⁺ 417.

2-{5-[(Cyclopropylamino)carbonyl]-2-methylphenyl}-1-oxo-1,2-dihydroisoquinolin-7-yl trifluoromethanesulfonate used as starting material was prepared as follows:—

N-Cyclopropyl-3-(7-hydroxy-1-oxoisoquinolin-2(1H)-yl)-4-methylbenzamide (250 mg), N-phenyltrifluoromethanesulfonamide (267 mg) and potassium carbonate (311 mg) were stirred in THF (6 ml) and heated under microwave irradiation (Personal Chemistry Emrys Optimizer with 300 W magnetron) at 120° C. for 10 minutes. The reaction mixture was diluted with ethyl acetate and washed with water (2×), brine, dried (magnesium sulfate) and concentrated. Purification by column chromatography with a gradient of iso-hexane to 70% ethyl acetate/iso-hexane yielded 2-{5-[(cyclopropylamino)carbonyl]-2-methylphenyl}-1-oxo-1,2-dihydroisoquinolin-7-yl trifluoromethanesulfonate as a cream coloured solid (264 mg); NMR Spectrum: (DMSOd$_6$) 0.53 (m, 2H), 0.67 (m, 2H), 2.10 (s, 3H), 2.83 (m, 1H), 6.87 (d, 1H), 7.49 (m, 2H), 7.76 (s, 1H), 7.86 (d, 1H), 7.93 (d, 1H), 8.00 (d, 1H), 8.19 (s, 1H), 8.42 (d, 1H); Mass Spectrum: M+Na$^+$ 489.

EXAMPLE 13

N-Cyclopropyl-3-[7-[1(1-ethylpiperidin-4-yl)oxy]-1-oxoisoquinolin-2(1H)-yl]-4-methylbenzamide N-Cyclopropyl-4-methyl-3-[1-oxo-7-(piperidin-4-yloxy)isoquinolin-2(1H)-yl]benzamide (50 mg), iodoethane (0.105 ml) and potassium carbonate (66 mg) were stirred in DMF (0.5 ml) at room temperature for 18 hours. The reaction mixture was diluted with ethyl acetate and washed with water (5×), brine, dried (magnesium sulfate) and concentrated to give N-cyclopropyl-3-[7-[(1-ethylpiperidin-4-yl)oxy]-1-oxoisoquinolin-2(1H)-yl]-4-methylbenzamide as a cream coloured foam solid (44 mg); NMR Spectrum: (DMSOd$_6$) 0.56 (m, 2H), 0.69 (m, 2H), 1.00 (t, 3H), 1.69 (m, 2H), 1.99 (m, 2H), 2.10 (s, 3H), 2.25 (m, 2H), 2.38 (m, 2H), 2.71 (m, 2H), 2.85 (m, 1H), 4.53 (m, 1H), 6.70 (d, 1H), 7.20 (d, 1H), 7.41 (d, 1H), 7.49 (d, 1H), 7.67 (s, 1H), 7.70 (d, 1H), 7.72 (s, 1H), 7.88 (d, 1H), 8.42 (d, 1H); Mass Spectrum: M+H$^+$ 446.

N-Cyclopropyl-4-methyl-3-[1-oxo-7-(piperidin-4-yloxy)isoquinolin-2(1H)-yl]benzamide used as starting material was prepared as follows:—

N-Cyclopropyl-3-(7-hydroxy-1-oxoisoquinolin-2(1H)-yl)-4-methylbenzamide (200 mg) was stirred with cesium fluoride (364 mg) and 4-methanesulfonyloxypiperidine-1-carboxylic acid tert-butyl ester (251 mg) in DMA (1.5 ml) at 85° C. for 24 hours (during this time further additions (4×125 mg) of 4-methanesulfonyloxypiperidine-1-carboxylic acid tert-butyl ester took place). The reaction mixture was diluted with ethyl acetate and washed with 1N NaOH (2×), water (3×), brine, dried (magnesium sulfate) and concentrated to a brown oil. Purification by column chromatography with a gradient of 50% ethyl acetate/iso-hexane to 100% ethyl acetate gave a cream coloured solid. The solid was dissolved in 4M HCl in dioxane solution (1 ml) and methanol (0.5 ml) and stirred for 16 hours at room temperature. The reaction mixture was concentrated and the residue was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give N-cyclopropyl-4-methyl-3-[1-oxo-7-(piperidin-4-yloxy)isoquinolin-2(1H)-yl]benzamide as a cream coloured foam solid (146 mg); NMR Spectrum: (DMSOd$_6$) 0.55 (m, 2H), 0.69 (m, 2H), 1.50 (m, 2H), 1.95 (m, 2H), 2.10 (s, 3H), 2.60 (m, 2H), 2.84 (m, 1H), 2.96 (m, 2H), 4.54 (m, 1H), 6.71 (d, 1H), 7.20 (d, 1H), 7.41 (d, 1H), 7.49 (d, 1H), 7.67 (s, 1H), 7.80 (d, 1H), 7.83 (s, 1H), 7.87 (d, 1H), 8.42 (d, 1H); Mass Spectrum: M+H$^+$ 418.

4-Methanesulfonyloxypiperidine-1-carboxylic acid tert-butyl ester used as starting material was prepared as follows:—

To a stirred 1M solution of lithium bis(trimethylsilyl)amide in THF (140 ml) at −78° C. was added dropwise over 10 minutes a solution of tert-butyl 4-oxopiperidine-1-carboxylate (27.9 g) in THF (100 ml). The solution was stirred at −78° C. for a further 30 minutes when N-phenyltrifluoromethanesulfonimide (50 g) was added over 30 minutes. The resultant solution was warmed to room temperature and stirred for 18 hours. The solution was washed with 2N NaOH and the aqueous layer extracted with diethyl ether. The organic layers were combined, dried (sodium sulfate) and concentrated to yield 4-methanesulfonyloxypiperidine-1-carboxylic acid tert-butyl ester as an oil (41 g); NMR Spectrum: (CDCl$_3$) 1.45 (s, 9H), 2.43 (m, 2H), 3.63 (t, 2H), 4.05 (d, 2H), 5.77 (m, 1H); Mass Spectrum: M+H$^+$ 332.

EXAMPLE 14

N-Isoxazol-3-yl-4-methyl-3-[7-(4-methylpiperazin-1-yl)-1-oxoisoquinolin-2(1H)-yl]benzamide To a stirred suspension of 4-methyl-3-[7-(4-methylpiperazin-1-yl)-1-oxoisoquinolin-2(1H)-yl]benzoic acid (100 mg) and DMF (0.05 ml) in methylene chloride (2.5 ml) was added thionyl chloride (0.1 ml) and the suspension was stirred at 40° C. for 3.5 hours. The reaction mixture was concentrated and the residue was stirred in methylene chloride (2.5 ml) with N,N'-diisopropylethylamine (0.141 ml) and 3-aminoisoxazole (0.078 ml) at room temperature for 2.5 hours. The reaction mixture was partitioned between ethyl acetate and saturated aqueous sodium hydrogen carbonate solution and separated. The aqueous layer was extracted with ethyl acetate (2×) and the combined organic extracts were dried (magnesium sulfate) and concentrated to an orange oil. Purification by column chromatography with a gradient of 10% methanol in methylene chloride to 10% methanol/methylene chloride+1% aqueous ammonia solution gave N-isoxazol-3-yl-4-methyl-3-[7-(4-methylpiperazin-1-yl)-1-oxoisoquinolin-2(1H)-yl]benzamide as a yellow solid (55 mg); NMR Spectrum: (DMSOd$_6$) 2.13 (s, 3H), 2.23 (s, 3H), 2.50 (m, 4H), 3.27 (m, 4H), 6.68 (d, 1H), 7.04 (s, 1H), 7.15 (d, 1H), 7.58 (m, 2H), 7.64 (d, 1H), 7.99 (s, 1H), 8.04 (d, 1H), 8.85 (s, 1H), 11.47 (s, 1H); Mass Spectrum: M+H$^+$ 444.

4-Methyl-3-[7-(4-methylpiperazin-1-yl)-1-oxoisoquinolin-2(1H)-yl]benzoic acid used as starting material was prepared as follows:—

To a stirred solution of 3-(7-hydroxy-1-oxoisoquinolin-2(1H)-yl)-4-methylbenzoic acid (440 mg) and thionyl chloride (0.131 ml) in methylene chloride (8 ml) was added DMF (0.14 ml) and the solution was heated at 40° C. for 2 hours. The reaction mixture was allowed to cool to room temperature before the addition of methanol (5 ml) and stirring continued for 2.5 hours. The reaction mixture was concentrated and then dissolved in ethyl acetate and washed with saturated aqueous sodium hydrogen carbonate (2×), brine, dried (magnesium sulfate) and concentrated to yield the crude methyl 3-(7-hydroxy-1-oxoisoquinolin-2(1H)-yl)-4-methylbenzoate as a brown solid (419 mg); NMR Spectrum: (DMSOd$_6$) 2.14 (s, 3H), 3.87 (s, 3H), 6.65 (d, 1H), 7.11 (d, 1H), 7.23 (d, 1H), 7.57-7.62 (m, 3H), 7.80 (s, 1H), 7.97 (d, 1H), 10.00 (s, 1H); Mass Spectrum: M+Na$^+$ 332.

Methyl 3-(7-hydroxy-1-oxoisoquinolin-2(1H)-yl)-4-methylbenzoate (529 mg), N-phenyltrifluoromethanesulfonamide (612 mg) and potassium carbonate (709 mg) were stirred in THF (15 ml) and heated under microwave irradiation (Personal Chemistry Emrys Optimizer with 300 W magnetron) at 120° C. for 10 minutes. The reaction mixture was concentrated and the residue was dissolved in ethyl acetate and washed with water (×2), brine, dried (magnesium sulfate) and concentrated. Purification by column chromatography with a gradient of iso-hexane to 30% ethyl acetate/iso-hexane yielded methyl 4-methyl-3-[1-oxo-7-{[(trifluoromethyl)sulfonyl]oxy} isoquinolin-2(1H)-yl]benzoate as a white solid (613 mg); NMR Spectrum: (DMSOd$_6$) 2.15 (s, 3H), 3.86 (s, 3H), 6.89 (d, 1H), 7.50 (d, 1H), 7.60 (d, 1H), 7.90 (s, 1H), 7.93 (d, 1H), 8.00 (m, 2H), 8.20 (s, 1H); Mass Spectrum: M+Na$^+$ 464.

Methyl 4-methyl-3-[1-oxo-7-{[(trifluoromethyl)sulfonyl]oxy} isoquinolin-2(1H)-yl]benzoate (243 mg), palladium acetate (12 mg), BINAP (69 mg), and cesium carbonate (449 mg) were placed in a reaction tube under an atmosphere of argon. Toluene (2.5 ml) was added followed by N-methylpiperazine (0.183 ml) and the reaction mixture was stirred in a sealed tube at 95° C. for 16 hours. The reaction mixture was diluted with ethyl acetate and washed with water (2×), brine, dried (magnesium sulfate) and concentrated. Purification by column chromatography on an ion exchange column (isolute SCX column from International Sorbent Technology Limited, Henoed, Mid-Glamorgan, UK) using initially methanol and then a 99:1 mixture of methanol and aqueous ammonia solution gave methyl 4-methyl-3-[7-(4-methylpiperazin-1-yl)-1-oxoisoquinolin-2(1H)-yl]benzoate as a brown solid (189 mg); NMR Spectrum: (DMSOd$_6$) 2.12 (s, 3H), 2.23 (s, 3H), 2.50 (m, 4H), 3.25 (m, 4H), 3.88 (s, 3H), 6.65 (d, 1H), 7.12 (d, 1H), 7.52-7.60 (m, 3H), 7.63 (d, 1H), 7.80 (s, 1H), 7.99 (d, 1H); Mass Spectrum: M+H$^+$ 392.

To a stirred solution of methyl 4-methyl-3-[7-(4-methylpiperazin-1-yl)-1-oxoisoquinolin-2(1H)-yl]benzoate (272 mg) in methanol was added 1N NaOH solution (0.85 ml) and the reaction mixture was stirred at 65° C. for 30 minutes and then neutralized with 1N HCl. After cooling to room temperature the resulting precipitate was collected by filtration and washed with water, ethyl acetate, methanol and then air-dried to yield 4-methyl-3-[7-(4-methylpiperazin-1-yl)-1-oxoisoquinolin-2(1H)-yl]benzoic acid (166 mg) as a pale yellow solid; NMR Spectrum: (DMSOd$_6$) 2.12 (s, 3H), 2.25 (s, 3H), 2.50 (m, 4H), 3.27 (m, 4H), 6.64 (d, 1H), 7.12 (d, 1H), 7.56 (m, 2H), 7.60 (s, 1H), 7.63 (d, 1H), 7.75 (s, 1H), 7.94 (d, 1H); Mass Spectrum: M+H$^+$ 378.

EXAMPLE 15

3-[7-(2-Aminoethoxy)-1-oxoisoquinolin-2(1H)-yl]-N-cyclopropyl-4-methylbenzamide tert-Butyl {2-[(2-{5-[(cyclopropylamino)carbonyl]-2-methylphenyl}-1-oxo-1,2-dihydroisoquinolin-7-yl)oxy]ethyl}carbamate (145 mg) was dissolved in 4N HCl in dioxane (1.2 ml) and methanol (0.9 ml) stirred at room temperature for 18 hours. The orange solution was concentrated and purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give 3-[7-(2-aminoethoxy)-1-oxoisoquinolin-2(1H)-yl]-N-cyclopropyl-4-methylbenzamide as a white solid (102 mg); NMR Spectrum: (DMSOd$_6$) 0.56 (m, 2H), 0.69 (m, 2H), 2.10 (s, 3H), 2.22 (s, 2H), 2.86 (m, 1H), 2.94 (t, 2H), 4.05 (m, 2H), 6.73 (d, 1H), 7.22 (d, 1H), 7.43 (m, 1H), 7.50 (d, 1H), 7.66 (d, 1H), 7.72 (d, 1H), 7.76 (d, 1H), 7.87 (m, 1H), 8.46 (d, 1H); Mass Spectrum: M+H$^+$ 378.

EXAMPLE 16

N-Isoxazol-3-yl-4-methyl-3-[7-(2-morpholin-4-ylethoxy)-1-oxoisoquinolin-2(1H)-yl]benzamide 4-Methyl-3-[7-(2-morpholin-4-ylethoxy)-1-oxoisoquinolin-2(1H)-yl]benzoic acid (708 mg) was dissolved in methylene chloride (5 ml) and DMF (3 drops) and cooled to 0° C. under an argon atmosphere. Oxalyl chloride (0.33 ml) was added and the reaction mixture stirred at room temperature for 2 hours. Pyridine (1.45 ml) and 3-aminoisoxazole (0.64 ml) were added and the reaction mixture stirred at room temperature for 2 hours. The reaction mixture was diluted with ethyl acetate, washed with 1N NaOH, dried (magnesium sulfate) and concentrated. Purification by column chromatography on an ion exchange column (isolute SCX column from International Sorbent Technology Limited, Henoed, Mid-Glamorgan, UK) using initially methanol and then a 99:1 mixture of methanol and aqueous ammonia solution to give an oily solid. The solid was triturated with ethyl acetate to give N-Isoxazol-3-yl-4-methyl-3-[7-(2-morpholin-4-ylethoxy)-1-oxoisoquinolin-2(1H)-yl]benzamide as a white solid (70 mg); NMR Spectrum: (DMSOd$_6$) 2.15 (s, 3H), 2.50 (m, 4H), 2.75 (m, 2H), 3.55 (m, 4H), 4.20 (m, 2H), 6.75 (m, 1H), 7.05 (m, 1H), 7.25 (m, 1H), 7.45 (m, 1H), 7.60 (m, 1H), 7.70 (m, 2H), 8.00 (m, 2H), 8.85 (s, 1H), 11.45 (s, 1H); Mass Spectrum: M+H$^+$ 475.

4-Methyl-3-[7-(2-morpholin-4-ylethoxy)-1-oxoisoquinolin-2(1H)-yl]benzoic acid used as starting material was prepared as follows:—

3-(7-hydroxy-1-oxoisoquinolin-2(1H)-yl)-4-methylbenzoic acid (885 mg) was dissolved in acetone (50 ml), sodium iodide (45 mg) and potassium carbonate (4.14 g) were added followed by 4-(2-chloroethyl) morpholine hydrochloride (1.68 g). The resultant mixture was stirred at 60° C. for 18 hours. 2N NaOH (9.4 ml) was added and stirred for 20 minutes, cooled and the insoluble material removed by filtration. The filtrate was concentrated, acidified to pH 1 with concentrated hydrochloric acid and purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give 4-methyl-3-[7-(2-morpholin-4-ylethoxy)-1-oxoisoquinolin-2(1H)-yl]benzoic acid as an oil (720 mg); NMR Spectrum: (DMSOd$_6$) 2.00 (s, 1H), 2.60 (m, 4H), 2.80 (m, 2H), 3.18 (m, 4H), 3.75 (m, 2H), 6.40 (d, 1H), 6.80 (d, 1H), 7.03 (d, 1H), 7.20 (m, 1H), 7.40 (d, 1H), 7.75 (m, 3H); Mass Spectrum: M+H$^+$ 409.

EXAMPLE 17

N-isoxazol-3-yl-4-methyl-3-[1-oxo-7-(2-piperidin-1-ylethoxy)isoquinolin-2(1H)-yl]benzamide 4-Methyl-3-[1-oxo-7-(2-piperidin-1-ylethoxy)isoquinolin-2(1H)-yl]benzoic acid (439 mg) was dissolved in methylene chloride (5 ml) and DMF (3 drops) and cooled to 0° C. under an argon atmosphere. Oxalyl chloride (0.19 ml) was added and the reaction mixture stirred at room temperature for 2 hours. Pyridine (0.90 ml) and 3-aminoisoxazole (0.40 ml) were added and the reaction mixture stirred at room temperature for 2 hours. The reaction mixture was diluted with ethyl acetate, washed with 1N NaOH, dried (magnesium sulfate) and concentrated. Purification by column chromatography on an ion exchange column (isolute SCX column from International Sorbent Technology Limited, Henoed, Mid-Glamorgan, UK) using initially methanol and then a 99:1 mixture of methanol and aqueous ammonia solution to give a solid. The solid was triturated with ethyl acetate to give N-isoxazol-3-yl-4-methyl-3-[1-oxo-7-(2-piperidin-1-ylethoxy)isoquinolin-2(1H)-yl]benzamide as a solid (95 mg); NMR Spectrum: (DMSOd$_6$) 1.40 (m, 2H), 1.45 (m, 4H), 2.15 (s, 3H), 2.49 (m, 4H), 2.70 (m, 2H), 4.15 (m, 2H), 6.75 (d, 1H), 7.05 (d, 1H), 7.25 (d, 1H), 7.43 (d, 1H), 7.60 (d, 1H), 7.68 (d, 1H), 7.73 (d, 1H), 8.00 (s, 1H), 8.05 (d, 1H), 8.85 (s, 1H), 11.50 (s, 1H); Mass Spectrum: M+H$^+$ 473.

4-Methyl-3-[1-oxo-7-(2-piperidin-1-ylethoxy)isoquinolin-2(1H)-yl]benzoic acid used as starting material was prepared as follows:—

3-(7-hydroxy-1-oxoisoquinolin-2(1H)-yl)-4-methylbenzoic acid (885 mg) was dissolved in acetone (50 ml), Sodium iodide (45 mg) and potassium carbonate (4.14 g) were added followed by 4-(2-chloroethyl)piperidine hydrochloride (1.67 g). The resultant mixture was stirred at 60° C. for 18 hours. 2N NaOH (9.4 ml) was added and stirred for 20 minutes, cooled and the insoluble material removed by filtration. The filtrate was concentrated, acidified to pH 1 with concentrated hydrochloric acid and purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give 4-methyl-3-[7-(2-piperidin-1-ylethoxy)-1-oxoisoquinolin-2(1H)-yl] benzoic acid as an oil (205 mg); NMR Spectrum: (DMSOd$_6$) 2.13 (s, 1H), 3.00 (m, 4H), 3.35 (m, 2H), 3.95 (m, 4H), 4.58 (m, 2H), 6.46 (d, 1H), 6.90 (d, 1H), 7.25 (m, 1H), 7.35 (m, 1H), 7.50 (d, 1H), 7.80 (d, 1H), 7.87 (d, 1H), 7.98 (m, 1H); Mass Spectrum: M+H$^+$ 407.

EXAMPLE 18

3-[7-{2-[isopropyl(methyl)amino]ethoxy}-1-oxoisoquinolin-2(1H)-yl]-4-methyl-N-(1-methyl-1H-pyrazol-3-yl)benzamide 3-[7-{2-[isopropyl(methyl)amino]ethoxy}-1-oxoisoquinolin-2(1H)-yl]-4-methylbenzoic acid (75 mg) was dissolved in methylene chloride (5 ml) and DMF (3 drops) and cooled to 0° C. under an argon atmosphere. Oxalyl chloride (0.04 ml) was added and the reaction mixture stirred at room temperature for 2 hours. Pyridine (0.16 ml) and 3-amino-1-methylpyrazole (92 mg) were added and the reaction mixture stirred for 18 hours. Purification by column chromatography on an ion exchange column (isolute SCX column from International Sorbent Technology Limited, Henoed, Mid-Glamorgan, UK) using initially methanol and then a 99:1 mixture of methanol and aqueous ammonia solution to give a oil. This oil was purified by column chromatography with a gradient of 10% methanol/ethyl acetate to iso-hexane to 99:1 mixture of 10% methanol in ethyl acetate and aqueous ammonia solution to give 3-[7-{2-[isopropyl(methyl)amino]ethoxy}-1-oxoisoquinolin-2(1)-yl]-4-methyl-N-(1-methyl-1H-pyrazol-3-yl)benzamide as an oil (3 mg); NMR Spectrum: (DMSOd$_6$) 1.00 (m, 6H), 2.15 (s, 3H), 2.25 (s, 3H), 2.75 (m, 2H), 2.85 (m, 1H), 3.80 (s, 3H), 4.15 (m, 2H), 6.60 (m, 1H), 6.70 (m, 1H), 7.25 (m, 1H), 7.40 (m, 1H), 7.55 (m, 1H), 7.62 (m, 1H), 7.70 (m, 2H), 8.00 (m, 1H), 8.05 (m, 1H); Mass Spectrum: M+H$^+$ 474.

3-[7-{2-[Isopropyl(methyl)amino]ethoxy}-1-oxoisoquinolin-2(1H)-yl]-4-methylbenzoic acid used as starting material was prepared as follows:—

3-(7-hydroxy-1-oxoisoquinolin-2(1H)-yl)-4-methylbenzoic acid (5.9 g) was dissolved in DMF (120 ml). Potassium carbonate (27.6 g) and 1-bromo-2-chloroethane (9.99 ml) were added and heated at 50° C. for 18 hours. The reaction mixture was cooled to 40° C. and 2N NaOH (20 ml) was added and the mixture heated at 40° C. for 18 hours. The cooled reaction mixture was adjusted to pH 1 using concentrated hydrochloric acid to yield a brown oil. This oil was extracted with methylene chloride (×2), the organic solution was filtered through silicone treated filter paper (Whatman 1PS) and concentrated to yield 3-[7-(2-chloroethoxy)-1-oxoisoquinolin-2(1H)-yl]-4-methylbenzoic acid as a brown oil (6.59 g); NMR Spectrum: (DMSOd$_6$) 2.22 (s, 1H), 3.85 (m, 2H), 4.40 (m, 2H), 6.60 (m, 1H), 6.95 (m, 1H), 7.40 (m, 1H), 7.46 (m, 1H), 7.56 (m, 1H), 7.90 (m, 1H), 7.95 (m, 1H); Mass Spectrum: M+H$^+$ 358.

3-[7-(2-chloroethoxy)-1-oxoisoquinolin-2(1H)-yl]-4-methylbenzoic acid (504 mg), DIPEA (0.7 ml), potassium iodide (332 mg) and N-methylisopropylamine (0.42 ml) in DMA (4 ml) was heated under microwave irradiation conditions (Personal Chemistry Emrys Optimizer with 300 W magnetron) at 120° C. for 30 minutes. The mixture was diluted with methylene chloride (25 ml), isocyanate resin (CombiZorb) (7.67 g) was added and stirred at room temperature for 18 hours. The resin was removed by filtration and the filtrate was washed with water. The aqueous phase was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to yield 3-[7-{2-[isopropyl(methyl)amino]ethoxy}-1-oxoisoquinolin-2(1H)-yl]-4-methylbenzoic acid as a pale brown solid (110 mg); NMR Spectrum: (DMSOd$_6$) 1.00 (m, 6H), 2.15 (s, 3H), 2.30 (s, 3H), 2.45 (s, 1H), 2.85 (m, 2H), 4.15 (m, 2H), 6.70 (m, 1H), 7.20 (m, 1H), 7.40 (m, 1H), 7.55 (m, 1H), 7.70 (m, 2H), 7.80 (m, 1H), 7.95 (m, 1H); Mass Spectrum: M+H$^+$ 395.

EXAMPLE 19

Using an analogous procedure to that described in Example 18, 3-[7-{2-[isopropyl(methyl)amino]ethoxy}-1-oxoisoquinolin-2(1H)-yl]-4-methylbenzoic acid was reacted with the appropriate amine to give the compounds described in Table 5.

TABLE 5

| R | Method | Note |
|---|---|---|
| 5-Pyrazole-1-Me | Ex 18 | a |
| Methoxy | Ex 18 | b |
| Cyclobutyl | Ex 18 | c |

Notes
a The product gave the following data; NMR Spectrum: (DMSOd$_6$) 0.95 (m, 6 H), 2.12 (s, 3 H), 2.22 (s, 3 H), 2.75 (m, 2 H), 3.20 (m, 1 H), 3.70 (s, 3 H), 4.10 (m, 2 H), 6.24 (d, 1 H), 6.75 (d, 1 H), 7.28 (m, 1 H), 7.40 (m, 2 H), 7.64 (m, 1 H), 7.70 (d, 1 H), 7.75 (d, 1 H), 7.92 (s, 1 H), 8.00 (d, 1 H); Mass Spectrum: M + H$^+$ 474.

TABLE 5-continued

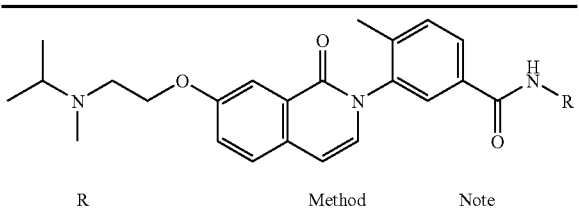

| R | Method | Note |
|---|---|---| b The product gave the following data; NMR Spectrum: (DMSOd₆) 0.95 (m, 6 H), 2.10 (s, 3 H), 2.20 (s, 3 H), 2.70 (m, 1 H), 2.75 (m, 2 H), 4.10 (m, 2 H), 6.70 (m, 1 H), 7.20 (m, 1 H), 7.50 (m, 3 H), 7.68 (m, 1 H), 7.72 (m, 1 H), 7.80 (m, 1 H), 7.90 (m, 1 H), 8.00 (m, 1 H); Mass Spectrum: M + H⁺ 424.
c The product gave the following data; NMR Spectrum: (DMSOd₆) 1.00 (m, 6 H), 1.65 (m, 2 H), 2.10 (m, 5 H), 2.25 (m, 5 H), 2.75 (m, 2 H), 2.80 (m, 1 H), 3.00 (s, 1 H), 4.01 (m, 2 H), 6.75 (m, 1 H), 7.30 (m, 1 H), 7.50 (m, 2 H), 7.70 (m, 2 H), 7.80 (m, 1 H), 7.95 (m, 1 H), 8.70 (m, 1 H); Mass Spectrum: M + H⁺ 448.

EXAMPLE 20

N-Cyclobutyl-3-(7-hydroxy-1-oxoisoquinolin-2(1H)-yl)-4-methylbenzamide 3-(7-Hydroxy-1-oxoisoquinolin-2(1H)-yl)-4-methylbenzoic acid (295 mg), HATU (406 mg) and cyclobutylamine (0.43 ml) were dissolved in DMF (25 ml) and stirred at room temperature for 18 hours. The reaction mixture was poured into water and extracted with ethyl acetate. The ethyl acetate layer was washed with water, dried (magnesium sulfate) and concentrated. The residue was purified by column chromatography with ethyl acetate to give N-cyclobutyl-3-(7-hydroxy-1-oxoisoquinolin-2(1H)-yl)-4-methylbenzamide as a white solid (150 mg); NMR Spectrum: (DMSOd₆) 1.35 (m, 2H), 2.03 (m, 2H), 2.10 (s, 3H), 2.20 (m, 2H), 4.40 (m, 1H), 6.65 (d, 1H), 7.12 (d, 1H), 7.22 (m, 1H), 7.46 (d, 1H), 7.60 (m, 2H), 7.76 (s, 1H), 7.85 (d, 1H) 8.60 (d, 1H), 10.00 (s, 1H); Mass Spectrum: M+H⁺ 349.

EXAMPLE 21

Using an analogous procedure to that described in Example 20, 3-(7-hydroxy-1-oxoisoquinolin-2(1H)-yl)-4-methylbenzoic acid was reacted with the appropriate amine to give the compounds described in Table 7.

TABLE 6

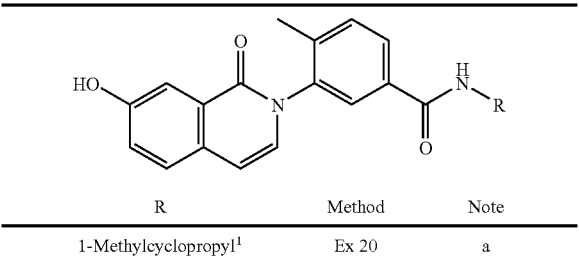

| R | Method | Note |
|---|---|---|
| 1-Methylcyclopropyl¹ | Ex 20 | a |

¹equivalent of triethylamine added
Notes
a The product gave the following data; NMR Spectrum: (DMSOd₆) 0.57 (m, 2 H), 0.71 (m, 2 H), 1.35 (s, 3 H), 2.09 (s, 3 H), 6.64 (d, 1 H), 7.10 (d, 1 H), 7.23 (dd, 1 H), 7.45 (d, 1 H), 7.59 (m, 3 H), 7.72 (s, 1 H), 7.83 (d, 1 H), 8.63 (s, 1 H), 9.98 (s, 1 H); Mass Spectrum: M + H⁺ 349.

The (1-methylcyclopropyl)amine hydrochloride used as starting material was prepared as follows:—

Diphenylphoshoryl azide (10.5 ml) was added to a stirred mixture of 1-methylcyclopropane carboxylic acid (4.88 g) and triethylamine (6.8 ml) in anhydrous tert-butanol (100 ml) under an argon atmosphere. The mixture was heated to 50° C. and stirred for 15 minutes. The reaction mixture was then heated to 100° C. and stirred for 16 hours. The reaction mixture was evaporated, dissolved in diethyl ether and washed with a saturated NaHCO₃ solution, water and dried (magnesium sulfate) to give tert-butyl(1-methylcyclopropyl) carbamate as a solid (3.61 g); NMR Spectrum: (DMSOd₆) 0.45 (m; 2H), 0.58 (m, 2H), 1.22 (s, 3H), 1.37 (s, 9H), 7.01 (s, 1H).

tert-Butyl(1-methylcyclopropyl)carbamate (3.60 g) was dissolved in 10% HCl in methanol (20 ml) and heated to 50° C. for 6 hours. The reaction mixture was evaporated in vacuo and diethyl ether added. The mixture was evaporated to give (1-methylcyclopropyl)amine hydrochloride as a solid (2.24 g); NMR Spectrum: (DMSOd₆) 0.60 (m, 2H), 0.92 (m, 2H), 1.35 (s, 3H), 8.45 (s, 3H).

EXAMPLE 22

3-[7-[3-(Dimethylamino)propyl]-1-oxoisoquinolin-2(1H)-yl]-N-isoxazol-3-yl-4-methylbenzamide To a suspension of 3-[7-[3-(dimethylamino)propyl]-1-oxoisoquinolin-2(1H)-yl]-4-methylbenzoic acid (151 mg) in methylene chloride (3 ml) was cooled to 0° C. and oxalyl chloride (72 µl) was added. After the addition of DMF (25 µl), the reaction mixture was stirred at room temperature for 2 hours, 3-aminoisoxazole (153 µl) was added and stirring continued at room temperature for 2.5 hours. The reaction mixture was dissolved in methanol and water and purified by column chromatography on an ion exchange column (isolute SCX column from International Sorbent Technology Limited, Henoed, Mid-Glamorgan, UK) using initially methanol and then a 99:1 mixture of methanol and aqueous ammonia solution yielded an orange oil. The oil was triturated with water resulted in a solid which was collected by filtration washed with diethyl ether and air dried to give 3-[7-[3-(dimethylamino)propyl]-1-oxoisoquinolin-2(1H)-yl]-N-isoxazol-3-yl-4-methylbenzamide as a tan solid (124 mg); NMR Spectrum: (DMSOd₆) 0.57 (m, 2H), 0.71 (m, 2H), 1.35 (s, 3H), 2.09 (s, 3H), 6.64 (d, 1H), 7.10 (d, 1H), 7.23 (m, 1H), 7.45 (d, 1H), 7.59 (m, 3H), 7.72 (s, 1H), 7.83 (d, 1H), 8.63 (s, 1H), 9.98 (s, 1H); Mass Spectrum: M+H⁺ 349.

3-[7-[3-(Dimethylamino)propyl]-1-oxoisoquinolin-2(1H)-yl]-4-methylbenzoic acid used as starting material was prepared as follows:—

A mixture of the methyl 4-methyl-3-[1-oxo-7-{[(trifluoromethyl)sulfonyl]oxy} isoquinolin-2(1H)-yl]benzoate (284 mg), PdCl₂(PPh₃)₂ (13 mg), CuI (6 mg) and triethylamine (449 µl) were stirred in acetonitrile (4.2 ml) for 20 minutes. 1-Dimethylamino-2-propyne (69 µl) in acetonitrile (2.8 mL) was added dropwise and the reaction was stirred at 80° C. for 22 hours. LiCl (81 mg) was added and stirring continued at 80° C. for 1.5 hours. PdCl₂(PPh₃)₂ (13 mg), CuI (6 mg) and 1-dimethylamino-2-propyne (69 µl) was added and stirring continued for a further 22 hours. The reaction mixture was concentrated and the residue was dissolved in ethyl acetate, washed with water (×5), brine, dried (magnesium sulfate), and concentrated to an oil. Purification by column chromatography on a silica column eluting using a gradient of ethyl acetate to 10% methanol/ethyl acetate gave methyl 3-[7-[3-(dimethylamino)prop-1-yn-1-yl]-1-oxoisoquinolin-2(1H)-yl]-4-methylbenzoate as a light brown solid (126 mg); NMR Spectrum: (DMSOd₆) 2.15 (s, 3H), 2.27 (s, 6H), 3.52 (s, 2H), 3.86 (s, 3H), 6.79 (d, 1H), 7.43 (d, 1H), 7.60 (d, 1H), 7.79 (m, 2H), 7.87 (s, 1H), 7.99 (d, 1H), 8.23 (s, 1H); Mass Spectrum: M+H⁺ 375.

Methyl 3-[7-[3-(dimethylamino)prop-1-yn-1-yl]-1-oxoisoquinolin-2(1H)-yl]-4-methylbenzoate (192 mg) and 10% Pd/C (20 mg) were stirred in a mixture of ethanol (2 ml)/methanol (4 ml)/ethyl acetate (1 ml) under an atmosphere of hydrogen at room temperature for 2 hours. The catalyst was removed by filtration through a microfibre filter and the filtrate was concentrated to yield an oil. The oil was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to yield methyl 3-[7-[3-(dimethylamino)propyl]-1-oxoisoquinolin-2(1H)-yl]-4-methylbenzoate as a yellow oil that turned to a pale yellow solid on standing (155 mg); NMR Spectrum: (DMSOd$_6$) 1.76 (m, 2H), 2.14 (s, 6H), 2.15 (s, 3H), 2.23 (t, 2H), 2.76 (t, 2H), 3.87 (s, 3H), 6.72 (d, 1H), 7.30 (d, 1H), 7.59 (d, 1H), 7.67 (m, 2H), 7.83 (s, 1H), 7.98 (d, 1H), 8.07 (s, 1H); Mass Spectrum: M+H$^+$ 379.

Methyl 3-[7-[3-(dimethylamino)propyl]-1-oxoisoquinolin-2(1H)-yl]-4-methylbenzoate (176 mg) was stirred in a solution of methanol (2 ml) and 1N NaOH solution (0.57 ml) at 65° C. for 1 hour and then neutralised with 2N HCl (0.28 ml). The reaction mixture was concentrated and the residue was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to yield 3-[7-[3-(dimethylamino)propyl]-1-oxoisoquinolin-2(1H)-yl]-4-methylbenzoic acid as a cream coloured solid (155 mg); NMR Spectrum: (DMSOd$_6$) 1.81 (m, 2H), 2.12 (s, 3H), 2.24 (s, 6H), 2.38 (t, 2H), 2.76 (t, 2H), 6.71 (d, 1H), 7.29 (d, 1H), 7.51 (d, 1H), 7.66 (m, 2H), 7.76 (s, 1H), 7.94 (d, 1H), 8.08 (s, 1H); Mass Spectrum: M+H$^+$ 365.

EXAMPLE 23

N-Isoxazol-3-yl-4-methyl-3-[7-(3-morpholin-4-ylpropyl)-1-oxoisoquinolin-2(1H)-yl]benzamide To a suspension of 4-methyl-3-[7-(3-morpholin-4-ylpropyl)-1-oxoisoquinolin-2(1H)-yl]benzoic acid (140 mg) in methylene chloride (3 ml) was cooled to 0° C. and oxalyl chloride (59 µl) was added. After the addition of DMF (25 µl), the reaction mixture was stirred at room temperature for 2 hours, 3-aminoisoxazole (126 µl) was added and stirring continued at room temperature for 3.5 hours. The reaction mixture was dissolved in methanol and water and purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to give a brown oil. The oil was dissolved in ethyl acetate and the insoluble material was removed by filteration. The filtrate was washed with water, brine, dried (magnesium sulfate) and concentrated to a brown oil. Purification by column chromatography on a silica column eluting using a gradient of ethyl acetate to 10% methanol/ethyl acetate gave N-isoxazol-3-yl-4-methyl-3-[7-(3-morpholin-4-ylpropyl)-1-oxoisoquinolin-2(1H)-yl]benzamide as a yellow foam (55 mg); NMR Spectrum: (DMSOd$_6$) 1.80 (m, 2H), 2.15 (s, 3H), 2.28-2.36 (m, 6H), 2.78 (t, 2H), 3.58 (t, 4H), 6.75 (d, 1H), 7.05 (s, 1H), 7.33 (d, 1H), 7.59 (d, 1H), 7.68 (m, 2H), 8.01 (s, 1H), 8.06 (d, 1H), 8.10 (s, 1H), 8.85 (s, 1H), 11.47 (s, 1H); Mass Spectrum: M+H$^+$ 473.

4-Methyl-3-[7-(3-morpholin-4-ylpropyl)-1-oxoisoquinolin-2(1H)-yl]benzoic acid used as starting material was prepared as follows:—

To a mixture of cesium carbonate (1.6 g) and morpholine (0.437 ml) in acetone (10 ml) was added propargyl bromide (557 µl of 80% wt. in toluene) dropwise. The mixture was stirred at room temperature for 18 hours. The insoluble material was removed by filtration and the filtrate concentrated. The residue dissolved in ethyl acetate, washed with saturated NaHCO$_3$ solution, dried (magnesium sulfate) and concentrated to yield 3-(4-morpholinyl)-1-propyne as a brown oil (494 mg); NMR Spectrum: (DMSOd$_6$) 2.19 (t, 1H), 2.50 (m, 4H), 3.22 (d, 2H), 3.67 m, 4H).

A mixture of the methyl 4-methyl-3-[1-oxo-7-{[(trifluoromethyl)sulfonyl]oxy} isoquinolin-2(1H)-yl]benzoate (400 mg), PdCl$_2$(PPh$_3$)$_2$ (16 mg), CuI (9 mg) and triethylamine (632 µl) were stirred in acetonitrile (10 ml) for 10 minutes. 3-(4-morpholinyl)-1-propyne (114 mg) in acetonitrile (4 ml) was then added dropwise and the reaction was heated at 80° C. for 18 hours and then concentrated. The residue was dissolved in ethyl acetate, washed with water (×3), brine, dried (magnesium sulfate) and concentrated to a brown oil. The oil was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to yield methyl 3-[7-[3-(dimethylamino)propyl]-1-oxoisoquinolin-2(1H)-yl]-4-methylbenzoate as a brown oil (298 mg); NMR Spectrum: (DMSOd$_6$) 2.15 (s, 3H), 2.55 (m, 4H), 3.57 (s, 2H), 3.63 (m, 4H), 3.87 (s, 3H), 6.78 (d, 1H), 7.42 (d, 1H), 7.60 (d, 1H), 7.79 (m, 2H), 7.86 (s, 1H), 7.99 (d, 1H), 8.24 (s, 1H); Mass Spectrum: M+H$^+$ 417.

Methyl 4-methyl-3-[7-(3-morpholin-4-ylprop-1-yn-1-yl)-1-oxoisoquinolin-2(1H)-yl]benzoate (292 mg) and 10% Pd/C (30 mg) were stirred in a mixture of ethanol (2 ml)/methanol (4 ml)/ethyl acetate (2 ml) under an atmosphere of hydrogen at room temperature for 17 hours. The catalyst was removed by filtration through a microfibre filter and the filtrate was concentrated to yield an oil. The oil was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to yield methyl 3-[7-[3-(dimethylamino)propyl]-1-oxoisoquinolin-2(1H)-yl]-4-methylbenzoate as a brown oil (242 mg); NMR Spectrum: (DMSOd$_6$) 1.79 (m, 2H), 2.14 (s, 3H), 2.28-2.36 (m, 6H), 2.77 (t, 2H), 3.57 (m, 4H), 3.86 (s, 3H), 6.72 (d, 1H), 7.30 (d, 1H), 7.59 (d, 1H), 7.67 (m, 2H), 7.83 (s, 1H), 7.98 (d, 1H), 8.08 (s, 1H); Mass Spectrum: M+H$^+$ 421.

Methyl 4-methyl-3-[7-(3-morpholin-4-ylpropyl)-1-oxoisoquinolin-2(1H)-yl]benzoate (238 mg) was stirred in methanol (2 ml) and 1N NaOH solution (0.69 ml) at 65° C. for 1 hour and then neutralised with 2N HCl (0.35 ml). The reaction mixture was concentrated and the residue was purified by column chromatography on an ion exchange column (isolute SCX column from International Sorbent Technology Limited, Henoed, Mid-Glamorgan, UK) using initially methanol and then a 99:1 mixture of methanol and aqueous ammonia solution to yield a brown oily solid. The solid was triturated with ethyl acetate to yield methyl 4-methyl-3-[7-(3-morpholin-4-ylpropyl)-1-oxoisoquinolin-2(1H)-yl]benzoate as a light brown solid (196 mg); NMR Spectrum: (DMSOd$_6$) 11.79 (m, 2H), 2.12 (s, 3H), 2.32 (m, 6H), 2.77 (t, 2H), 3.57 (m, 4H), 6.71 (d, 1H), 7.29 (d, 1H), 7.52 (d, 1H), 7.67 (m, 2H), 7.76 (s, 1H), 7.94 (d, 1H), 8.08 (s, 1H); Mass Spectrum: M+H⁺ 407.

EXAMPLE 24

N-Cyclopropyl-3-[7-{2-[isopropyl(methyl)amino]ethoxy}-4-methyl-1-oxoisoquinolin-2(1H)-yl]-4-methylbenzamide A mixture of 3-[7-(2-chloroethoxy)-4-methyl-1-oxoisoquinolin-2(1H)-yl]-N-cyclopropyl-4-methylbenzamide and 3-[7-(2-bromoethoxy)-4-methyl-1-oxoisoquinolin-2(1H)-yl]-N-cyclopropyl-4-methylbenzamide (4:1, 225 mg), potassium iodide (182 mg), and N-methylisopropylamine (0.34 ml) were stirred in DMA (3 ml) and heated under microwave irradiation conditions (Personal Chemistry Emrys Optimizer with 300 W magnetron) at 150° C. for 1 hour. The reaction mixture was diluted with ethyl acetate and washed with water (×5), brine (×2), dried (magnesium sulfate) and concentrated. Purification by column chromatography on a silica column eluting using initially 10% methanol/ethyl acetate and then a 99:1 mixture of 10% methanol/ethyl acetate and aqueous ammonia solution gave N-cyclopropyl-3-[7-{2-[isopropyl(methyl)amino]ethoxy}-4-methyl-1-oxoisoquinolin-2(1H)-yl]-4-methylbenzamide (105 mg) as a pale yellow foam; NMR Spectrum: (DMSOd₆) 0.56 (m, 2H), 0.69 (m, 2H), 0.97 (d, 6H), 2.10 (s, 3H), 2.24 (s, 3H), 2.27 (s, 3H), 2.76 (t, 2H), 2.80-2.89 (m, 2H), 4.14 (m, 2H), 7.09 (s, 1H), 7.45-7.51 (m, 2H), 7.70-7.75 (m, 3H), 7.86 (d, 1H), 8.45 (d, 1H); Mass Spectrum: M+H⁺ 448.

The mixture of 3-[7-(2-chloroethoxy)-4-methyl-1-oxoisoquinolin-2(1H)-yl]-N-cyclopropyl-4-methylbenzamide and 3-[7-(2-bromoethoxy)-4-methyl-1-oxoisoquinolin-2(1H)-yl]-N-cyclopropyl-4-methylbenzamide (4:1 mixture) used as starting material was prepared as follows:—

To a solution of 3-amino-N-cyclopropyl-4-methylbenzamide (2 g) in acetonitrile (10 ml) was added with potassium carbonate (2.6 g). The mixture was heated to 80° C. and a solution of allyl bromide (1.1 ml) in acetonitrile (6 ml) was added dropwise and heating was continued for 17 hours. The insoluble material was removed by filtration. The filtrate was concentrated and the residue was recrystallised from 50% ethyl acetate/hexane. The mother liquors was concentrated and by column chromatography on a silica column eluting using a gradient of iso-hexane to 50% ethyl acetate/iso-hexane to yield 3-(allylamino)-N-cyclopropyl-4-methylbenzamide as a colourless oil which solidified to a white solid (688 mg); NMR Spectrum: (DMSOd₆) 0.53 m, 2H), 0.78 (m, 2H), 2.10 (s, 3H), 2.81 (m, 1H), 3.67 (s, 1H), 3.81 (d, 2H), 5.13 (d, 1H), 5.23 (d, 1H), 5.93 (m, 1H), 6.11 (s, 1H), 6.83 (d, 1H), 6.98 (m, 2H); Mass Spectrum: M+H⁺ 231.

3-(Allylamino)-N-cyclopropyl-4-methylbenzamide (688 mg) was stirred with 2-bromo-5-methoxybenzene-1-carbonyl chloride (745 mg) and triethylamine (0.83 ml) in THF (10 ml) at room temperature for 2.5 hours and then concentrated. The residue was dissolved in ethyl acetate and washed with 1N HCl (×2), water, brine, dried (magnesium sulfate) and concentrated to yield N-allyl-2-bromo-N-{5-[(cyclopropylamino)carbonyl]-2-methylphenyl}-5-methoxybenzamide as a pale orange solid (1.24 g); Mass Spectrum: M+H⁺ 443.

N-allyl-2-bromo-N-{5-[(cyclopropylamino)carbonyl]-2-methylphenyl}-5-methoxybenzamide (1.03 g), tri-o-tolylphosphine (283 mg), tetraethylammonium bromide (977 mg) and potassium carbonate (1.3 g) were suspended in DMF (36 ml) under argon. Pd(OAc)₂ (104 mg) was added and the mixture was heated at 120° C. for 17 hours and then allowed to cool. The reaction mixture was diluted with ethyl acetate and washed with water (×5), brine, dried (magnesium sulfate) and concentrated. Purification by column chromatography on a silica column eluting using a gradient of 50% ethyl acetate/iso-hexane to 100% ethyl acetate/iso-hexane to yield N-cyclopropyl-3-(7-methoxy-4-methyl-1-oxoisoquinolin-2(1H)-yl)-4-methylbenzamide as a pale yellow foam (265 mg); NMR Spectrum: (DMSOd₆) 0.56 (m, 2H), 0.69 (m, 2H), 2.11 (s, 3H), 2.27 (s, 3H), 2.86 (m, 1H), 3.89 (s, 3H), 7.10 (s, 1H), 7.46-7.51 (m, 2H), 7.71-7.76 (m, 3H), 7.87 (d, 1H), 8.46 (d, 1H); Mass Spectrum: M+H⁺ 363.

N-cyclopropyl-3-(7-methoxy-4-methyl-1-oxoisoquinolin-2(1H)-yl)-4-methylbenzamide (262 mg, 0.72 mmol) and lithium iodide (174 mg) were stirred in 2,4,6-collidine (3 ml) and heated under microwave irradiation conditions (Personal Chemistry Emrys Optimizer with 300 W magnetron) at 200° C. for 1.5 hour and then allowed to cool. The reaction mixture was dissolved in 2N NaOH and then re-acidified with 2N HCl solution. The aqueous phase was extracted with ethyl acetate (×4) and the combined organic layers were concentrated. The residue was triturated with 1N HCl, the solid was collected by filtration, washed with water, diethyl ether, and air dried to give N-cyclopropyl-3-(7-hydroxy-4-methyl-1-oxoisoquinolin-2(1H)-yl)-4-methylbenzamide as an off white solid (207 mg); NMR Spectrum: (DMSOd₆) 0.56 (m, 2H), 0.69 (m, 2H), 2.09 (s, 3H), 2.24 (s, 3H), 2.86 (m, 1H), 7.00 (s, 1H), 7.31 (d, 1H), 7.48 (d, 1H), 7.62-7.65 (m, 2H), 7.74 (s, 1H), 7.85 (d, 1H), 8.45 (d, 1H), 10.04 (s, 1H); Mass Spectrum: M+H⁺ 349.

N-Cyclopropyl-3-(7-hydroxy-4-methyl-1-oxoisoquinolin-2(1H)-yl)-4-methylbenzamide (204 mg), 1-bromo-2-chloroethane (0.24 ml) and potassium carbonate (809 mg) were heated to 50° C. in DMF (9 ml) for 20 hours. The reaction mixture was diluted in ethyl acetate and washed with water (×5), 1N NaOH (×2), brine (×2), dried (magnesium sulfate) and concentrated to a cream coloured foam solid (230 mg) identified as mixture (4:1) of 3-[7-(2-chloroethoxy)-4-methyl-1-oxoisoquinolin-2(1H)-yl]-N-cyclopropyl-4-methylbenzamide; NMR Spectrum: (DMSOd₆) 0.56 (m, 2H), 0.69 (m, 2H), 2.10 (s, 3H), 2.27 (s, 3H), 2.86 (m, 1H), 4.01 (t, 2H), 4.41 (m, 2H), 7.12 (s, 1H), 7.49-7.53 (m, 2H), 7.73-7.75 (m, 3H), 7.87 (d, 1H), 8.46 (d, 1H); Mass Spectrum: M+H⁺ 411 and 3-[7-(2-bromoethoxy)-4-methyl-1-oxoisoquinolin-2(1H)-yl]-N-cyclopropyl-4-methylbenzamide; NMR Spectrum: (DMSOd₆) 0.56 (m, 2H), 0.69 (m, 2H), 2.10 (s, 3H), 2.27 (s, 3H), 2.86 (m, 1H), 3.87 (t, 2H), 4.47 (m, 2H), 7.12 (s, 1H), 7.49-7.53 (m, 2H), 7.73-7.75 (m, 3H), 7.87 (d, 1H), 8.46 (d, 1H); Mass Spectrum: M+H⁺ 455.

EXAMPLE 25

N-Ethyl-3-[7-{2-[isopropyl(methyl)amino]ethoxy}-4-methyl-1-oxoisoquinolin-2(1H)-yl]-4-methylbenzamide A mixture of 3-[7-(2-chloroethoxy)-4-methyl-1-oxoisoquinolin-2(1H)-yl]-N-ethyl-4-methylbenzamide (90 mg), potassium iodide (75 mg), and N-methylisopropylamine (0.14 ml) were stirred in DMA (2 ml) and heated under microwave irradiation conditions (Personal Chemistry Emrys Optimizer with 300 W magnetron) at 150° C. for 1 hour. The reaction mixture was diluted with ethyl acetate and washed with water (×5), brine (×2), dried (magnesium sulfate) and concentrated. Purification by column chromatography on a silica column eluting using initially 10% methanol/ethyl acetate and then a 99:1 mixture of 110% methanol/ethyl acetate and aqueous ammonia solution gave N-ethyl-3-[7-{2-[isopropyl(methyl)amino]ethoxy}-4-methyl-1-oxoisoquinolin-2(1H)-yl]-4-methylbenzamide (68 mg) as a cream solid; NMR Spectrum: (DMSOd$_6$) 0.98 (d, 6H), 1.12 (t, 3H), 2.11 (s, 3H), 2.25 (s, 3H), 2.27 (s, 3H), 2.78 (t, 2H), 2.85 (m, 1H), 3.29 (m, 2H), 4.15 (m, 2H), 7.10 (s, 1H), 7.45-7.51 (m, 2H), 7.70-7.77 (m, 3H), 7.88 (d, 1H), 8.47 (t, 1H); Mass Spectrum: M+H$^+$ 436.

3-[7-(2-Chloroethoxy)-4-methyl-1-oxoisoquinolin-2 (1H)-yl]-N-ethyl-4-methylbenzamide used as starting material was prepared as follows:—

Methyl 3-amino-4-methylbenzoate (3.18 g), 2-bromo-5-methoxybenzene-1-carbonyl chloride (4.8 g) and triethylamine (5.4 ml) in THF (45 ml) were stirred at room temperature for 2.5 hour and then concentrated. The residue was dissolved in ethyl acetate and washed with 1N HCl, water, brine, dried (magnesium sulfate) and concentrated. The residue was recrystallised from hot ethyl acetate, washed with ether, and air dried to yield methyl 3-[(2-bromo-5-methoxybenzoyl)amino]-4-methylbenzoate as a white solid (5.36 g); NMR Spectrum: (DMSOd$_6$) 2.39 (s, 3H), 3.83 (s, 3H), 3.87 (s, 3H), 7.02 (m, 1H), 7.23 (d, 1H), 7.42 (d, 1H), 7.60 (d, 1H), 7.75 (m, 1H), 8.12 (s, 1H), 10.06 (s, 1H); Mass Spectrum: M+H$^+$ 377.

To a slurry of NaH (680 mg [60% dispersion in oil]) in THF (250 ml) at 0° C. was added methyl 3-[(2-bromo-5-methoxybenzoyl)amino]-4-methylbenzoate (5.36 g) portionwise. The reaction was stirred for 30 minutes at room temperature when allyl bromide (1.6 ml) was added dropwise and the solution was stirred for a further 20 hours at room temperature. The reaction mixture was quenched with water and then concentrated. The residue was dissolved in ethyl acetate and washed with water (×2), brine, dried (magnesium sulfate) and concentrated. The residue was purified by column chromatography on a silica column eluting using a gradient of iso-hexane to 50% ethyl acetate/iso-hexane to yield methyl 3-[allyl(2-bromo-5-methoxybenzoyl)amino]-4-methylbenzoate as a colourless oil (4.88 g); Mass Spectrum: M+H$^+$ 417.

Methyl 3-[allyl(2-bromo-5-methoxybenzoyl)amino]-4-methylbenzoate (4.88 g), tri-o-tolylphosphine (1.425 g, 4.67 mmol), tetraethylammonium bromide (4.91 g) and potassium carbonate (6.46 g) were suspended in DMF (180 ml) under argon. Pd(OAc)$_2$ (524 mg) was added and the mixture was heated at 120° C. for 17 hours and then allowed to cool. The reaction mixture was diluted with ethyl acetate and washed with water (×5), brine, dried (magnesium sulfate), and concentrated. The residue was purified by column chromatography on a silica column eluting using a gradient of iso-hexane to 30% ethyl acetate/iso-hexane to yield a yellow solid (2.64 g). This solid was stirred in 48% hydrobromic acid (12 ml) and acetic acid (12 ml) and heated under microwave irradiation conditions (Personal Chemistry Emrys Optimizer with 300 W magnetron) at 150° C. for 1 hour. The reaction mixture was diluted with ethyl acetate and washed with water (×3), brine, dried (magnesium sulfate) and concentrated. The residue was triturated with diethyl ether to yield 3-(7-hydroxy-4-methyl-1-oxoisoquinolin-2(1H)-yl)-4-methylbenzoic acid as a brown solid (1.88 g); NMR Spectrum: (DMSOd$_6$) 2.13 (s, 3H), 2.24 (s, 3H), 7.02 (s, 1H), 7.31 (d, 1H), 7.55 (d, 1H), 7.61-7.65 (m, 2H), 7.76 (s, 1H), 7.94 (d, 1H), 10.05 (s, 1H), 12.89 (s, 1H); Mass Spectrum: M+H$^+$ 310.

A solution of 3-(7-hydroxy-4-methyl-1-oxoisoquinolin-2 (1H)-yl)-4-methylbenzoic acid (570 mg), potassium carbonate (2.5 g) and 1-bromo-2-chloroethane (0.9 ml) in DMF (13 ml) and heated at 50° C. for 41 hours. The reaction mixture was cooled to 40° C. and 2N NaOH solution (8 ml) was added and the reaction mixture was stirred for 1.5 hours. The reaction mixture was allowed to cool and then adjusted to pH 1 using 1N HCl, the resulting solid was collected by filtration and washed with diethyl ether to yield 3-[7-(2-chloroethoxy)-4-methyl-1-oxoisoquinolin-2(1H)-yl]-4-methylbenzoic acid as a brown solid (426 mg); NMR Spectrum: (DMSOd$_6$) 1.14 (s, 3H), 2.27 (s, 3H), 4.01 (t, 2H), 4.41 (m, 2H), 7.14 (s, 1H), 7.50-7.57 (m, 2H), 7.73-7.78 (m, 3H), 7.96 (d, 1H), 13.05 (br s, 1H); Mass Spectrum: M+H$^+$ 372.

A suspension of 3-[7-(2-chloroethoxy)-4-methyl-1-oxoisoquinolin-2(1H)-yl]-4-methylbenzoic acid (425 mg) in methylene chloride (8 ml) was cooled to 0° C. and oxalyl chloride (0.2 ml) was added followed by DMF (10 µL) and the reaction mixture was left to stir at room temperature for 1 hour when N,N'-diisopropylethylamine (0.8 ml) and ethylamine (2.28 ml of a 2.0M in THF) were added. The reaction mixture was stirred at room temperature for 17 hours and concentrated. The residue was diluted with ethyl acetate and washed with water (×3), brine, dried (magnesium sulfate) and concentrated to a brown foam which was purified by column chromatography on a silica column eluting using a gradient of iso-hexane to ethyl acetate to give 3-[7-(2-chloroethoxy)-4-methyl-1-oxoisoquinolin-2(1H)-yl]-N-ethyl-4-methylbenzamide as a pale yellow solid (323 mg); NMR Spectrum: (DMSOd$_6$) 1.11 (t, 3H), 2.11 (s, 3H), 2.27 (s, 3H), 3.28 (m, 2H), 4.01 (t, 2H), 4.41 (m, 2H), 7.13 (s, 1H), 7.52 (m, 2H), 7.73-7.78 (m, 3H), 7.89 (d, 1H), 8.50 (t, 1H); Mass Spectrum: M+H$^+$ 399.

EXAMPLE 26

Using an analogous procedure to that described in Example 25, 3-[7-(2-chloroethoxy)-4-methyl-1-oxoisoquinolin-2(1H)-yl]-N-ethyl-4-methylbenzamide was reacted with the appropriate amine or appropriate amine salt to give the compounds described in Table 7.

TABLE 7

| R | Method | Note |
|---|---|---|
| Ethyl(methyl)amino | Ex 25 | a |
| Dimethylamino | Ex 25 | b |

Notes
a The product gave the following data; NMR Spectrum: (DMSOd$_6$) 1.00 (t, 3 H), 1.11 (t, 3 H), 2.11 (s, 3 H), 2.25 (s, 3 H), 2.27 (s, 3 H), 2.47 (q, 2 H), 2.76 (t, 2 H), 3.28 (m, 2 H), 4.18 (m, 2 H), 7.11 (s, 1 H), 7.46-7.51 (m, 2 H), 7.70-7.77 (m, 3 H), 7.88 (d, 1 H), 8.50 (t, 1 H); Mass Spectrum: M + H$^+$ 422.
b The product gave the following data; NMR Spectrum: (DMSOd$_6$) 1.11 (t, 3 H), 2.11 (s, 3 H), 2.24 (s, 6 H), 2.27 (s, 3 H), 2.68 (t, 2 H), 3.29 (m, 2 H), 4.19 (m, 2 H), 7.11 (s, 1 H), 7.46-7.51 (m, 2 H), 7.71-7.77 (m, 3 H), 7.88 (d, 1 H), 8.50 (t, 1 H); Mass Spectrum: M + H$^+$ 408.

EXAMPLE 27

N-Cyclobutyl-3-[7-{2-[isopropyl(methyl)amino] ethoxy}-4-methyl-1-oxoisoquinolin-2(1H)-yl]-4-methylbenzamide A mixture of 3-[7-(2-chloroethoxy)-4-methyl-1-oxoisoquinolin-2(1H)-yl]-N-cyclobutyl-4-methylbenzamide (131 mg), potassium iodide (102 mg), and N-methylisopropylamine (0.19 ml) were stirred in DMA (2 ml) and heated under microwave irradiation conditions (Personal Chemistry Emrys Optimizer with 300 W magnetron) at 150° C. for 1 hour. The reaction mixture was diluted with ethyl acetate and washed with water (×5), brine (×2), dried (magnesium sulfate) and concentrated. Purification by column chromatography on a silica column eluting using initially 10% methanol/ethyl acetate and then a 99:1 mixture of 10% methanol/ethyl acetate and aqueous ammonia solution gave N-cyclobutyl-3-[7-{2-[isopropyl(methyl)amino]ethoxy}-4-methyl-1-oxoisoquinolin-2(1H)-yl]-4-methylbenzamide (74 mg) as a cream solid; NMR Spectrum: (DMSOd$_6$) 0.98 (d, 6H), 1.68 (m, 2H), 2.06 (m, 2H), 2.11 (s, 3H), 2.21 (m, 2H), 2.25 (s, 3H), 2.28 (s, 3H), 2.77 (t, 2H), 2.84 (m, 1H), 4.15 (m, 2H), 4.43 (m, 1H), 7.09 (s, 1H), 7.45-7.51 (m, 2H), 7.71-7.74 (m, 2H), 7.80 (s, 1H), 7.89 (d, 1H), 8.60 (d, 1H); Mass Spectrum: M+H$^+$ 462.

3-[7-(2-Chloroethoxy)-4-methyl-1-oxoisoquinolin-2(1H)-yl]-N-cyclobutyl-4-methylbenzamide used as starting material was prepared as follows:—

A suspension of 3-[7-(2-chloroethoxy)-4-methyl-1-oxoisoquinolin-2(1H)-yl]-4-methylbenzoic acid (550 mg) in methylene chloride (10 ml) was cooled to 0° C. and oxalyl chloride (0.26 ml) was added followed by DMF (10 µl) and the reaction mixture was left to stir at room temperature for 1 hour when N,N'-diisopropylethylamine (1.03 ml) and cyclobutylamine (0.51 ml) were added. The reaction mixture was stirred at room temperature for 4 hours and concentrated. The residue was diluted with ethyl acetate and washed with water (×3), brine, dried (magnesium sulfate) and concentrated to a brown foam which was purified by column chromatography on a silica column eluting using a gradient of iso-hexane to ethyl acetate to give 3-[7-(2-chloroethoxy)-4-methyl-1-oxoisoquinolin-2(1H)-yl]-N-cyclobutyl-4-methylbenzamide as a pale yellow solid (397 mg); NMR Spectrum: (DMSOd$_6$) 1.66 (m, 2H), 2.06 (m, 2H), 2.12 (s, 3H), 2.21 (m, 2H), 2.28 (s, 3H), 4.01 (t, 2H), 4.38-4.46 (m, 3H), 7.12 (s, 1H), 7.49-7.54 (m, 2H), 7.74-7.76 (m, 2H), 7.81 (s, 1H), 7.89 (d, 1H), 8.60 (d, 1H); Mass Spectrum: M$^+$ 425.

EXAMPLE 28

Using an analogous procedure to that described in Example 25, 3-[7-(2-chloroethoxy)-4-methyl-1-oxoisoquinolin-2(1H)-yl]-N-cyclobutyl-4-methylbenzamide was reacted with the appropriate amine or appropriate amine salt to give the compounds described in Table 8.

TABLE 8

| R | Method | Note |
|---|---|---|
| Ethyl(methyl)amino | Ex 27 | a |
| Dimethylamino | Ex 27 | b |

Notes
a The product gave the following data; NMR Spectrum: (DMSOd$_6$) 1.01 (t, 3 H), 1.68 (m, 2 H), 2.05 (m, 2 H), 2.12 (s, 3 H), 2.21 (m, 2 H), 2.26 (s, 3 H), 2.28 (s, 3 H), 2.47 (q, 2 H), 2.76 (t, 2 H), 4.19 (m, 2 H), 4.43 (m, 1 H), 7.09 (s, 1 H), 7.46-7.51 (m, 2 H), 7.71-7.74 (m, 2 H), 7.80 (s, 1 H), 7.89 (d, 1 H), 8.60 (d, 1 H); Mass Spectrum: M + H$^+$ 448.
b The product gave the following data; NMR Spectrum: (DMSOd$_6$) 1.72 (m, 2 H), 2.10 (m, 2 H), 2.17 (s, 3 H), 2.26 (m, 2 H), 2.30 (s, 6 H), 2.33 (s, 3 H), 2.74 (t, 2 H), 4.24 (m, 2 H), 4.48 (m, 1 H), 7.15 (s, 1 H), 7.51-7.56 (m, 2 H), 7.76-7.79 (m, 2 H), 7.86 (s, 1 H), 7.94 (d, 1 H), 8.65 (d, 1 H); Mass Spectrum: M + H$^+$ 434.

EXAMPLE 29

N-Cyclopropyl-3-[4-(hydroxymethyl)-7-methoxy-1-oxoisoquinolin-2(1H)-yl]-4-methylbenzamide The isoquinolinone (100 mg) was stirred in aqueous formaldehyde (226 µl) and formic acid (2 ml) at 90° C. for 3.5 hours. The reaction mixture was concentrated and partitioned between ethyl acetate and 2N NaOH. The organic layer was washed with 2N NaOH (×2), brine and concentrated. The residue was dissolved in methanol and 2N NaOH and stirred for 60 hours, the methanol removed by distillation, the aqueous solution neutralised with 2N HCl and extracted with ethyl acetate (×3). The combined organic layers were washed with brine, dried (magnesium sulfate) and concentrated. Purification by column chromatography on a silica column eluting using a gradient of 50% ethyl acetate/iso-hexane to ethyl acetate gave N-cyclopropyl-3-[4-(hydroxymethyl)-7-methoxy-1-oxoisoquinolin-2(1H)-yl]-4-methylbenzamide as a white solid (15 mg); NMR Spectrum: (DMSOd$_6$) 0.56 (m, 2H), 0.69 (m, 2H), 2.11 (s, 3H), 2.86 (m, 1H), 3.89 (s, 3H), 4.61 (d, 2H), 5.15 (t, 1H), 7.17 (s, 1H), 7.45-7.52 (m, 2H), 7.71 (d, 1H), 7.75 (s, 1H), 7.86-7.89 (m, 2H), 8.48 (d, 1H); Mass Spectrum: M+H$^+$ 379.

EXAMPLE 30

3-[7-[2-(Isopropylmethylamino)ethoxy]-1-oxoisoquinolin-2(1H)-yl]-N-ethyl-4-methylbenzamide 3-[7-(2-Chloroethoxy)-1-oxoisoquinolin-2(1H)-yl]-N-ethyl-4-methylbenzamide (150 mg), potassium iodide (129 mg) and methylisopropylamine (244 µL, 2.34 mmol) were stirred in DMA (3 ml) and heated under microwave irradiation conditions (Personal Chemistry Emrys Optimizer with 300 W magnetron) at 150° C. for 1 hour. The reaction mixture was diluted with ethyl acetate and washed with water (×5), brine (×2), dried (magnesium sulfate) and concentrated. Purification by column chromatography on a silica column eluting using initially 10% methanol/ethyl acetate and then a 99:1 mixture of 10% methanol/ethyl acetate and aqueous ammonia solution gave 3-[7-[2-(Isopropylmethylamino)ethoxy]-1-oxoisoquinolin-2(1H)-yl]-N-ethyl-4-methylbenzamide as a foam (104 mg); NMR Spectrum: (DMSO d$_6$) 0.97 (d, 6H), 1.12 (t, 3H), 2.11 (s, 3H), 2.23 (s, 3H), 2.75 (t, 2H), 2.83 (m, 1H), 3.29 (m, 2H), 4.13 (m, 2H), 6.73 (d, 1H), 7.23 (d, 1H), 7.41 (m, 1H), 7.51 (d, 1H), 7.67 (d, 1H), 7.72 (d, 1H), 7.78 (d, 1H), 7.89 (m, 1H), 8.51 (t, 1H); Mass Spectrum: M+H$^+$ 422.

The 3-[7-(2-chloroethoxy)-1-oxoisoquinolin-2(1H)-yl]-N-ethyl-4-methylbenzamide used as starting material was prepared as follows:—

N-Ethyl-3-(7-hydroxy-1-oxoisoquinolin-2(1H)-yl)-4-methylbenzamide (0.65 g), 1-bromo-2-chloroethane (0.8 ml) and potassium carbonate (2.6 g) were stirred in DMF (26 ml) at 50° C. for 23 hours. The reaction mixture was diluted with ethyl acetate and washed with water (×5), brine (×2), dried (magnesium sulfate) and concentrated to give 3-[7-(2-chloroethoxy)-1-oxoisoquinolin-2(1H)-yl]-N-cyclopropyl-4-methylbenzamide as a foam (577 mg); NMR Spectrum: (DMSO d$_6$) 1.17 (t, 3H), 2.16 (s, 3H), 3.34 (m, 2H), 4.05 (t, 2H), 4.45 (m, 2H), 6.80 (d, 1H), 7.30 (d, 1H), 7.53 (m, 2H), 7.74 (d, 1H), 7.82 (m, 1H), 7.94 (d, 1H), 8.51 (t, 1H); Mass Spectrum: M+H$^+$ 385.

EXAMPLE 31

Using an analogous procedure to that described in Example 30, N-Ethyl-3-(7-hydroxy-1-oxoisoquinolin-2

(1H)-yl)-4-methylbenzamide was alkylated with the appropriate alkylating reagent to give the compounds described in Table 9.

TABLE 9

| R | Method | Note |
|---|---|---|
| (3R)-3-Fluoropyrrolidin-1-yl | Ex 30 | a |
| Piperidin-1-yl | Ex 30 | b |
| Azetidin-1-yl[1] | Ex 30 | c |
| Allyl(methyl)amino | Ex 30 | d |
| Ethyl(methyl)amino | Ex 30 | e |
| Diethylamino | Ex 30 | f |
| Isopropyl(ethyl)amino | Ex 30 | g |
| (3R)-3-Hydroxypyrrolidin-1-yl | Ex 30 | h |
| Pyrrolidin-1-yl | Ex 30 | i |
| 4-Hydroxypiperidin-1-yl | Ex 30 | j |
| Methyl[(2-methyl-1,3-thiazol-4-yl)methyl]amino | Ex 30 | k |
| 4-Fluoropiperidin-1-yl | Ex 30 | l |
| (3aR,6aS)-tetrahydro-5H-[1,3]dioxolo[4,5-c]pyrrol-5-yl | Ex 30 | m |
| tert-Butyl(methyl)amino | Ex 30 | n |

[1]Potassium carbonate used as base

Notes a The product gave the following data; NMR Spectrum: (DMSOd$_6$) 1.13 (t, 3 H), 1.39 (m, 1 H), 2.12 (s, 3 H), 2.14 (m, 1 H), 2.45 (m, 1 H), 2.73 (m, 1 H), 2.89 (m, 4 H), 3.28 (m, 2 H, masked by water), 4.20 (m, 2 H), 5.22 (m, 1 H), 6.74 (d, 1 H), 7.23 (d, 1 H), 7.43 (m, 1 H), 7.51 (d, 1 H), 7.48 (s, 1 H), 7.72 (d, 1 H), 7.77 (s, 1 H), 7.90 (d, 1 H), 8.48 (t, 1 H); Mass Spectrum: M + H$^+$ 438.

b The product gave the following data; NMR Spectrum: (DMSOd$_6$) 1.12 (t, 3 H), 1.38 (m, 2 H), 1.50 (m, 4 H), 2.11 (s, 3 H), 2.46 (m, 4 H), 2.71 (t, 2 H), 3.29 (m, 3 H), 4.19 (m, 2 H), 6.73 (d, 1 H), 7.22 (d, 1 H), 7.42 (m, 1 H), 7.51 (d, 1 H), 7.68 (s, 1 H), 7.71 (d, 1 H), 7.78 (s, 1 H), 7.89 (d, 1 H), 8.47 (t, 1 H); Mass Spectrum: M + H$^+$ 434.

c The product gave the following data; NMR Spectrum: (CDCl$_3$) 1.14 (t, 3 H), 2.05 (m, 2 H), 2.12 (s, 3 H), 2.80 (t, 2 H), 3.26 (t, 4 H), 3.38 (m, 2 H), 4.02 (t, 2 H), 6.16 (m, 1 H), 6.45 (m, 1 H), 6.80 (m, 1 H), 7.25 (m, 1 H), 7.33 (d, 1 H), 7.41 (d, 1 H), 7.56 (d, 1 H), 7.69 (m, 1 H), 7.74 (d, 1 H); Mass Spectrum: M + H$^+$ 406.

d The product gave the following data; NMR Spectrum: (CDCl$_3$) 1.14 (t, 3 H), 2.29 (s, 3 H), 2.29 (s, 3 H), 2.80 (t, 2 H), 3.07 (d, 2 H), 3.38 (m, 2 H), 4.14 (t, 2 H), 5.13 (m, 2 H), 5.83 (m, 1 H), 6.17 (m, 1 H), 6.46 (m, 1 H), 6.81 (m, 1 H), 7.26 (m, 1 H), 7.33 (d, 1 H), 7.42 (d, 1 H), 7.56 (d, 1 H), 7.69 (m, 1 H), 7.77 (d, 1 H); Mass Spectrum: M + H$^+$ 420.

e The product gave the following data; NMR Spectrum: (CDCl$_3$) 1.04 (t, 3 H), 1.14 (t, 3 H), 2.30 (s, 3 H), 2.30 (s, 3 H), 2.50 (q, 2 H), 2.80 (t, 2 H), 3.37 (m, 2 H), 4.15 (t, 2 H), 6.20 (q, 1 H), 6.45 (m, 1 H), 6.81 (m, 1 H), 7.26 (m, 1 H), 7.32 (d, 1 H), 7.41 (d, 1 H), 7.56 (d, 1 H), 7.69 (m, 1 H), 7.77 (d, 1 H); Mass Spectrum: M + H$^+$ 408.

f The product gave the following data; NMR Spectrum: (CDCl$_3$) 1.02 (t, 6 H), 1.13 (m, 3 H), 2.12 (s, 3 H), 2.60 (q, 4 H), 2.88 (t, 2 H), 3.36 (m, 2 H), 4.12 (t, 2 H), 6.23 (m, 1 H), 6.44 (m, 1 H), 6.80 (m, 1 H), 7.25 (m, 1 H), 7.32 (d, 1 H), 7.41 (d, 1 H), 7.56 (d, 1 H), 7.69 (q, 1 H), 7.77 (d, 1 H); Mass Spectrum: M + H$^+$ 422.

g The product gave the following data; NMR Spectrum: (CDCl$_3$) 1.01 (m, 9 H), 1.14 (t, 3 H), 2.12 (s, 3 H), 2.56 (m, 2 H), 2.81 (t, 2 H), 2.98 (m, 1 H), 3.38 (m, 2 H), 4.06 (t, 2 H), 6.19 (m, 1 H), 6.45 (m, 1 H), 6.80 (m, 1 H), 7.24 (m, 1 H), 7.33 (d, 1 H), 7.41 (d, 1 H), 7.56 (d, 1 H), 7.69 (m, 1 H), 7.77 (d, 1 H); Mass Spectrum: M + H$^+$ 436.

h The product gave the following data; NMR Spectrum: (CDCl$_3$) 1.12 (t, 3 H), 1.71 (m, 1 H), 2.14 (m, 4 H), 2.43 (m, 1 H), 2.65 (m, 1 H), 2.76 (m, 1 H), 2.91 (m, 4 H), 3.37 (m, 2 H), 4.17 (t, 2 H), 4.29 (m, 1 H), 6.16 (m, 1 H), 6.46 (m, 1 H), 6.82 (m, 1 H), 7.24 (m, 1 H), 7.32 (d, 1 H), 7.42 (d, 1 H), 7.57 (d, 1 H), 7.69 (m, 1 H), 7.79 (d, 1 H); Mass Spectrum: M + H$^+$ 436.

i The product gave the following data; NMR Spectrum: (CDCl$_3$) 1.12 (t, 3 H), 1.76 (m, 4 H), 2.12 (s, 3 H), 2.61 (m, 4 H), 2.91 (t, 2 H), 3.37 (m, 2 H), 4.19 (t, 2 H), 6.22 (m, 1 H), 6.44 (m, 1 H), 6.80 (m, 1 H), 7.29 (m, 2 H), 7.41 (d, 1 H), 7.56 (d, 1 H), 7.69 (m, 1 H), 7.77 (d, 1 H); Mass Spectrum: M + H$^+$ 420.

j The product gave the following data; NMR Spectrum: (CDCl$_3$) 1.17 (t, 3 H), 1.59 (m, 2 H), 1.86 (m, 2 H), 2.15 (s, 3 H), 2.33 (m, 2 H), 2.85 (m, 4 H), 3.40 (m, 2 H), 3.68 (m, 1 H), 4.20 (t, 2 H), 6.26 (m, 1 H), 6.49 (m, 1 H), 6.84 (m, 1 H), 7.28 (m, 1 H), 7.35 (d, 1 H), 7.45 (d, 1 H), 7.59 (d, 1 H), 7.72 (m, 1 H), 7.79 (d, 1 H); Mass Spectrum: M + H$^+$ 450.

k The product gave the following data; NMR Spectrum: (CDCl$_3$) 1.15 (t, 3 H), 2.12 (s, 3 H), 2.62 (s, 3 H), 2.62 (s, 3 H), 2.87 (t, 2 H), 3.36 (m, 2 H), 3.71 (s, 2 H), 4.18 (t, 2 H), 6.23 (m, 1 H), 6.44 (m, 1 H), 6.80 (m, 1 H), 6.94 (s, 1 H), 7.24 (m, 1 H), 7.31 (d, 1 H), 7.40 (d, 1 H), 7.56 (d, 1 H), 7.69 (m, 1 H), 7.74 (d, 1 H); Mass Spectrum: M + H$^+$ 491.

l The product gave the following data; NMR Spectrum: (CDCl$_3$) 1.14 (t, 3 H), 1.88 (m, 4 H), 2.13 (s, 3 H), 2.47 (m, 2 H), 2.67 (m, 2 H), 2.80 (t, 2 H), 3.38 (m, 2 H), 4.17 (t, 2 H), 4.60 (m, 1 H), 6.17 (m, 1 H), 6.46 (m, 1 H), 6.82 (m, 1 H), 7.25 (m, 1 H), 7.33 (d, 1 H), 7.43 (d, 1 H), 7.57 (m, 1 H), 7.69 (m, 1 H), 7.77 (d, 1 H); Mass Spectrum: M + H$^+$ 452.

m The product gave the following data; NMR Spectrum: (CDCl$_3$) 1.14 (t, 3 H), 2.13 (s, 3 H), 2.28 (m, 2 H), 2.81 (t, 2 H), 3.17 (m, 2 H), 3.38 (m, 2 H), 4.17 (t, 2 H), 4.52 (m, 2 H), 4.81 (s, 1 H), 5.06 (s, 1 H), 6.16 (m, 1 H), 6.46 (m, 1 H), 6.82 (m, 1 H), 7.23 (m, 1 H), 7.33 (d, 1 H), 7.42 (d, 1 H), 7.56 (d, 1 H), 7.69 (m, 1 H), 7.75 (d, 1 H); Mass Spectrum: M + H$^+$ 464.

n The product gave the following data; NMR Spectrum: (DMSOd$_6$) 1.03 (s, 9 H), 1.12 (t, 3 H), 2.11 (s, 3 H), 2.26 (s, 3 H), 2.75 (t, 2 H), 3.29 (m, 2 H), 4.09 (m, 2 H), 6.73 (d, 1 H), 7.23 (d, 1 H), 7.40 (m, 1 H), 7.51 (d, 1 H), 7.67 (d, 1 H), 7.72 (d, 1 H), 7.78 (d, 1 H), 7.89 (m, 1 H), 8.51 (t, 1 H); Mass Spectrum: M + H$^+$ 436.

The invention claimed is:

1. A compound of the Formula I

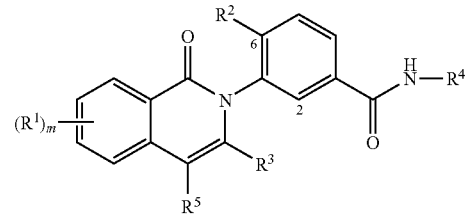

wherein m is 0, 1 or 2;

$R^1$ is halogeno, hydroxy, cyano, trifluoromethyl, trifluoromethoxy, (1-6C)alkyl, (1-6C)alkoxy, (2-6C)alkenyl, (2-6C)alkynyl, (2-6C)alkanoyl, (1-6C)alkylthio, (1-6C)alkylsulphinyl, (1-6C)alkylsulphonyl, hydroxy-(2-6C)alkoxy, amino-(2-6C)alkoxy, cyano-(2-6C)alkoxy, (1-6C)alkylamino-(2-6C)alkoxy, di-[(1-6C)alkyl]amino-(2-6C)alkoxy, (1-6C)alkoxy-(2-6C)alkoxy, carbamoyl-(1-6C)alkoxy, N-(1-6C)alkylcarbamoyl-(1-6C)alkoxy, amino-(1-6C)alkyl, (1-6C)alkylamino-(1-6C)alkyl, di[(1-6C)alkyl]amino-(1-6C)alkyl, carbamoyl-(1-6C)alkyl, N-(1-6C)alkylcarbamoyl-(1-6C)alkyl, hydroxy-(2-6C)alkylamino, cyano-(2-6C)alkylamino, halogeno-(2-6C)alkylamino, amino-(2-6C)alkylamino, (1-6C)alkoxy-(2-6C)alkylamino, (1-6C)alkylamino-(2-6C)alkylamino, di-[(1-6C)alkyl]amino-(2-6C)alkylamino, heteroaryl, heteroaryl-(1-6C)alkyl, heteroaryloxy, heteroaryl-(1-6C)alkoxy, heteroarylamino, heterocyclyl, heterocyclyl-(1-6C)alkyl, heterocyclyloxy, heterocyclyl-(1-6C)alkoxy and heterocyclylamino, and wherein any aryl, heteroaryl or heterocyclyl group in a $R^1$ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the $R^1$ substituents defined hereinbefore which comprises a $CH_2$ group which is attached to 2 carbon atoms or a $CH_3$ group which is attached to a carbon or nitrogen atom may optionally bear on each said $CH_2$ or $CH_3$ group one or more substituents selected from halogeno, hydroxy, amino, trifluoromethyl, trifluoromethoxy, oxo, carboxy, carbamoyl, acetamido, (1-6C)alkyl, (2-6C)alkenyl, (2-6C)alkynyl, (3-6C)cycloalkyl, (3-6C)cycloalkoxy, (1-6C)alkoxy, (1-6C)alkylamino, di-[(1-6C)alkyl]amino, hydroxy-(1-6C)alkyl, (1-6C)alkoxy-(1-6C)alkyl, halogeno-(1-6C)alkyl, (1-6C)alkoxy-(2-6C)alkoxy, (1-6C)alkoxycarbonyl, carbamoyl, N-(1-6C)alkylcarbamoyl, N,N-di-[(1-6C)alkyl]carbamoyl, (1-6C)sulphonyl, (1-6C)sulphamoyl, heteroaryl, heteroaryl-(1-6C)alkyl, heterocyclyl and heterocyclyloxy, and wherein any heterocyclyl group in a $R^1$ substituent may optionally bear 1 or 2 oxo or thioxo substituents;

$R^2$ is halogeno, trifluoromethyl or (1-6C)alkyl;

$R^3$ is hydrogen, halogeno, trifluoromethyl, cyano or (1-6C)alkyl;

$R^4$ is (3-6C)cycloalkyl, (1-6C)alkyl or heteroaryl, and $R^4$ may be optionally substituted by one or more substituents selected from halogeno, hydroxy, amino, (1-6C)alkyl, (2-6C)alkenyl, (2-6C)alkynyl, (1-6C)alkoxy, (1-6C)alkylamino and di-[(1-6C)alkyl]amino; and $R^5$ is hydrogen, halogeno, trifluoromethyl, cyano or (1-6C)alkyl;

or a pharmaceutically-acceptable salt thereof.

2. The compound of the Formula I according to claim 1 wherein $R^1$ is halogeno, hydroxy, (1-6C)alkoxy, (2-6C)alkenyl, (2-6C)alkynyl, (2-6C)alkanoyl, (1-6C)alkylthio, (1-6C)alkylsulphonyl, amino-(2-6C)alkoxy, (1-6C)alkylamino-(2-6C)alkoxy, di-[(1-6C)alkyl]amino-(2-6C)alkoxy, di[(1-6C)alkyl]amino-(1-6C)alkyl, carbamoyl-(1-6C)alkyl, heteroaryl-(1-6C)alkyl, heterocyclyl, heterocyclyloxy and heterocyclyl-(1-6C)alkoxy, and wherein any heteroaryl or heterocyclyl group in a $R^1$ substituent may optionally bear 1 or 2 substituents selected from hydroxy, halogeno, (1-6C)alkyl, (3-6C)cycloalkyl-(1-6C)alkyl, (3-6C)cycloalkyl-(1-6C)alkoxy, (1-6C)alkoxy, (1-6C)alkoxycarbonyl-(1-6C)alkyl, N-(1-6C)alkylcarbamoyl, N,N-di-[(1-6C)alkyl]carbamoyl, halogeno-(1-6C)alkyl, hydroxy-(1-6C)alkyl, (1-6C)alkoxy-(1-6C)alkyl, cyano-(1-6C)alkyl, and wherein any of the $R^1$ substituents defined hereinbefore which comprises a $CH_2$ group which is attached to 2 carbon atoms or a $CH_3$ group which is attached to a carbon or nitrogen atom may optionally bear on each said $CH_2$ or $CH_3$ group one or more substituents selected from halogeno, hydroxy, trifluoromethyl, (1-6C)alkyl, (3-6C)cycloalkyl, (1-6C)alkoxy, di-[(1-6C)alkyl]amino, (1-6C)alkoxy-(1-6C)alkyl, (1-6C)alkoxycarbonyl, heteroaryl-(1-6C)alkyl, heterocyclyl and heterocyclyloxy;

or a pharmaceutically-acceptable salt thereof.

3. The compound of the Formula I according to claim 1 wherein m is 1 or 2; or a pharmaceutically-acceptable salt thereof.

4. The compound of the Formula I according to claim 1 wherein $R^2$ is (1-6C)alkyl; or a pharmaceutically-acceptable salt thereof.

5. The compound of the Formula I according to claim 1 wherein $R^3$ and $R^5$ are hydrogen; or a pharmaceutically-acceptable salt thereof.

6. The compound of the Formula I according to claim 1 wherein $R^4$ is cyclopropyl, cyclobutyl, cyclopentyl, methoxy, ethoxy, methyl, ethyl, propyl, isoxazolyl, oxazolyl, furanyl, thiazolyl, pyrazolyl or pyridyl; or a pharmaceutically-acceptable salt thereof.

7. The compound of the Formula I according to claim 1 wherein m is 0 or 1;

$R^1$ is heterocyclyl, heterocyclyl-(1-6C)alkyl, heterocyclyloxy, heterocyclyl-(1-6C)alkoxy or heterocyclylamino, and wherein any heterocyclyl group in a $R^1$ substituent may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (3-6C)cycloalkyl-(1-6C)alkoxy, (1-6C)alkoxy, carboxy, (1-6C)alkoxycarbonyl, (1-6C)alkoxycarbonyl-(1-6C)alkyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl and di-[(1-6C)alkyl]amino-(1-6C)alkyl, and wherein any of the $R^1$ substituents defined hereinbefore which comprises a $CH_2$ group which is attached to 2 carbon atoms or a $CH_3$ group which is attached to a carbon atom may optionally bear on each said $CH_2$ or $CH_3$ group one or more substituents selected from hydroxy, amino, (1-6C)alkyl, (2-6C)alkenyl, (2-6C)alkynyl, (1-6C)alkoxy, (1-6C)alkylamino and di-[(1-6C)alkyl]amino;

$R^2$ is trifluoromethyl or methyl;

$R^3$ is hydrogen or chloro;

$R^4$ is cyclopropyl, cyclobutyl, cyclopentyl, methyl, ethyl, propyl, isoxazolyl, oxazolyl, furanyl, thiazolyl, pyrazolyl or pyridyl, and $R^4$ may be optionally substituted by one or more substituents selected from halogeno, hydroxy, amino and (1-6C)alkyl; and $R^5$ is hydrogen or chloro;

or a pharmaceutically-acceptable salt thereof.

8. The compound of the Formula I according to claim 1 selected from:

N-cyclopropyl-4-methyl-3-(1-oxoisoquinolin-2(1H)-yl)benzamide;

N-cyclopropyl-3-(7-methoxy-l-oxoisoquinolin-2(1H)-yl1)-4-methylbenzamide;

N-cyclopropyl-3-[7-[2-(dimethylamino)ethoxy]-1-oxoisoquinolin-2(1H)-yl]-4-methylbenzamide;

3-(7-bromo-1-oxoisoquinolin-2(1H)-yl)-N-cyclopropyl-4-methylbenzamide;

N-cyclopropyl-4-methyl-3-[1-oxo-7-(2-piperidin-1-ylethoxy)isoquinolin-2(1H)-yl]benzamide;

N-cyclopropyl-3-(7-hydroxy-l-oxoisoquinolin-2(1H)-yl)-4-methylbenzamide;

N-cyclopropyl-3-[7-{2-[(3R)-3-fluoropyrrolidin-l-yl]ethoxy}-1-oxoisoquinolin-2(1H)-yl]-4-methylbenzamide;

N-cyclopropyl-4-methyl -3-[7[2-(1,4-oxazepan-4-yl)ethoxy]-1-oxoisoquinolin-2(1H)-yl]benzamide;

N-cyclopropyl-3-[7-{2-[(2-methoxyethyl)(methyl)amino]ethoxy}-1-oxoisoquinolin-2(1H)-yl]-4-methylbenzamide;

3-[7-{2-[(cyclobutylmethyl)(methyl)amino]ethoxy}-1-oxoisoquinolin-2(1H)-yl]-N-cyclopropyl-4-methylbenzamide;

N-cyclopropyl-4-methyl -3-[7-(2-morpholin-4-ylethoxy)-1-oxoisoquinolin-2(1H)-yl]benzamide;

N-cyclopropyl-4-methyl-3-[1-oxo-7-(2-pyrrolidin-1-ylethoxy)isoquinolin-2(1H)-yl]benzamide;

N-cyclopropyl-3-[7-{2-[(3R)-3-hydroxypyrrolidin-1-yl]ethoxy}-1-oxoisoquinolin-2(1H)-yl]-4-methylbenzamide;

N-cyclopropyl-3-[7-{2-[(2S)-2-(methoxymethyl)pyrrolidin-1-yl]ethoxy}-1-oxoisoquinolin-2(1H)-yl]-4-methylbenzamide;

N-cyclopropy-3-[7-{2-[isopropyl(2-methoxyethyl)amino]ethoxy}-1-oxoisoquinolin-2(1H)-yl]-4-methylbenzamide;

N-cyclopropyl-3-[7-{2-[isopropyl(methyl)amino]
ethoxy}-1-oxoisoquinolin-2(1H)-yl]-4-methylbenzamide;

N-cyclopropyl-3-[7-[3-(dimethylamino)propoxy]-1-oxoisoquinolin-2(1H)-yl]-4-methylbenzamide;

3-[7-[2-(dimethylamino)ethoxy]-1-oxoisoquinolin-2(1H)-yl]-N-isoxazol-3-yl-4-methylbenzamide;

3-[7-[2-(dimethylamino)ethoxy]-1-oxoisoquinolin-2(1H)-yl]-N-ethyl-4-methylbenzamide;

N-cyclopropyl-3-[7-[(1-ethylpiperidin-4-yl)oxy]-1-oxoisoquinolin-2(1H)-yl]-4-methylbenz amide;

N-isoxazol-3-yl -4-methyl -3-[7-(4-methylpiperazin-1-yl)-1-oxoisoquinolin-2(1H)-yl]benzamide;

N-cyclopropyl-4-methyl-3-[7-(4-methylpiperazin-1-yl)-1-oxoisoquinolin-2(1H)-yl]benzamide;

N-cyclopropyl-4-methyl-3-[7-{2-[methyl(tetrahydro-2H-pyran-4-yl)amino]ethoxy}-1-oxoisoquinolin-2(1H)-yl]benzamide;

N-cyclopropyl-4-methyl-3-[7-{2-[methyl(tetrahydrofuran-2-ylmethyl)amino]ethoxy}-1-oxoisoquinolin-2(1H)-yl]benzamide;

N-cyclopropyl-4-methyl-3-[7-{2-[methyl(prop-2-yn-1-yl)amino]ethoxy}-1-oxoisoquinolin-2(1H)-yl]benzamide;

N-cyclopropyl-3-[7-{2-[(3S)-3-fluoropyrrolidin-1-yl]ethoxy}-1-oxoisoquinolin-2(1H)-yl]-4-methylbenzamide;

N-cyclopropy-3-[7-[2-(4,4-difluoropiperidin-1-yl)ethoxy]-1-oxoisoquinolin-2(1H)-yl]-4-methylbenzamide;

N-cyclopropyl-3-[7-[2-(3,3-difluoropyrrolidin-1-yl)ethoxy]-1-oxoisoquinolin-2(1H)-yl]-4-methylbenzamide;

N-cyclopropy-3-[7-[2-(4-fluoropiperidin-1-yl)ethoxy]-1-oxoisoquinolin-2(1H)-yl]-4-methylbenzamide;

N-cyclopropy-3-[7-[2-(3-fluoropiperidin-1-yl)ethoxy]-1-oxoisoquinolin-2(1H)-yl]-4-methylbenzamide;

N-cyclopropy-3-[7-{2-[(2S,6S)-2,6-dimethylmorpholin-4-yl]ethoxy}-1-oxoisoquinolin-2(1H)-yl]-4-methylbenzamide;

N-cyclopropyl-3-[7-{2-[(2R,6S)-2,6-dimethylmorpholin-4-yl]ethoxy}-1-oxoisoquinolin-2(1H)-yl]-4-methylbenzamide;

N-cyclopropyl -4-methyl-3-[1-oxo-7-[3-(4-propionylpiperazin-1-yl)propoxy]isoquinolin-2(1H)-yl]benzamide;

N-ethyl-4-methyl-3-[7-(2-morpholin-4-ylethoxy)-1-oxoisoquinolin-2(1H)-yl]benzamide;

N-cyclopropyl-3-[7-[3-(4,4-difluoropiperidin-1-yl)propoxy]-1-oxoisoquinolin-2(1H)-yl]-4-methylbenzamide;

N-cyclopropyl-3-[7-{3-[isopropyl(methyl)amino]propoxy}-1-oxoisoquinolin-2(1H)-yl]-4-methylbenzamide;

N-cyclopropyl-4-methyl-3-[1-oxo-7-(3-piperidin-1-yl-propoxy)isoquinolin-2(1H)-yl]benzamide;

N-cyclopropyl-4-methyl-3-[7-{3-[methyl(tetrahydrofuran-2-ylmethyl)amino]propoxy}-1-oxoisoquinolin-2(1H)-yl]benzamide;

N-cyclopropyl-3-[7-{3-[(2R,6S)-2,6-dimethylmorpholin-4-yl]propoxy}-1-oxoisoquinolin-2(1H)-yl]-4-methylbenzamide;

N-cyclopropyl -4-methyl-3-[1-oxo-7-(3-pyrrolidin-1-yl-propoxy)isoquinolin-2(1H)-yl]benzamide;

N-cyclopropyl -4-methyl-3-[7-(3-morpholin-4-ylpropoxy)-1-oxoisoquinolin-2(1H)-yl]benzamide;

N-cyclopropyl-4-methyl-3-[7-{3-[methyl(prop-2-yn-1-yl)amino]propoxy}-1-oxoisoquinolin-2(1H)-yl]benzamide;

N-cyclopropyl-3-[7-[3-(3,3-difluoropyrrolidin-1-yl)propoxy]-1-oxoisoquinolin-2(1H)-yl]-4-methylbenzamide;

N-cyclopropyl3-[7-3-(3-fluoropiperidin-1-yl)propoxy]-1-oxoisoquinolin-2(1H)-yl]-4-methylbenzamide;

N-cyclopropyl-4-methyl-3-[7-{2-[4-(methylsulfonyl)piperazin-1-yl]ethoxy}-1-oxoisoquinolin-2(1H)-yl]benzamide;

N-ethyl-3-[7-{2-[isopropyl(methyl)amino]ethoxy}-1-oxoisoquinolin-2(1H)-yl]-4-methylbenz amide;

N-ethyl-3-[7-{2-[(3R)-3-fluoropyrrolidin-1-yl]ethoxy}-1-oxoisoquinolin-2(1H)-yl]-4-methylbenz amide;

N-cyclopropyl -4-methyl-3-[7-{3-[methyl(tetrahydro-2H-pyran-4-yl)amino]propoxy}-1-oxoisoquinolin-2(1H)-yl]benzamide;

3-[7-[3-(dimethylamino)propyl]-1-oxoisoquinolin-2(1H)-yl]-N-isoxazol-3-yl-4-methylbenzamide;

N-cyclopropyl-3-[7-[3-(4-fluoropiperidin-1-yl)propoxy]-1-oxoisoquinolin-2(1H)-yl]-4-methylbenz amide;

N-cyclopropyl-3-[7-{3-[(3R)-3-fluoropyrrolidin-1-yl]propoxy}-1-oxoisoquinolin-2(1H)-yl]-4-methylbenzamide;

N-cyclopropyl-3-[7-{3-[(3S)-3-fluoropyrrolidin-1-yl]propoxy}-1-oxoisoquinolin-2(1H)-yl]-4-methylbenzamide;

N-ethyl-4-methyl-3-[1-oxo-7-(2-piperidin-1-ylethoxy)isoquinolin-2(1H)-yl]benzamide;

N-ethyl-3-(7-hydroxy-1-oxoisoquinolin-2(1H)-yl)-4-methylbenzamide;

N-cyclopropyl-3-[7-{2-[isobutyl(methyl)amino]ethoxy}-1-oxoisoquinolin-2(1H)-yl]-4-methylbenzamide;

N-cyclopropy-3-[7-{2-[ethyl(methyl)amino]ethoxy}-1-oxoisoquinolin-2(1H)-yl]-4-methylbenz amide;

N-cyclopropyl-3-[7[2-(diisopropylamino)ethoxy]-1-oxoisoquinolin-2(1H)-yl]-4-methylbenz amide;

N-cyclopropyl-4-methyl-3-[7-{2-[(2S)-2-methylpiperidin-1-yl]ethoxy}-1-oxoisoquinolin-2(1H)-yl]benzamide;

N-cyclopropyl-3-[7-{2-[ethyl(isopropyl)amino]ethoxy}-1-oxoisoquinolin-2(1H)-yl]-4-methylbenzamide;

N-cyclopropyl-3-[7-[2-(diethylamino)ethoxy]-1-oxoisoquinolin-2(1H)-yl]-4-methylbenzamide;

3-[7-{2-[tert-butyl(methyl)amino]ethoxy}-1-oxoisoquinolin-2(1H)-yl]-N-cyclopropyl-4-methylbenzamide;

3-[7-{2-[cyclohexyl(isopropyl)amino]ethoxy}-1-oxoisoquinolin-2(1H)-yl]-N-cyclopropyl-4-methylbenzamide;

3-[7-{2-[cyclohexyl(ethyl)amino]ethoxy}-1-oxoisoquinolin-2(1H)-yl]-N-cyclopropyl-4-methylbenzamide;

3-[7-{2-[cyclohexyl(methyl)amino]ethoxy}-1-oxoisoquinolin-2(1H)-yl]-N-cyclopropyl-4-methylbenzamide;

N-cyclopropyl-3-[7-{2-[2-(hydroxymethyl)morpholin-4-yl]ethoxy}-1-oxoisoquinolin-2(1H)-yl]-4-methylbenzamide;

N-cyclopropyl-3-[7-{2-[(2S)-2-(hydroxymethyl)piperidin-1-yl]ethoxy}-1-oxoisoquinolin-2(1H)-yl]-4-methylbenzamide;

3-[7-(2-azetidin-1-ylethoxy)-1-oxoisoquinolin-2(1H)-yl]-N-ethyl-4-methylbenzamide;

N-cyclopropyl-3-[7-[2-(isopropylamino)ethoxy]-1-oxoisoquinolin-2(1H)-yl]-4-methylbenz amide;

3-[7-{2-[allyl(methyl)amino]ethoxy}-1-oxoisoquinolin-2 (1H)-yl]-N-ethyl-4-methylbenzamide;
N-ethyl-3-[7-{2-[ethyl(methyl)amino]ethoxy}-1-oxoisoquinolin-2(1H)-yl]-4-methylbenzamide;
3-[7-[2-(diethylamino)ethoxy]-1-oxoisoquinolin-2(1H)-yl]-N-ethyl-4-methylbenzamide;
N-ethyl-3-[7-{2-[ethyl(isopropyl)amino]ethoxy}-1-oxoisoquinolin-2(1H)-yl]1]-4-methylbenzamide;
N-cyclobutyl-3-(7-hydroxy-1-oxoisoquinolin-2(1H)-yl]-4-methylbenzamide;
N-cyclopropyl-4-methyl-3-[7-[2-(methylamino)ethoxy]-1-oxoisoquinolin-2(1H)-yl]benzamide;
N-ethyl-3-[7-{2-[(3R)-3-hydroxypyrrolidin-1-yl]ethoxy}-1-oxoisoquinolin-2(1H)-yl]-4-methylbenzamide;
N-ethyl-4-methyl-3-[1-oxo-7-(2-pyrrolidin-1-ylethoxy)isoquinolin-2(1H)-yl]benzamide;
N-ethyl-3-[7-[2-(4-hydroxypiperidin-1-yl)ethoxy]-1-oxoisoquinolin-2(1H)-yl]-4-methylbenzamide;
N-ethyl-4-methyl-3-[7-[2-{methyl[(2-methyl-1,3-thiazol-4-yl)methyl]amino}ethoxy)-1-oxoisoquinolin-2(1H)-yl]benzamide;
N-ethyl-3-[7-[2-(4-fluoropiperidin-1-yl)ethoxy]-1-oxoisoquinolin-2(1H)-yl]-4-methylbenzamide;
N-ethyl-4-methyl-3-[1-oxo-7-{2-[(3aR,6aS)-tetrahydro-5H-[1,3          ]dioxolo[4,5-c]pyrrol-5-yl]ethoxy}isoquinolin-2(1H)-yl]benzamide;
3-(7-hydroxy-1-oxoisoquinolin-2(1H)-yl)-4-methyl-N-(1-methylcyclopropyl)benzamide;
N-isoxazol-3-yl-4-methyl-3-[7-(3-morpholin-4-ylpropyl)-1-oxoisoquinolin-2(1H)-yl]benzamide;
N-isoxazol-3-yl-4-methyl-3-[7-(2-morpholin-4-ylethoxy)-1-oxoisoquinolin-2(1H)-yl]benzamide;
3-[7-(2-aminoethoxy)-1-oxoisoquinolin-2(1H)-yl]-N-cyclopropyl-4-methylbenzamide;
N-isoxazol-3-yl-4-methyl-3-[1-oxo-7-(2-piperidin-1-ylethoxy)isoquinolin-2(1H)-yl]benzamide;
3-[7-{2-[tert-butyl(methyl)amino]ethoxy}-1-oxoisoquinolin-2(1H)-yl]-N-ethyl-4-methylbenzamide;
3-[7-{2-[isopropyl(methyl)amino]ethoxy}-1-oxoisoquinolin-2(1H)-yl]-4-methyl-N-(1-methyl-1H-pyrazol-3-yl)benzamide;
3-[7-{2-[isopropyl(methyl)amino]ethoxy}-1-oxoisoquinolin-2(1H)-yl]-4-methyl-N-(1-methyl-1H-pyrazol-3-yl)benzamide;
3-[7-{2-[isopropyl(methyl)amino]ethoxy}-1-oxoisoquinolin-2(1H)-yl]-N-methoxy-4-methylbenzamide;
N-cyclobutyl-3-[7-{2-[isopropyl(methyl)amino]ethoxy}-1-oxoisoquinolin-2(1H)-yl]-4-methylbenzamide;
N-cyclopropyl-3-(7-methoxy-4-methyl-1-oxoisoquinolin-2(1H)-yl)-4-methylbenzamide;
N-cyclopropyl-3-[7-{2-[isopropyl(methyl)amino]ethoxy}-4-methyl-1-oxoisoquinolin-2(1H)-yl]-4-methylbenzamide;
N-ethyl-3-[7-{2-[isopropyl(methyl)amino]ethoxy}-4-methyl-1-oxoisoquinolin-2(1H)-yl]-4-methylbenzamide;
N-cyclopropyl -3[4-(hydroxymethyl)-7-methoxy-1-oxoisoquinolin-2(1H)-yl]-4-methylbenzamide;
N-ethyl-3-[7-{2-[ethyl(methyl)amino]ethoxy}-4-methyl-1-oxoisoquinolin-2(1H)-yl]-4-methylbenzamide;
3-[7-[2-(dimethylamino)ethoxy]-4-methyl-1-oxoisoquinolin-2(1H)-yl]-N-ethyl -4-methylbenzamide;
N-cyclobutyl-3-[7-{2-[isopropyl(methyl)amino]ethoxy}-4-methyl-1-oxoisoquinolin-2(1H)-yl]-4-methylbenzamide;
N-cyclobutyl-3-[7-{2-[ethyl(methyl)amino]ethoxy}-4-methyl-1-oxoisoquinolin-2(1H)-yl]-4-methylbenzamide; and
N-cyclobutyl -3-[7-[2-(dimethylamino)ethoxy]-4-methyl-1-oxoisoquinolin-2(1H)-yl]-4-methylbenzamide;
and pharmaceutically-acceptable salts thereof.

9. A process for preparing a compound of the Formula I according to claim 1, or pharmaceutically-acceptable salt thereof which comprises:— the dehydration of a compound of the Formula II

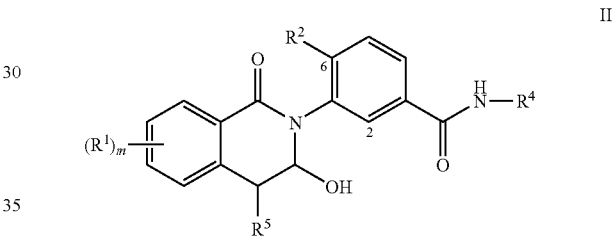

wherein $R^1$, m, $R^2$, $R^4$ and $R^5$ are as defined in claim 1 and wherein any functional group is optionally protected, and:
(i) removing any protecting groups; and
(ii) optionally forming a pharmaceutically-acceptable salt.

10. A method of treating arthritis which comprises administering to a warm-blooded animal an effective amount of a compound of the Formula I claimed in any one of claims 1 to 8, or a pharmaceutically-acceptable salt thereof.

11. The method according to claim 10 wherein the arthritis is rheumatoid arthritis.

* * * * *